(12) United States Patent
Vijendra et al.

(10) Patent No.: US 9,792,658 B1
(45) Date of Patent: Oct. 17, 2017

(54) HEALTHBOOK ANALYSIS

(71) Applicant: EMC Corporation, Hopkinton, MA (US)

(72) Inventors: Sudhir Vijendra, Lexington (MA); Patricia G. S. Florissi, Briarcliff Manor, MA (US)

(73) Assignee: EMC IP Holding Company LLC, Hopkinton, MA (US)

( * ) Notice: Subject to any disclaimer, the term of this patent is extended or adjusted under 35 U.S.C. 154(b) by 128 days.

(21) Appl. No.: 14/041,067

(22) Filed: Sep. 30, 2013

Related U.S. Application Data

(63) Continuation-in-part of application No. 13/929,743, filed on Jun. 27, 2013, now abandoned.

(51) Int. Cl.
*G06Q 10/10* (2012.01)
*G06Q 50/00* (2012.01)
*G06F 19/00* (2011.01)

(52) U.S. Cl.
CPC ........... *G06Q 50/01* (2013.01); *G06F 19/322* (2013.01)

(58) Field of Classification Search
CPC .. G06Q 10/10; G06F 11/3438; G06F 11/3452
USPC ......................................................... 705/2–3
See application file for complete search history.

(56) References Cited

U.S. PATENT DOCUMENTS

| | | | | |
|---|---|---|---|---|
| 2008/0227063 | A1* | 9/2008 | Kenedy | G06Q 40/00 434/219 |
| 2009/0089630 | A1* | 4/2009 | Goldenberg | G06F 17/30536 714/704 |
| 2011/0071953 | A1* | 3/2011 | Shen | G06Q 30/02 705/319 |
| 2012/0290950 | A1* | 11/2012 | Rapaport | H04L 51/32 715/753 |

* cited by examiner

*Primary Examiner* — Joy Chng
(74) *Attorney, Agent, or Firm* — R. Kevin Perkins; Krishnendu Gupta

(57) ABSTRACT

A computer implemented method, system, and computer program product for capturing development and behavior of a social healthcare network in nodes and relationships of a social dataset, determining a sub-set of the social dataset for analysis, and performing an analysis on the sub-set.

20 Claims, 62 Drawing Sheets

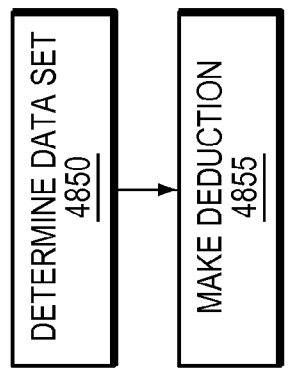
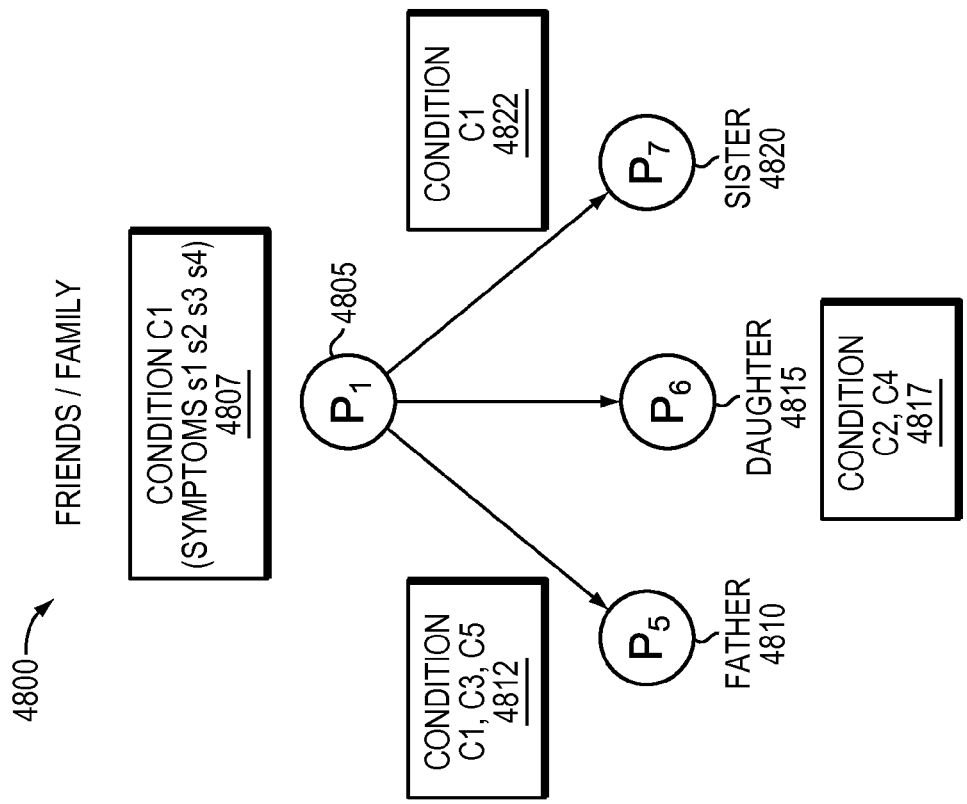
FIG. 48B
FIG. 48A

HEALTHBOOK ANALYSIS

RELATED APPLICATIONS

This application claims the benefit of priority of: U.S. patent application Ser. No. 13/929,743 entitled "HEALTHBOOK" filed Jun. 27, 2013 which is incorporated herein by reference for all purposes, which claims the priority of U.S. Patent Application Ser. No. 61/665,126 entitled "HEALTHBOOK" filed Jun. 27, 2012 which is incorporated herein by reference for all purposes.

A portion of the disclosure of this patent document may contain command formats and other computer language listings, all of which are subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

This invention relates to data storage.

BACKGROUND

The amount of data in our world has been exploding. Companies capture trillions of bytes of information about their customers, suppliers, and operations, and millions of networked sensors are being embedded in the physical world in devices such as mobile phones and automobiles, sensing, creating, and communicating data. Multimedia and individuals with smartphones and on social network sites will continue to fuel exponential growth. Yet, the impact this growing amount of data will have is unclear.

SUMMARY

A computer implemented method, system, and computer program product for capturing development and behavior of a social healthcare network in nodes and relationships of a social dataset, determining a sub-set of the social dataset for analysis, and performing an analysis on the sub-set.

BRIEF DESCRIPTION OF THE DRAWINGS

Objects, features, and advantages of embodiments disclosed herein may be better understood by referring to the following description in conjunction with the accompanying drawings. The drawings are not meant to limit the scope of the claims included herewith. For clarity, not every element may be labeled in every figure. The drawings are not necessarily to scale, emphasis instead being placed upon illustrating embodiments, principles, and concepts. Thus, features and advantages of the present disclosure will become more apparent from the following detailed description of exemplary embodiments thereof taken in conjunction with the accompanying drawings in which:

Figure 35:
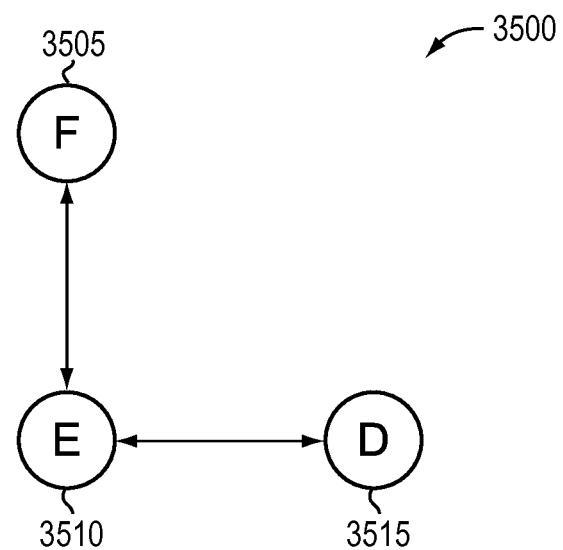
Figure 36:
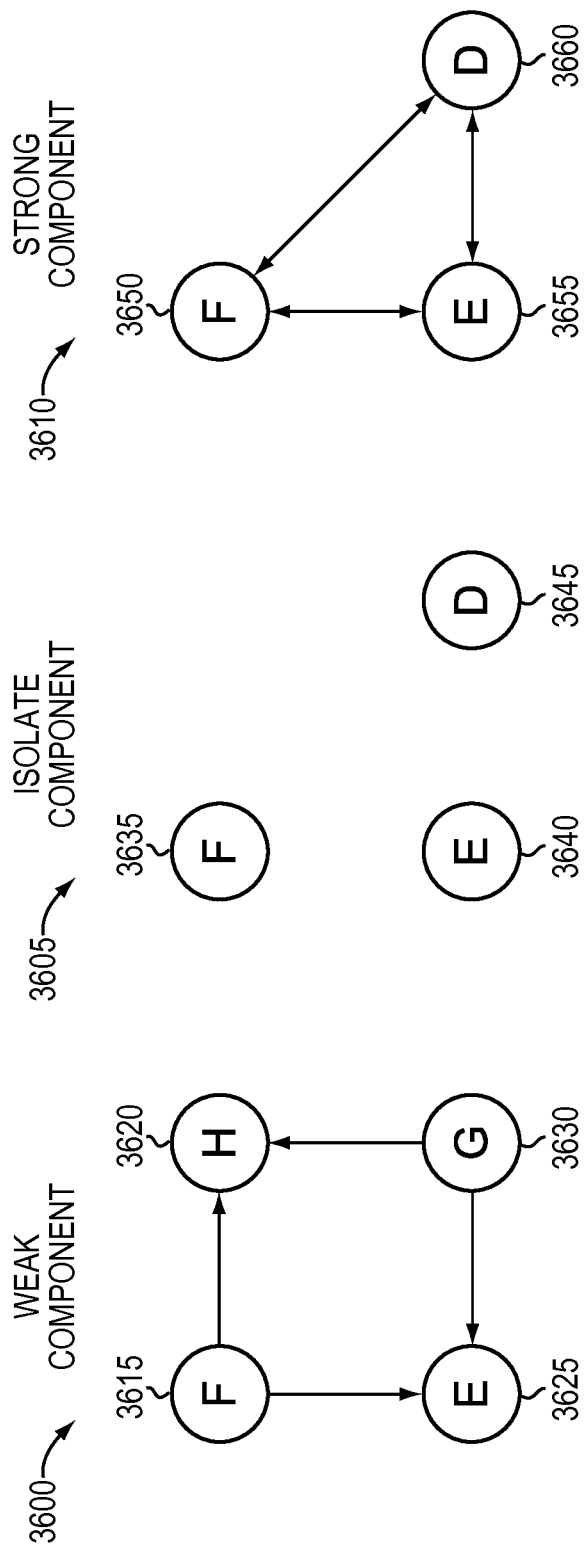
Figure 37:
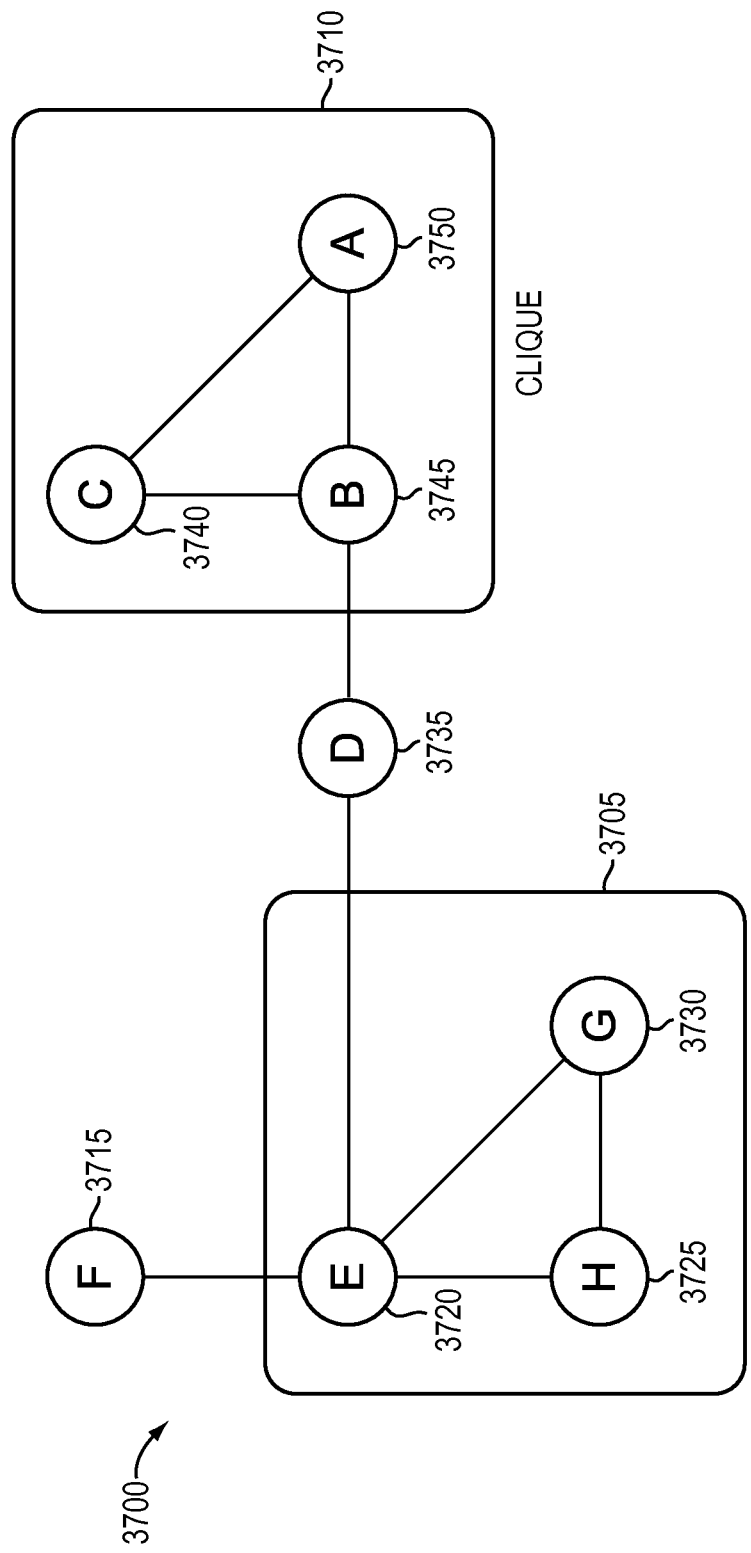
Figure 38:
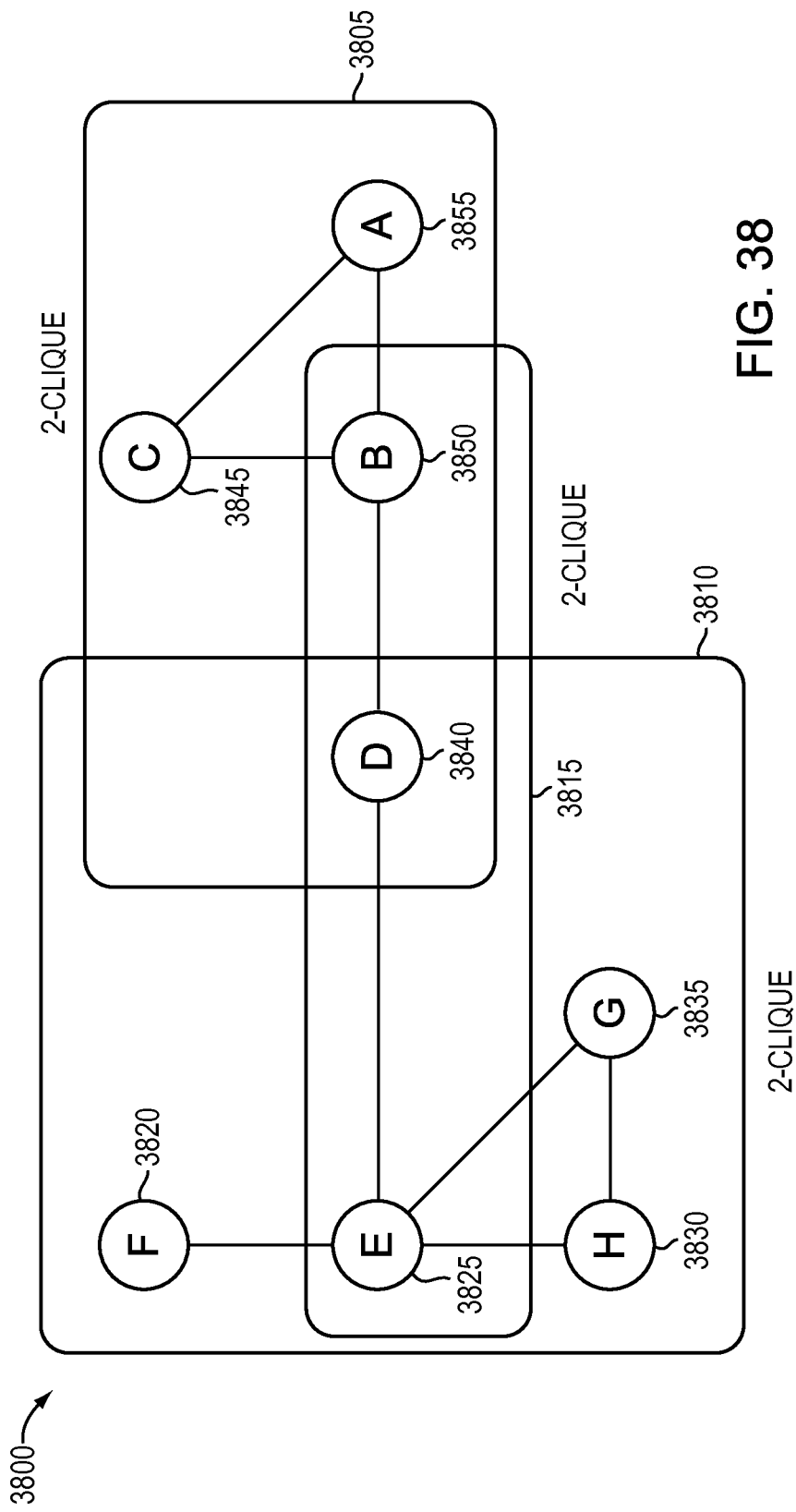
Figure 39:
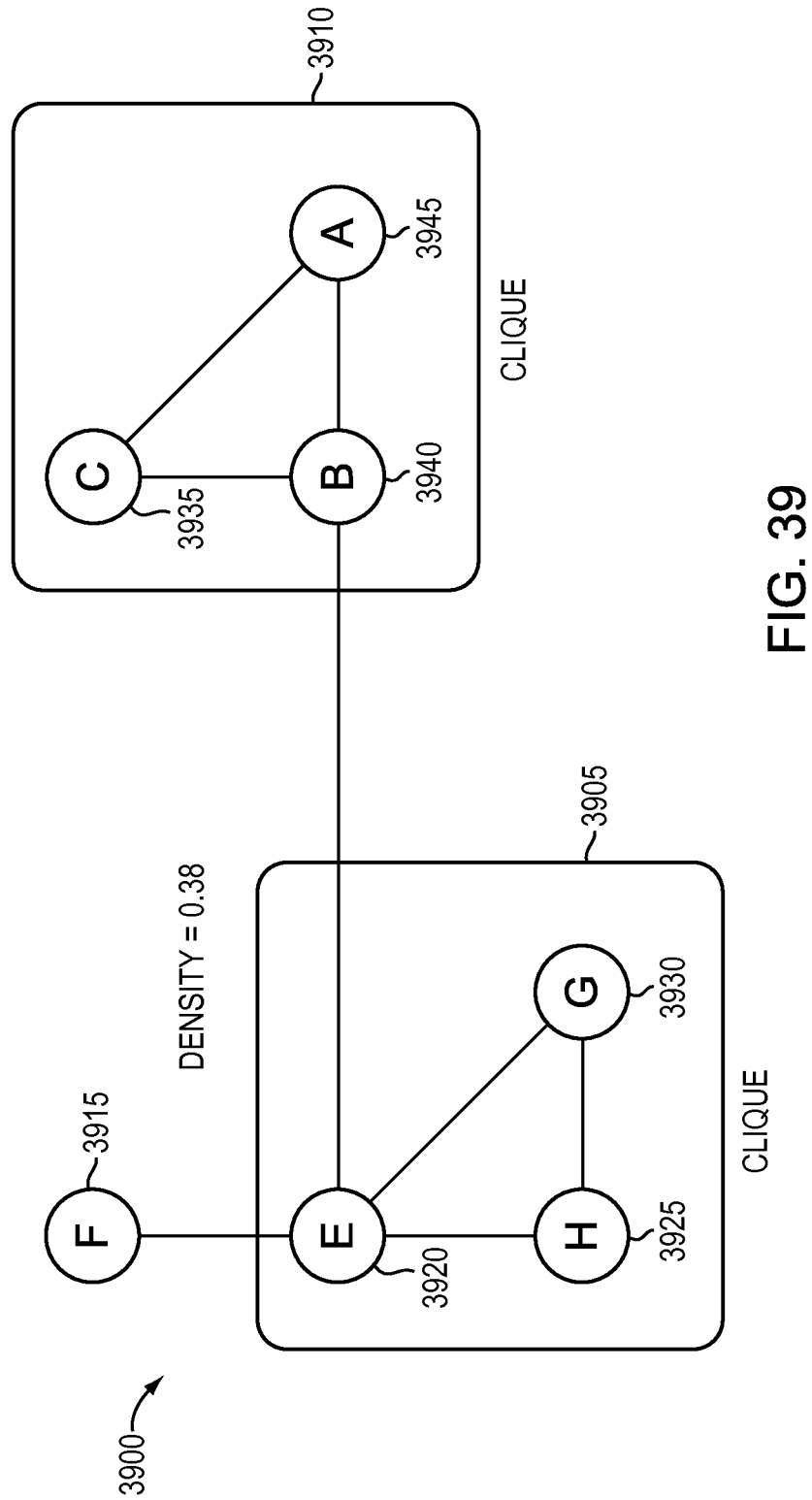
Figure 40:
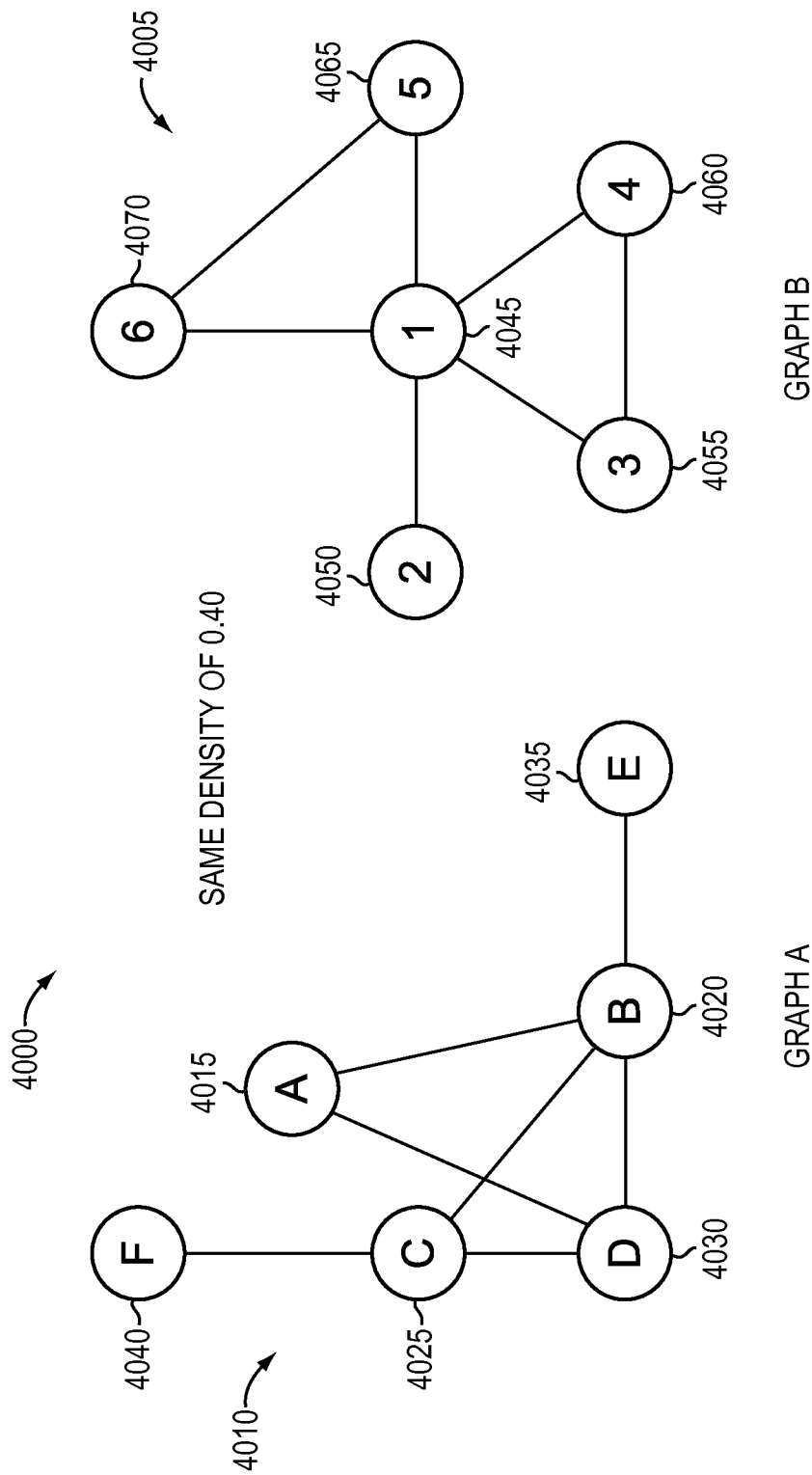
Figure 41:
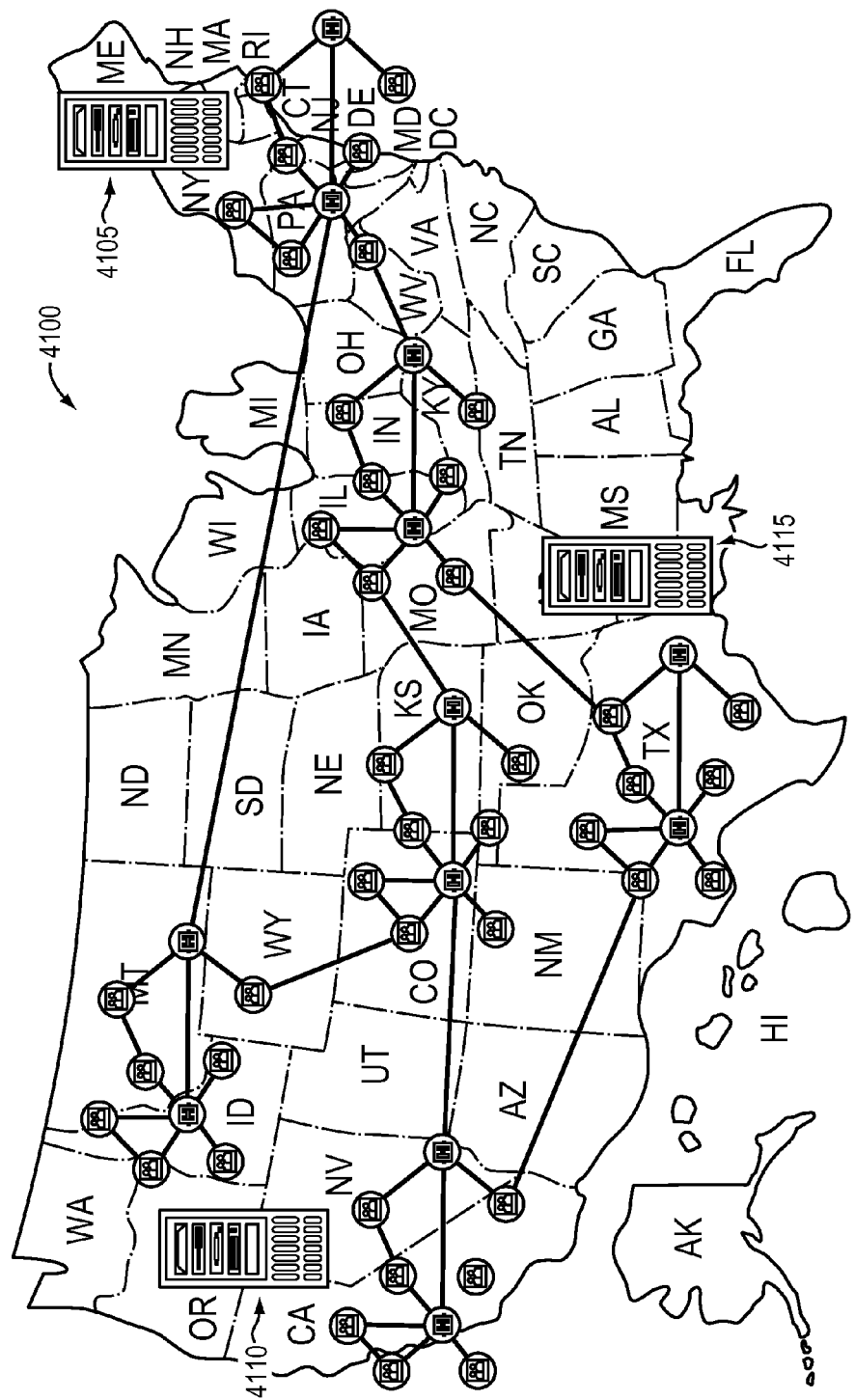
Figure 42:
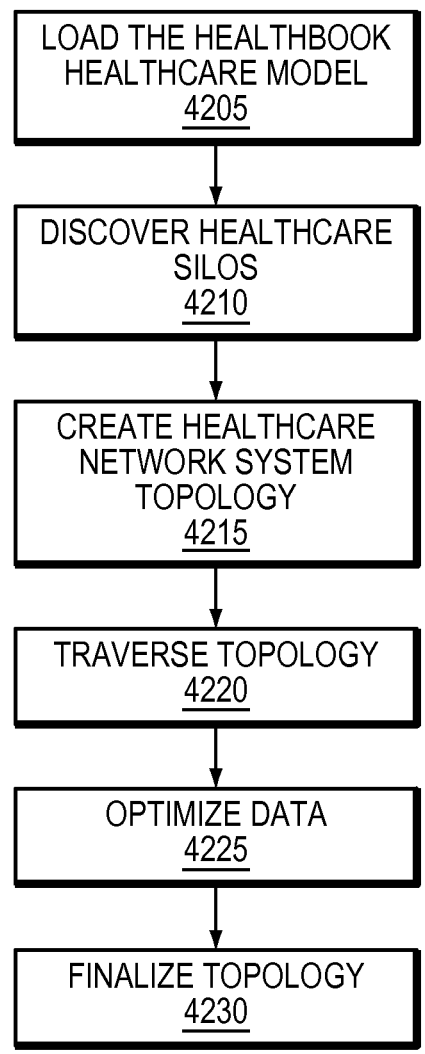
Figure 43:
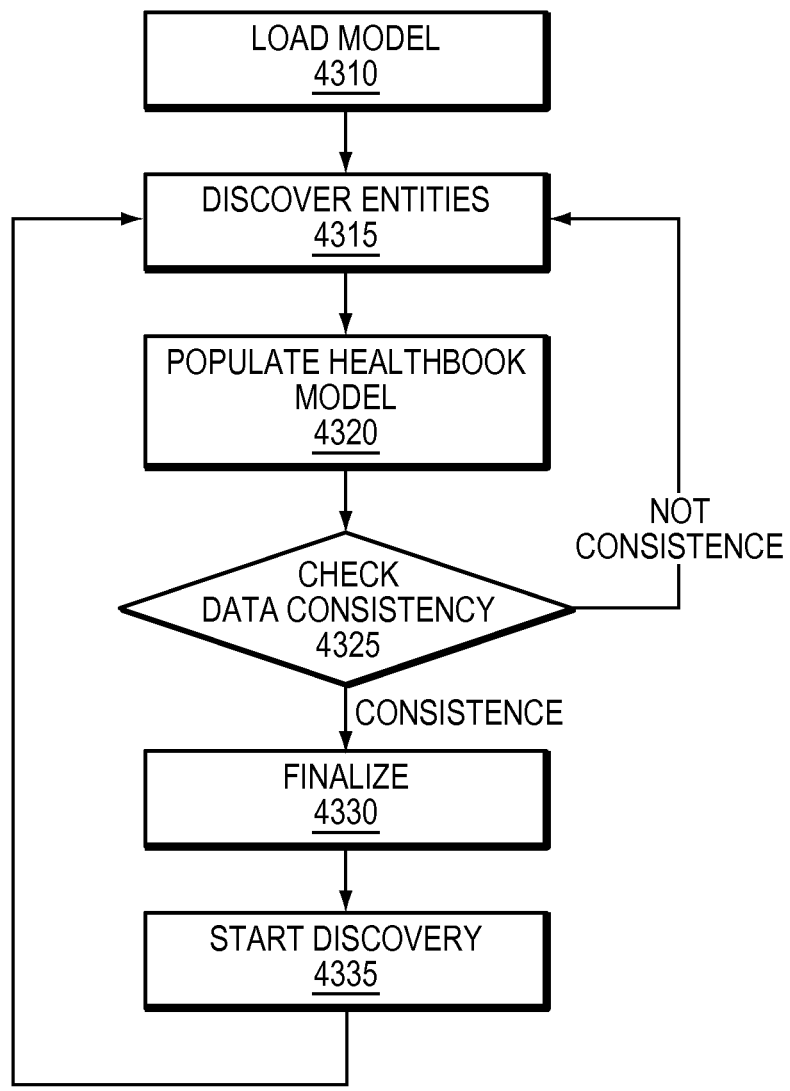
Figure 44:
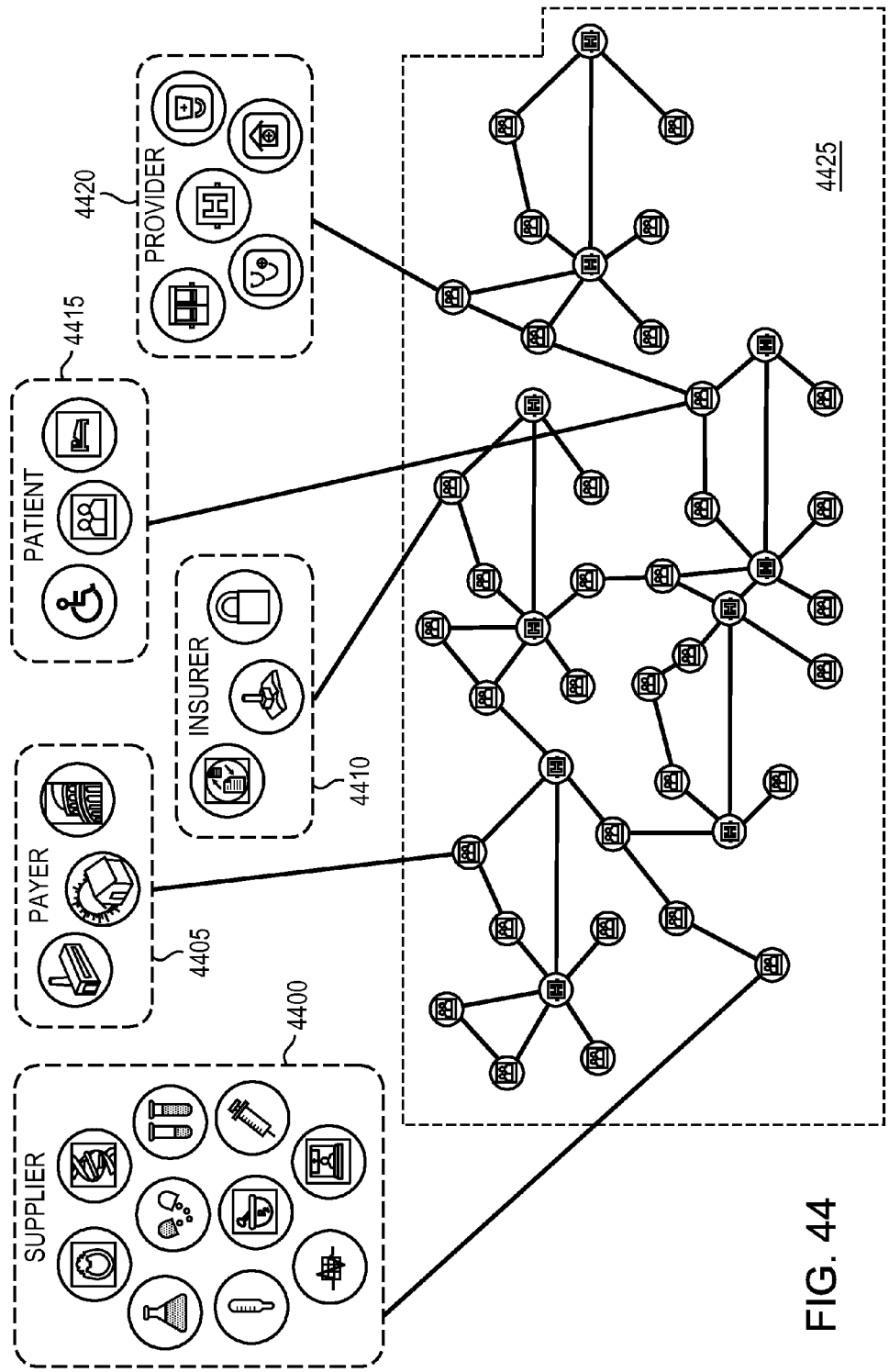
Figure 45:
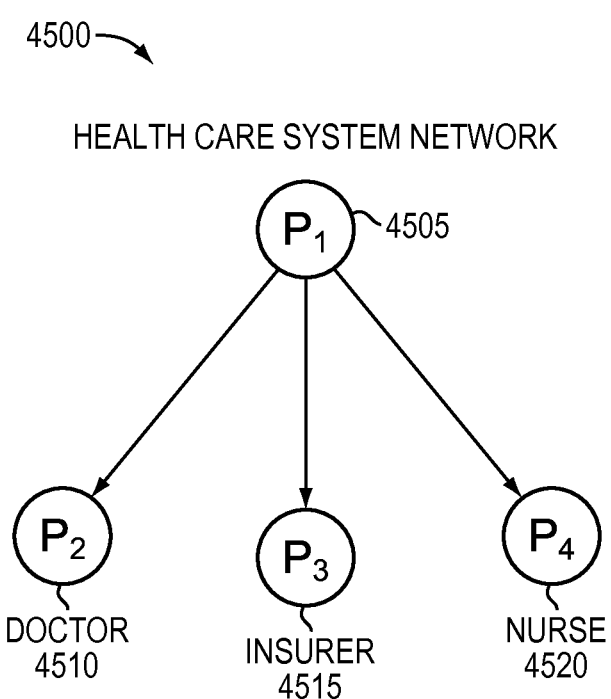
Figure 46B:
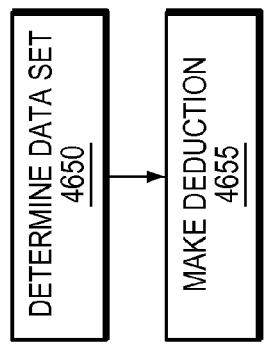
Figure 46A:
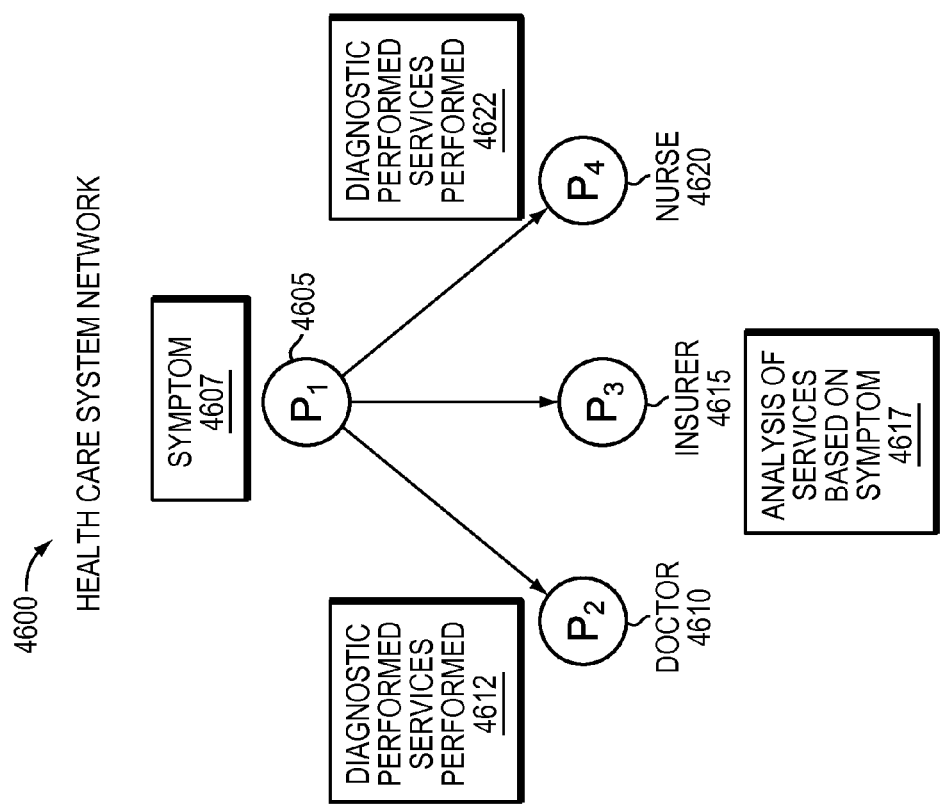
Figure 47:
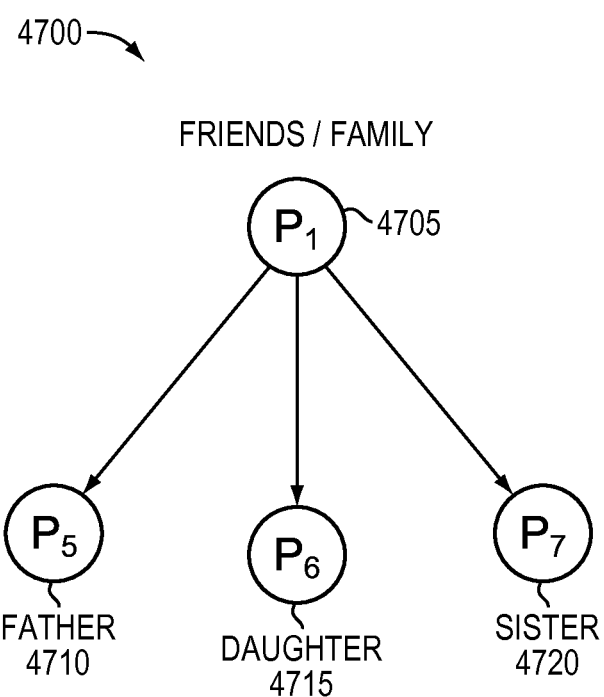
Figure 49:
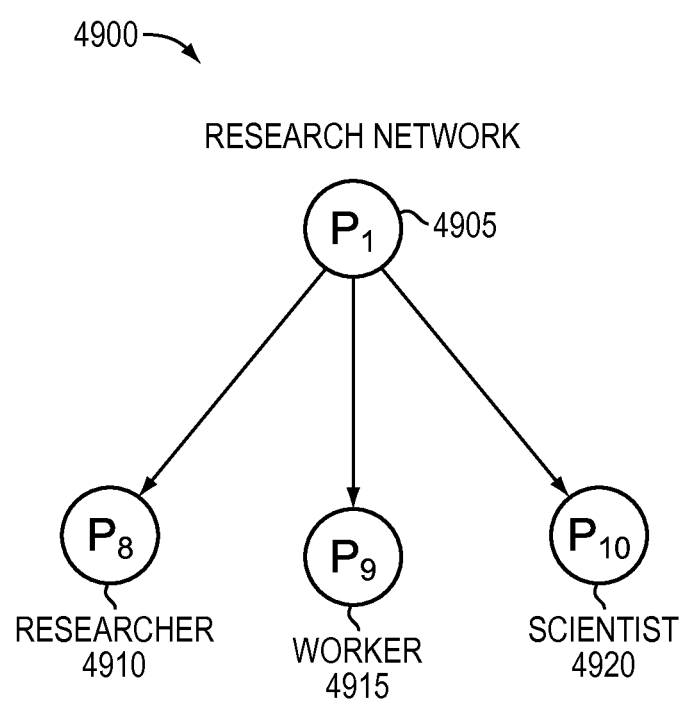
Figure 50B:
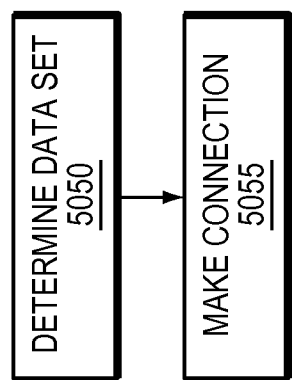
Figure 50A:
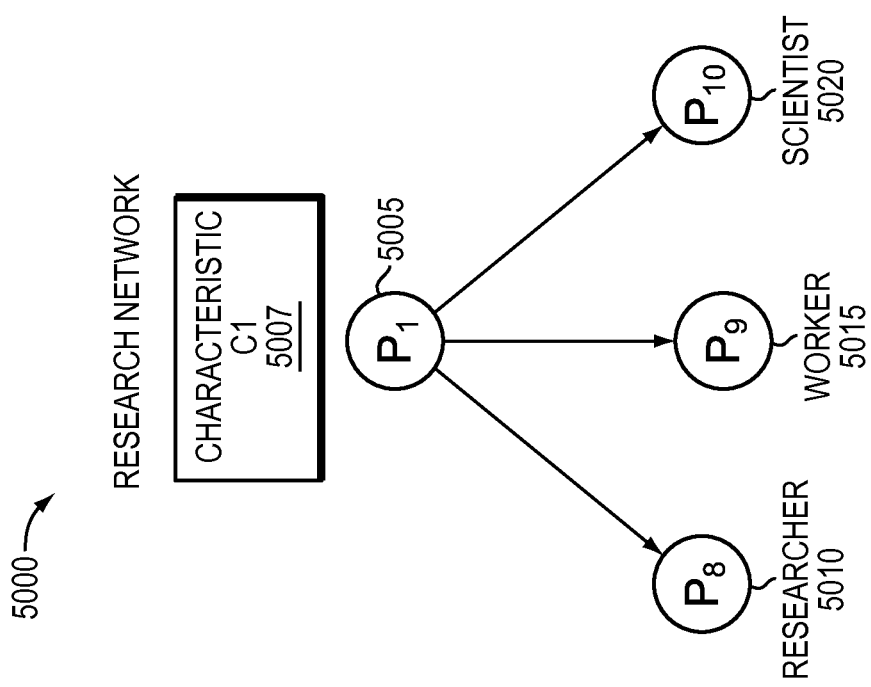
Figure 51:
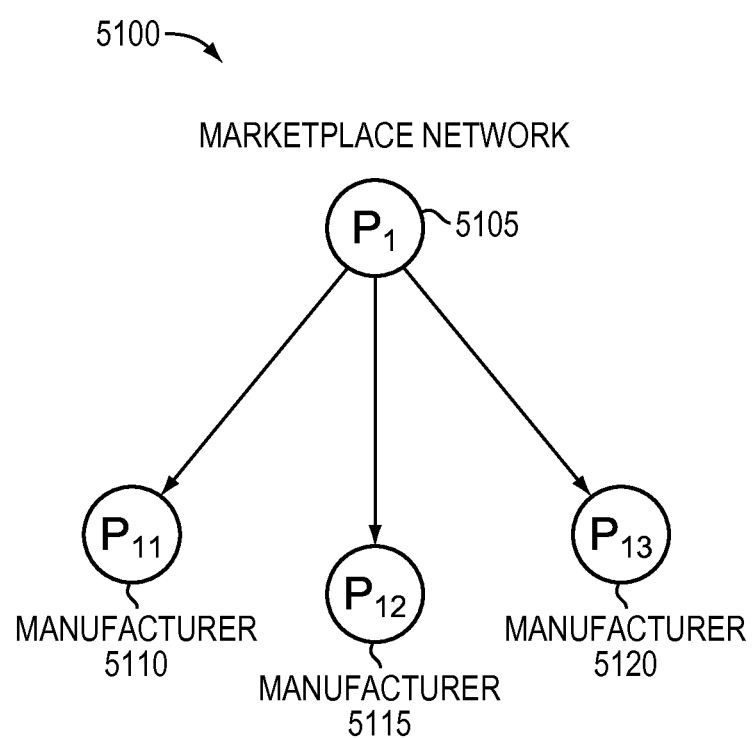
Figure 52B:
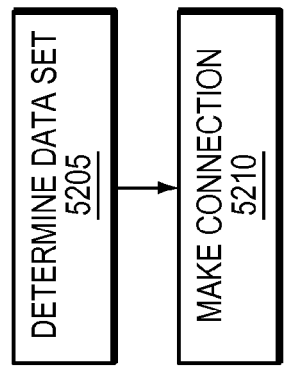
Figure 52A:
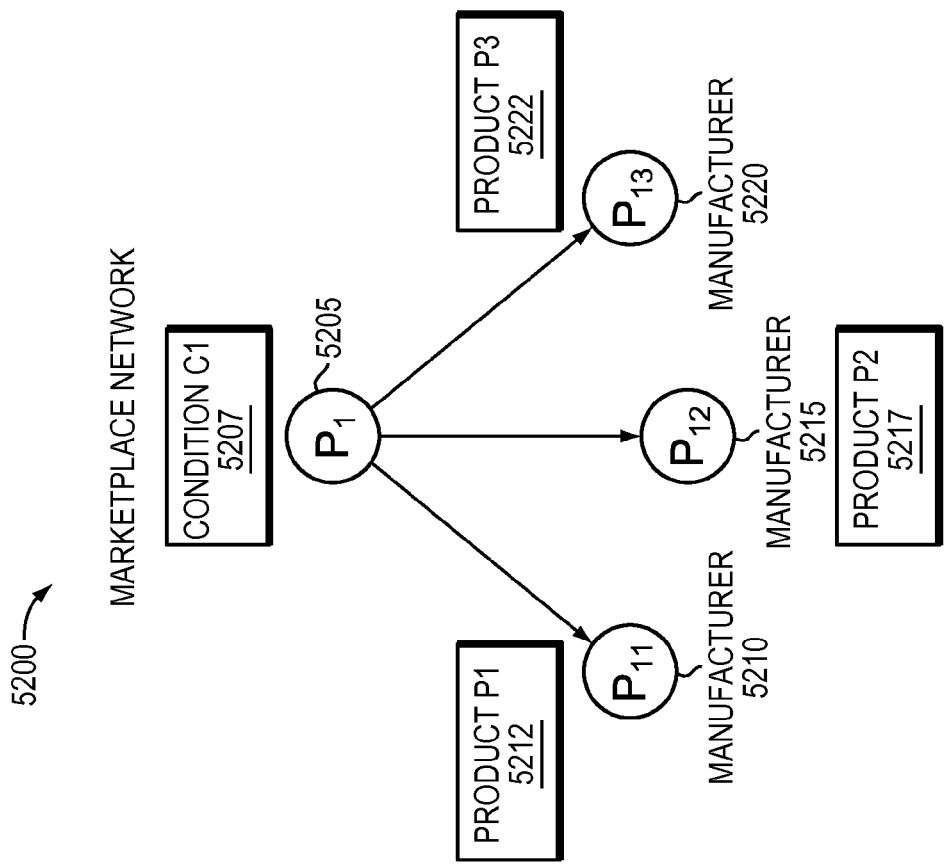
Figure 53:
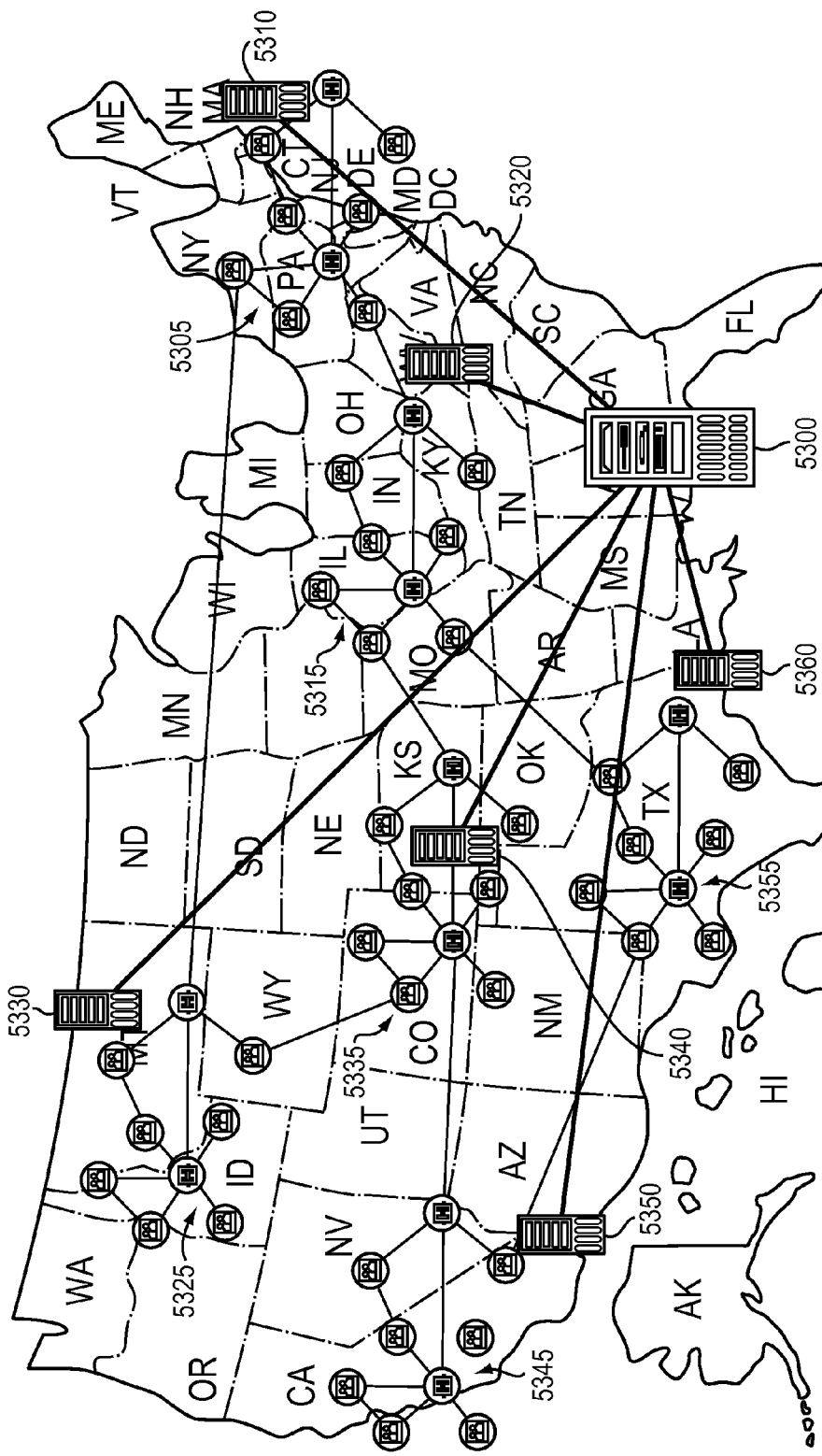
Figure 54:
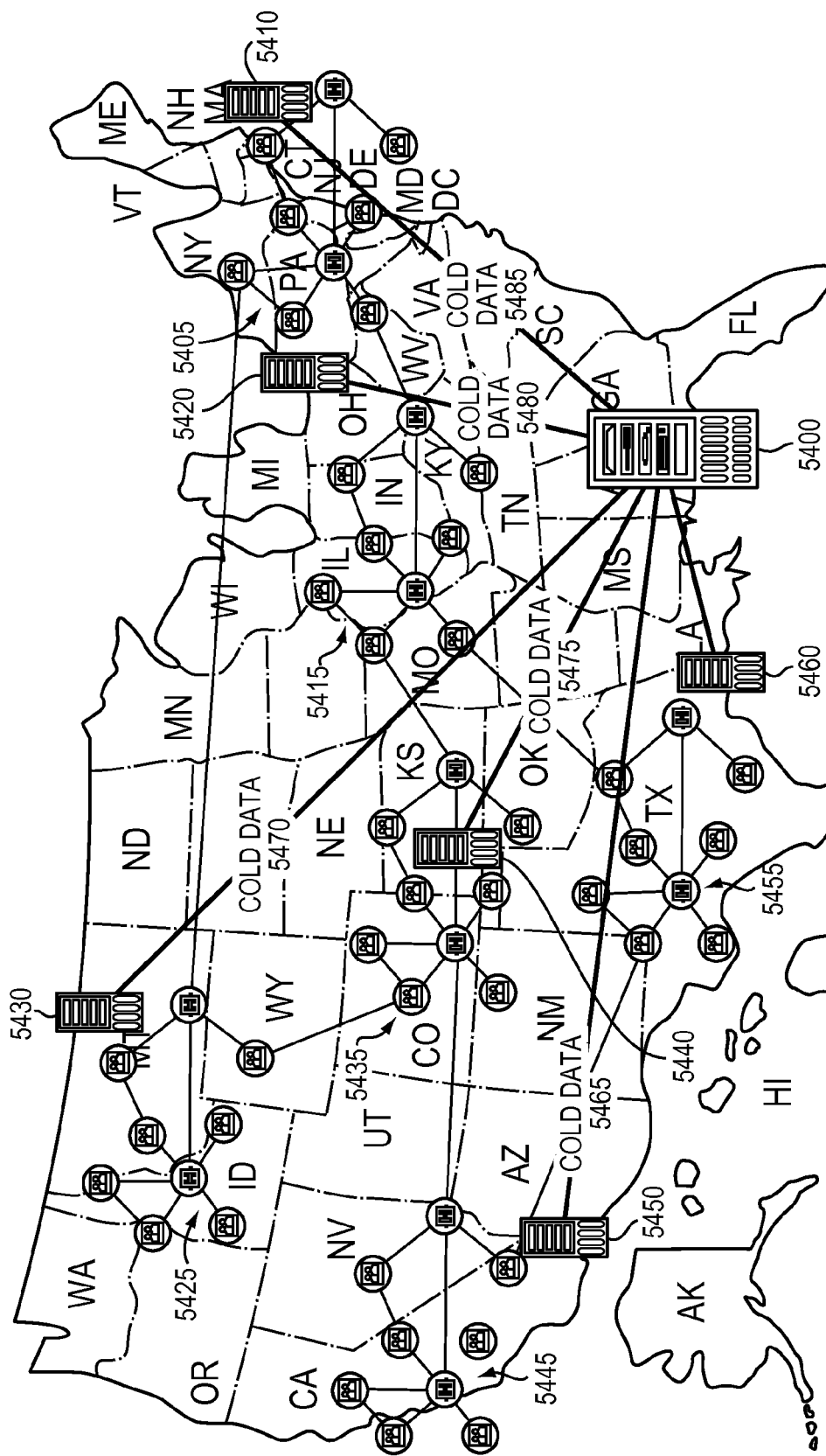
Figure 55:
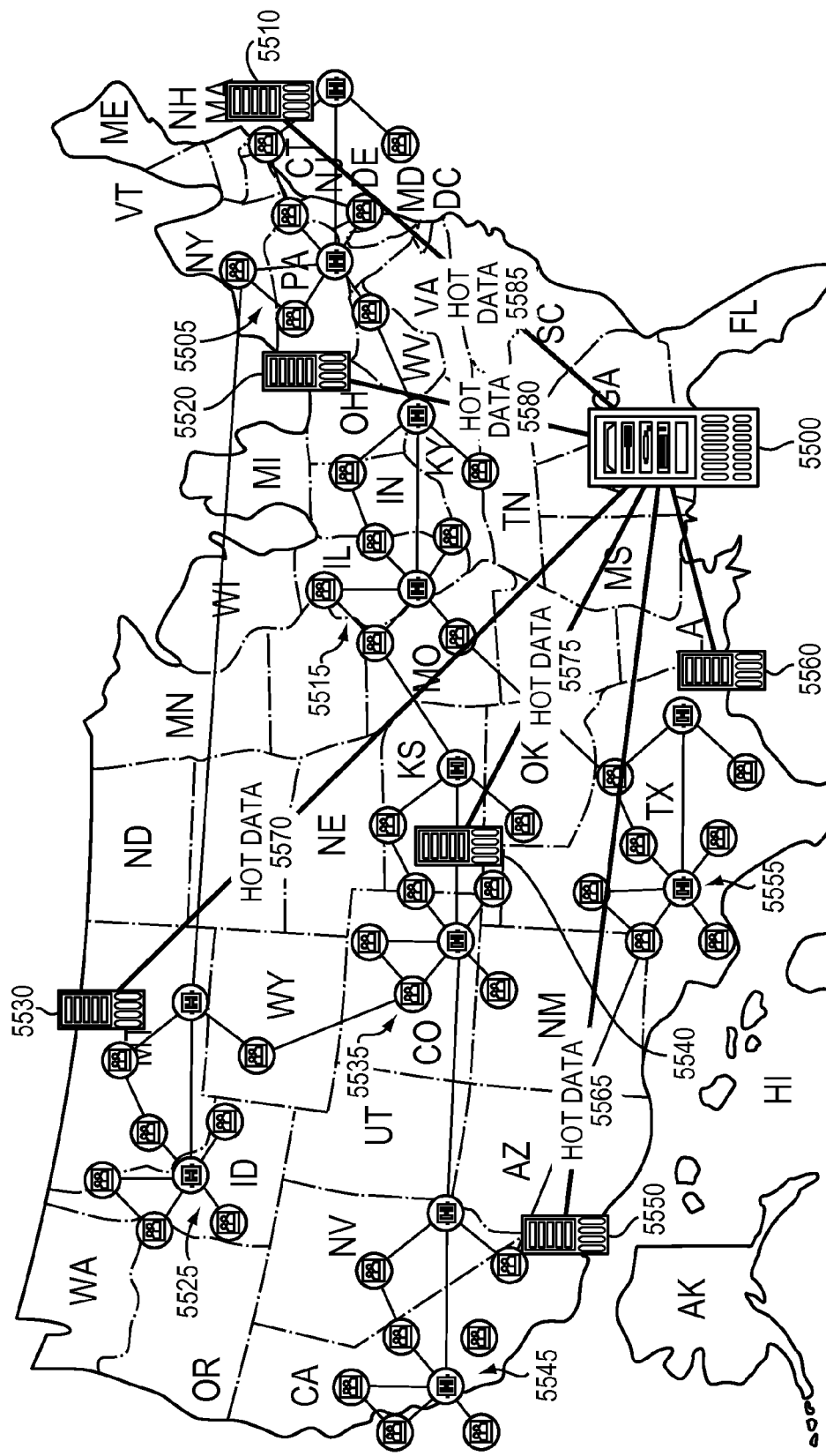
Figure 56:
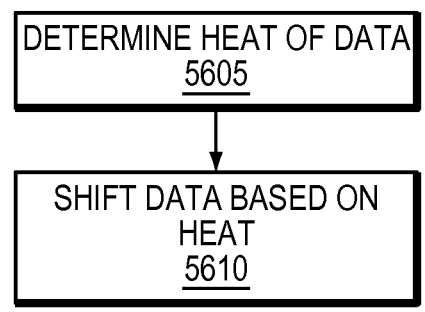
Figure 57A:
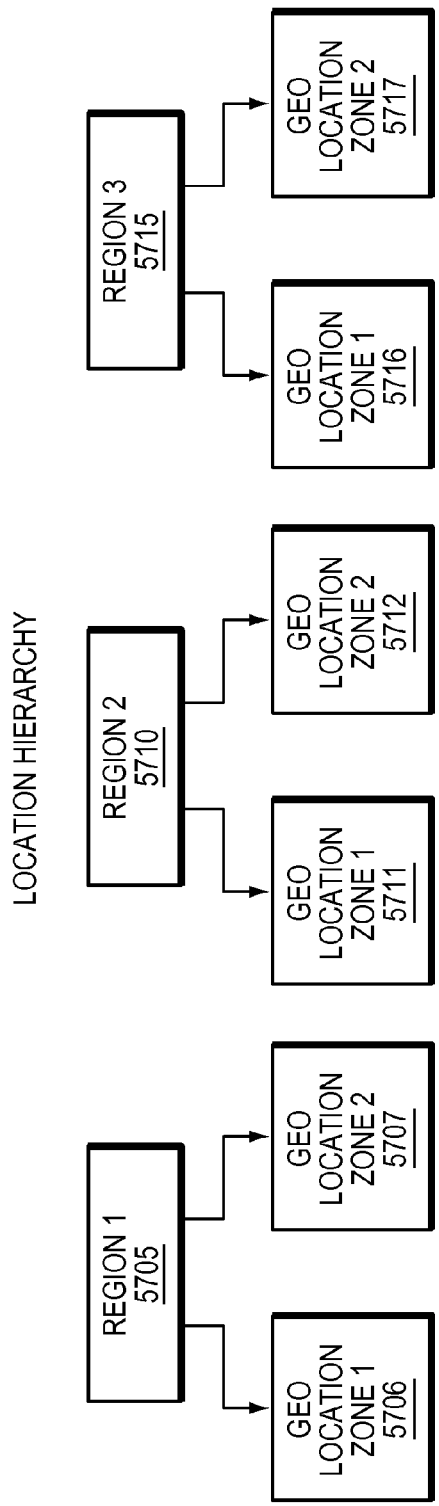
Figure 57B:
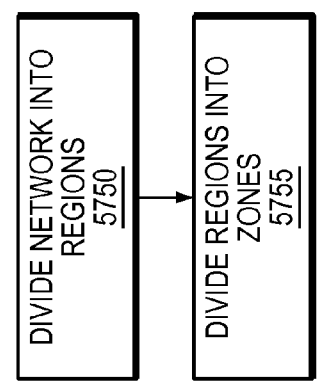
Figure 58:
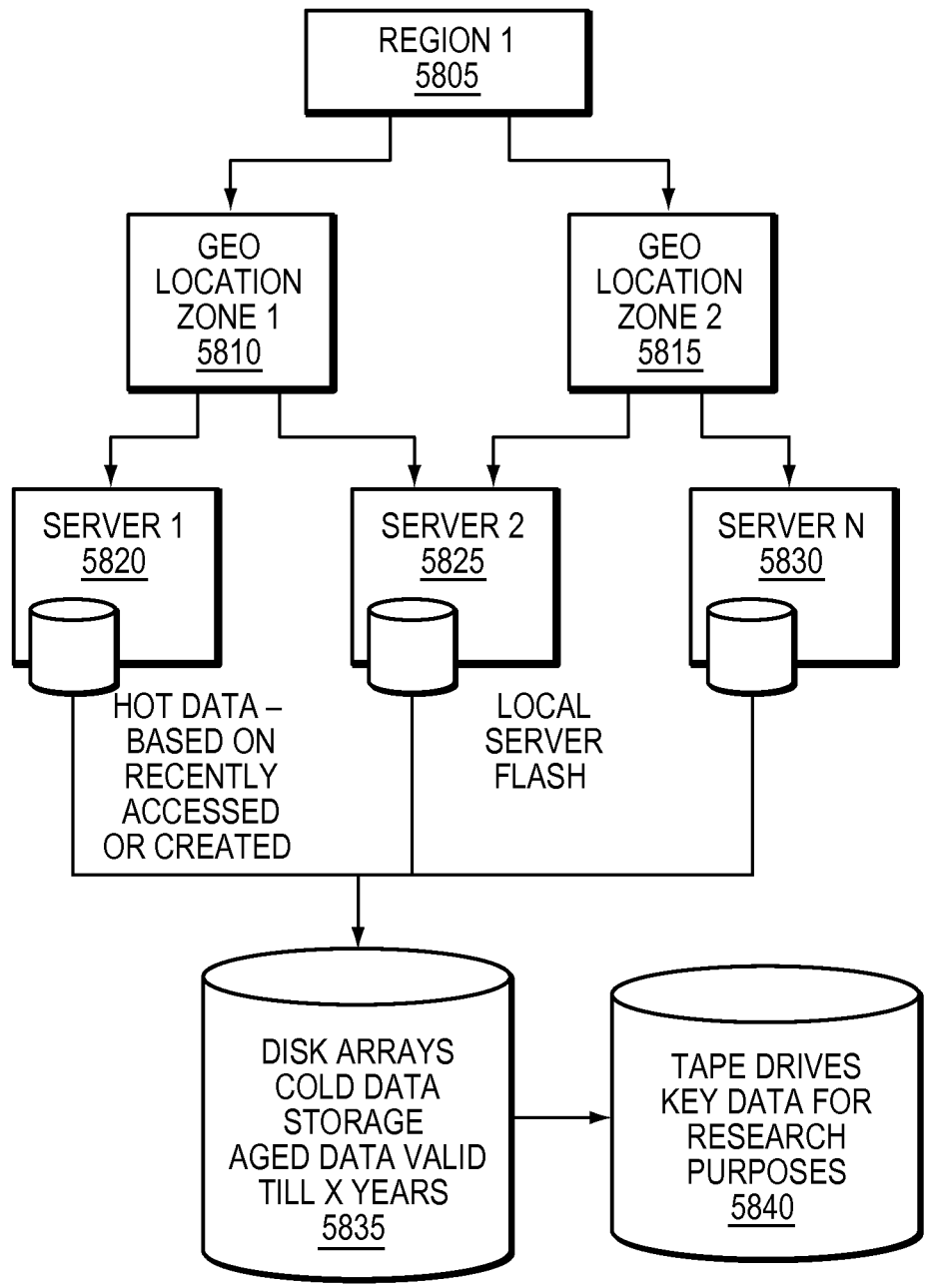
Figure 59:
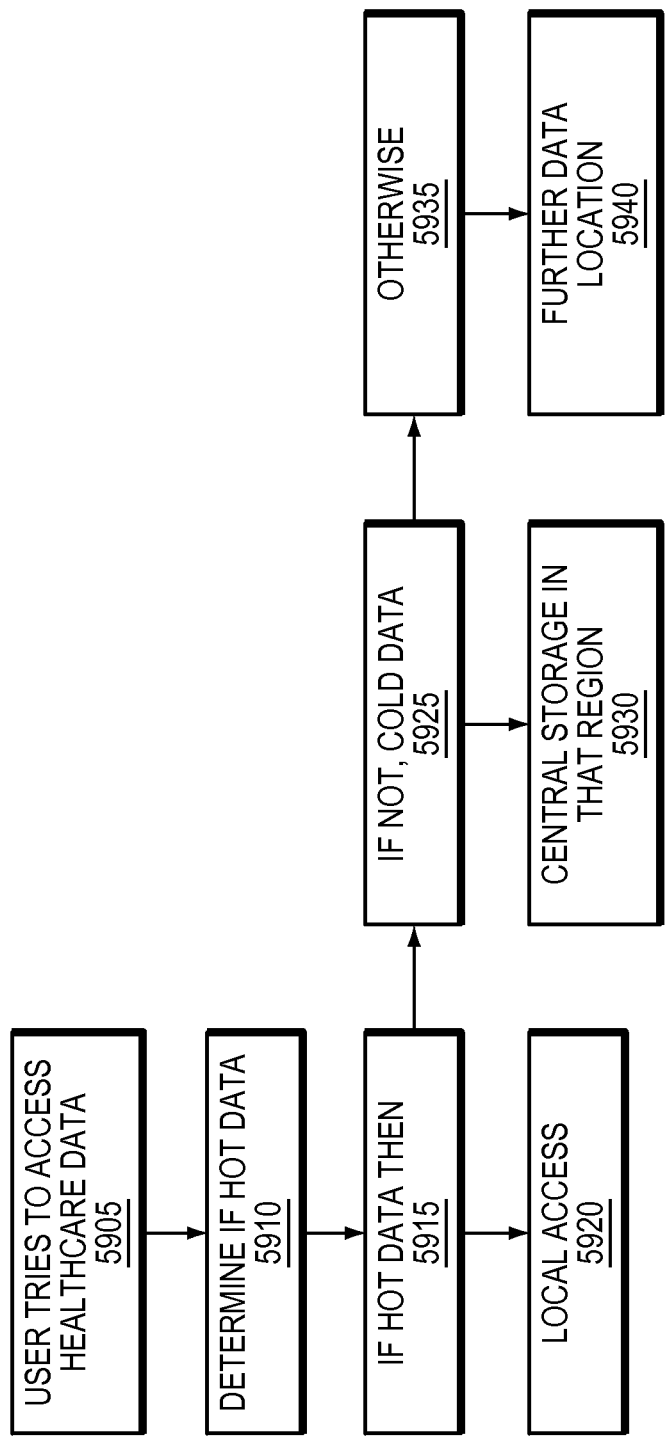
Figure 60:
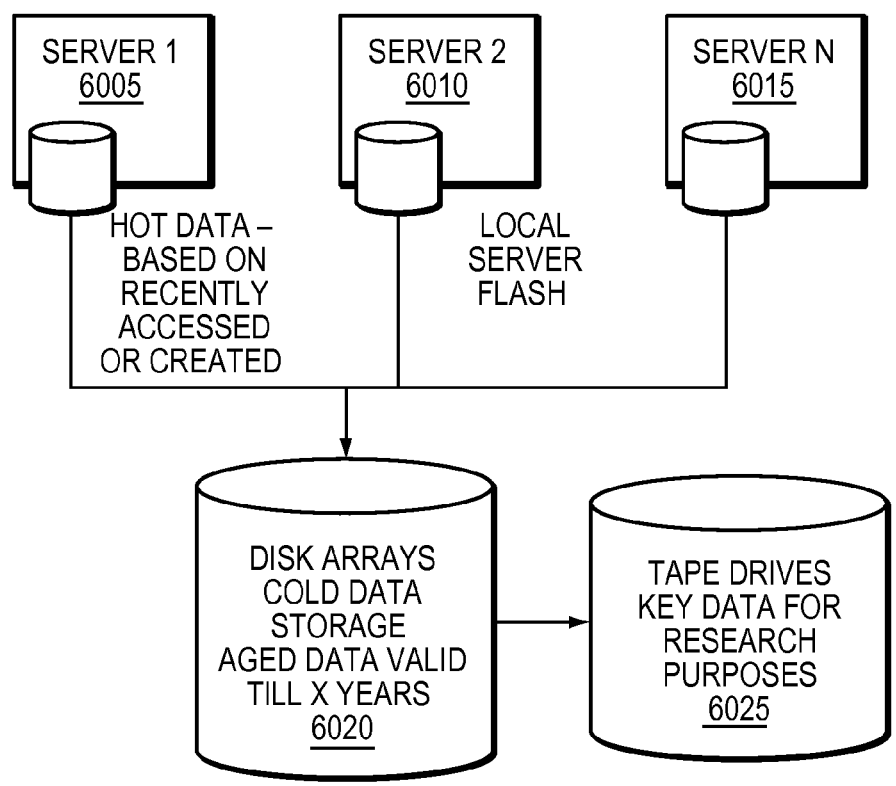
Figure 61:
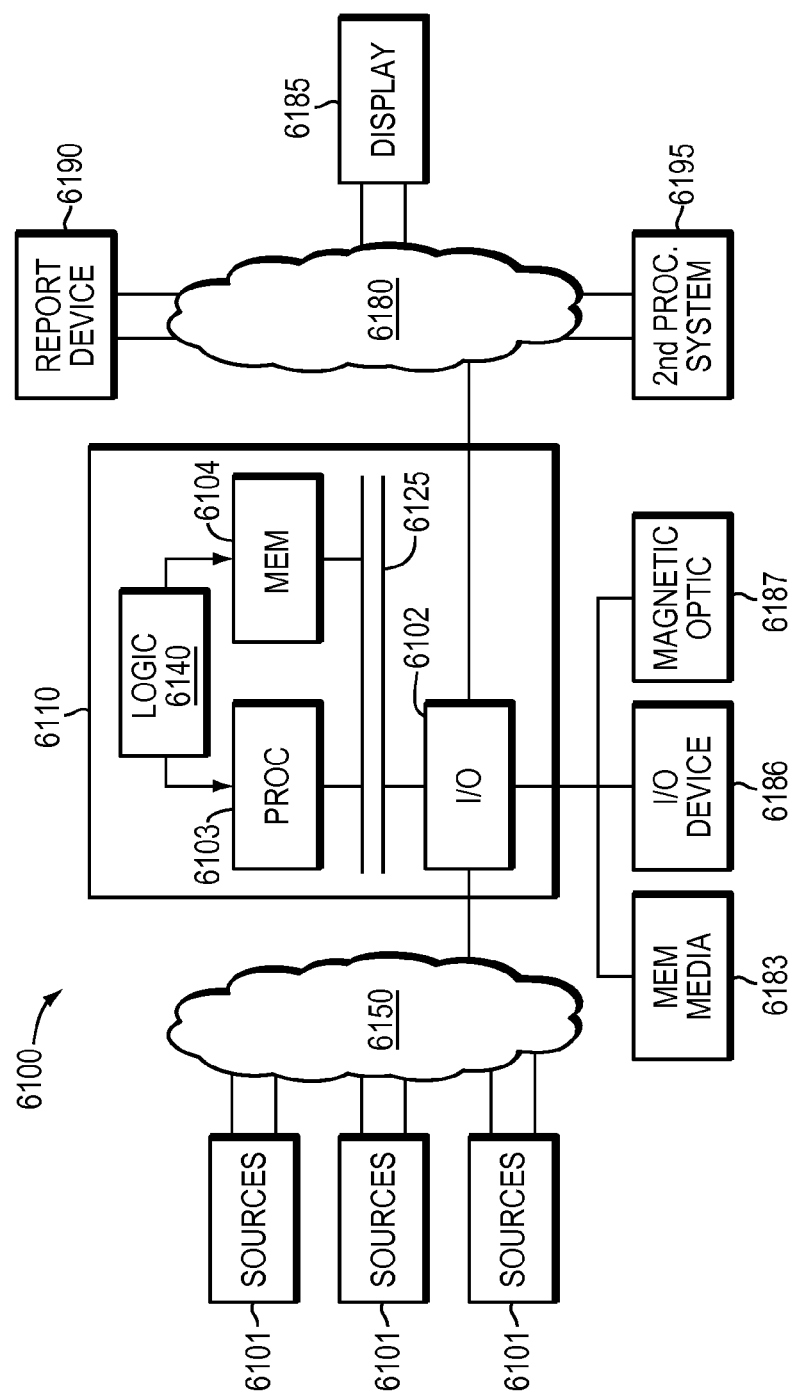
Figure 62:
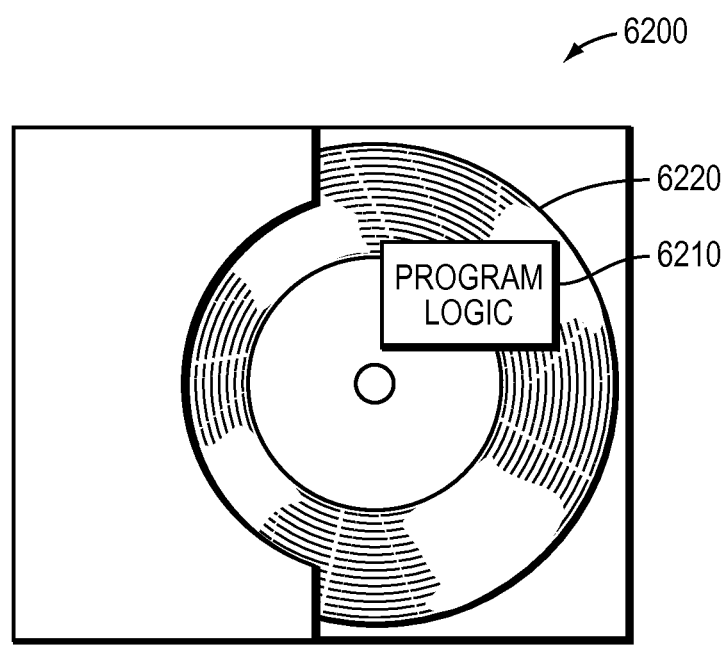

Refer now to the example embodiment of FIG. 35, which illustrates Forbidden triangle 3500, in accordance with an embodiment of the present disclosure;

FIG. 36 is a simplified illustration of a weak component, an isolated component, and a strong component, in accordance with an embodiment of the present disclosure;

FIG. 37 is a simplified illustration of two cliques, in accordance with an embodiment of the present disclosure;

FIG. 38 is a simplified illustration of 2-cliques, in accordance with an embodiment of the present disclosure;

FIG. 39 is a simplified illustration of a sample density for two cliques, in accordance with an embodiment of the present disclosure;

FIG. 40 is a simplified illustration of two networks of the same density, in accordance with an embodiment of the present disclosure;

FIG. 41 is a simplified illustration of co-locating data and processing power with network elements, in accordance with an embodiment of the present disclosure;

FIG. 42 is a simplified example of a method for building a health care model, in accordance with an embodiment of the present disclosure;

FIG. 43 is an simplified example of a method for validating a health care model, in accordance with an embodiment of the present disclosure;

FIG. 44 is a simplified example of a mapping health care players to a health care model, in accordance with an embodiment of the present disclosure;

FIG. 45 is a simplified example of a health care system network, in accordance with an embodiment of the present disclosure;

FIG. 46a is an alternative simplified example of a health care system network, in accordance with an embodiment of the present disclosure;

FIG. 46b is a simplified example for analysis in a health care system network, in accordance with an embodiment of the present disclosure;

FIG. 47 is a simplified example of a friends/family network, in accordance with an embodiment of the present disclosure;

FIG. 48a is an alternative simplified example of a friends/family network, in accordance with an embodiment of the present disclosure;

FIG. 48b is a simplified example for analysis in a friends/family network, in accordance with an embodiment of the present disclosure;

FIG. 49 is a simplified example of a research network, in accordance with an embodiment of the present disclosure;

FIG. 50a is an alternative simplified example of a research network, in accordance with an embodiment of the present disclosure;

FIG. 50b is a simplified example for analysis in a research network, in accordance with an embodiment of the present disclosure;

FIG. 51 is a simplified example of a marketplace network, in accordance with an embodiment of the present disclosure;

FIG. 52a is an alternative simplified example of a marketplace network, in accordance with an embodiment of the present disclosure;

FIG. 52b is an simplified example for analysis in a marketplace network, in accordance with an embodiment of the present disclosure;

FIG. 53 is a simplified example of a health network, in accordance with an embodiment of the present disclosure;

FIG. 54 is a simplified example of a moving cold data in a health network, in accordance with an embodiment of the present disclosure;

FIG. 55 is a simplified example of a moving hot data in a health network, in accordance with an embodiment of the present disclosure;

FIG. 56 is a simplified example of a method for moving data, in accordance with an embodiment of the present disclosure;

FIG. 57a is a simplified example of a location hierarchy, in accordance with an embodiment of the present disclosure;

FIG. 57b is an simplified example of a method for creating a location hierarchy, in accordance with an embodiment of the present disclosure;

FIG. 58 is a simplified example of a distributed storage architecture with a location specification, in accordance with an embodiment of the present disclosure;

FIG. 59 is a simplified example of a method for accessing data, in accordance with an embodiment of the present disclosure;

FIG. 60 is a simplified example a distributed storage architecture, in accordance with an embodiment of the present disclosure;

FIG. 61 is an example of an embodiment of an apparatus that may utilize the techniques described herein, in accordance with an embodiment of the present disclosure; and FIG. 62 is an example of a method embodied on a computer readable storage medium that may utilize the techniques described herein, in accordance with an embodiment of the present disclosure.

DETAILED DESCRIPTION

The following terms are employed throughout the specification and claims:

EDGE: may Or may Not Have Directionality. A directional edge E from a vertex A to a vertex B may Mean that Vertex A is related to vertex B as per edge E. Does not mean that Vertex B is related to vertex A; Vertex B may or may not be related to vertex A with a relationship of the same type as E. If vertex B is related to vertex A according to the same type of relationship, then a relationship may exist between B and A. If vertex B is NOT related to vertex A, according to the same type of relationship, then a relationship may not exist between B and A.

VERTEX: may Represent Different Types of Relationships between Edges

EDGE CONNECTS VERTICES: may indicate that an edge between two vertices demonstrates some type of relation between the connected vertices.

EDGE APPLIES TO VERTICES: may be another wording for EDGE CONNECTS VERTICES

NETWORK: may refer to the set of participants in the healthcare system. Network is not used here as in computer network or a physical network;

GRAPH: may be a Collection of vertex and edges

DI-GRAPH: may be a Collection of vertexes and directed edges

WALK: may be a sequence of nodes, where nodes are adjacent to each other

PATH: may be a walk where no node or line occurs more than once

SEMI-WALK: may be a walk which ignores the direction of arcs

SEMI-GRAPH: may be a graph which ignores the direction of arcs

WALK LENGTH: may be the number of edges that occur in a walk

ONE-MODE GRAPH: may be a graph in which nodes are of the same type; may study how nodes are tied to one another according to one relationship TWO-MODE GRAPH: may Consists of two types of nodes; may Study how nodes of one type are tied to nodes of another type STATE RELATION: may describe more enduring, more stable relationships EVENT RELATION: may describe more ephemeral relationships, that may exist during a certain period of time BOUNDARY: may Define a criteria that delimits a subset of the HN that will be analyzed, defining membership of the following elements within the boundary: Vertex, Edge, Properties. may define a subset of a HN, where elements within the subset comply with the boundary criteria SOCIAL NETWORK (SN): may be a set of nodes and relationships, where the relationships connect or apply to the nodes, and both the nodes and the relationships have properties HEALTH NETWORK (HN): may be A Social Network in the context of healthcare and life sciences, capturing the development and behavior of the social fabric of the system.

The Following Terms may Be Used Interchangeably herein Edges, arcs, lines, ties, relations, relationships, Vertices, nodes, and actors.

In some embodiments, the current disclose may enable multiple Personal Big Data Offerings. In other embodiments, cloud based, advertising supported business model, within the context of a Social Network may be enabled. In certain embodiments, as an alternative to a Classical Enterprise on premise offering, the current disclosure may enable value creation and retention shifting from Infrastructure providers, Application owners, Service Offering Sites and Data Custodians. In another embodiment, the current disclosure may enable a DigitalVault. In some embodiments, Big Data Storage may be readied as a Service for Personal Data. In a further embodiment, an application for sharing Healthcare Personal Data in a safe and privacy controlled environment may be enabled. In another embodiment, the current disclosure may enable personal data in the digital universe. In some embodiments, the current disclosure may enable capturing personal big data value. In other embodiments, the current disclosure may enable a Personal Big Data Market that may create and capture big data value. In further embodiments, personal data may drive value to application.

In some embodiments, the current disclosure may enable a DigitalVault platform for personal data. In other embodiments, the DigitalVault may enable data custody. In another embodiment, the DigitalVault may enable data custody which may ensure data privacy, may be complaint with Governance, Risk, and Compliance (GRC) restrictions, and may enable users to retain data ownership. In further embodiments, DigitalVault may provide comprehensive set of services. In some embodiments, DigitalVault may enable Back-up, Archive, and disaster recovery. In further embodiments, DigitalVault may enable compliance and performance reporting. In other embodiments, DigitalVault may enable embedded social network based analytics. In still further embodiments, DigitalVault may enable an ecosystem of application partner for data analysis.

In some embodiments, the current disclosure may enable a DigitalVault OS. In further embodiments, DigitalVault OS may enable complete certification program via OS. In still further embodiments, DigitalVault OS may enable application development environment for application partners.

In other embodiments, the current disclosure may enable a HealthBook. In another embodiment, Healthbook may create a safe market Place for the exchange of Healthcare data built on DigitalVault Platform. In further embodiments, a HealthBook may enable Data posted by consumer and providers, may enable Data automatically organized by application, or may enable Data accessed by authorized parties such as Insurance, payer, or provider. In another embodiment, Healthbook may build on Social Networking concepts. In some embodiments, Healthbook members may connect and share data. In further embodiment, Sponsors may have access to micro segmented market for marketing. In certain embodiments, Context sensitive services maybe offered such as doctor rating, medication recommendations and support groups. In other embodiments, Traffic may be driven from other social networks, such as Facebook. In still other embodiments, Healthbook may become a business platform in Healthcare market. In another embodiment, Healthbook may enable Open Science Advanced Data Analytics (OSADA). In some embodiments, OSADA may enable Census, Epidemic, Product Recalls, Labs and Genetic information for research. In yet another embodiment, OSADA Protects and de-couples personal private data. In some embodiments, HealthBook may enable a Personal Data Healthcare Network (PDHN). In further embodiments, PDHN may enable a membership fee paid by patients or physicians to post and access data, may enable a subscription fee paid by research institutions to access or analyze data, may enable an advertisement fee paid by pharmaceutical companies or retailers for target markets, or may enable agency fees, charged to application developers.

In other embodiments, Digital Vault may enable an Apps Market Place. In another embodiment, the Apps Market Place may enable application development fees or may enable training fees. In some embodiments, Digital Vault may enable Data storage. In further embodiments, DigitalVault may enable transfer fees, may enable storage fees, or may enable Service Fees, e.g. for backup, DR, High Available, GRC, or privacy.

In other embodiments, Healthbook may Carve out a portion of Smart PHR application functionality for pilot, may Create a pilot to introduce Social Networking to an application, or may Create Partnerships with one or more Healthcare Companies to build an application.

In further embodiments, the current disclosure may enable a simplified Big Data architecture. In some embodiments, the current disclosure may enable Value to Network Nodes. In certain embodiments, the current disclosure may enable Goods and Services Ratings, Exchange, Search, Experience, Credence, or Providers may achieve 1st degree Price Discrimination. In still further embodiments, the current disclosure may enable data sources or types in the Digital Universe. In further embodiments, Personal Data in the digital universe may be private, Such as email id on YouTube. In other embodiments, Personal Data in the digital universe may be Compliance, or Subjected to retention and rules, such as income tax. In certain embodiments, Personal Data in the digital universe may be Custodial, Such as account information. In some embodiments, Personal Data in the digital universe may be Confidential, Such as customer list or trade secrets. In still other embodiments, Personal Data in the digital universe may be Lockdown, Such as financial transactions or medical records.

In some embodiments, applications may determine underlying big data infrastructure. In another embodiment, personal data may drive value to application and infrastructure. In further embodiments, economies of networks may provide increased value to the network nodes. In still further embodiments, the current disclosure may enable NanoData. In certain embodiments, the current disclosure may enable NanoData for data privacy. In other embodiments, "nanodata" or customized fine-grained data may describe in detail the characteristics of individuals, transactions, or information flows. In another embodiment, the current disclosure may enable NanoData Networks. In other embodiments, the NanoData may enable Network Externalities. In some embodiments, Economies of Networks with nanodata may provide Privacy or Increased Value. In further embodiments, the current disclosure may Capture Personal Data and nanodata Value by "DigitalVault" offering. In another embodiments, the current disclosure may Capture personal big data economies of network value by offering applications.

In further embodiments, the current disclosure may enable HealthBook-like applications. In certain embodiments, the current disclosure may enable monthly subscriptions. In some embodiments, the current disclosure may enable Business and Network creation services and fees, Advertisements, Coupons, or Analytics and Reports Fees. In other embodiments, DigitalVault may enable Service Charges to Applications, Data In/Out Transfer fees, or Backup and Privacy service charges. In further embodiments, the current disclosure may enable partners to Sell IT to DigitalVault, Sell Analytics platform to Applications, or Sell Consultancy and Services to both DigitalVault and Applications.

In some embodiments, Healthcare may be at the intersection of Big Data, Cloud and Trust. In some embodiments, Forces shaping healthcare may be Social, Big Data, Mobile and Cloud, or may have a Facebook like personal data application requirement. In some embodiments, Forces that may shape Healthcare may be Cloud, Open, Mobile, BigData, or Social. In other embodiments, Cloud may comprise Hospitals, Consumer and Insurance using cloud Data Store & Services, Open may comprise Open Science Data and Standards and Software, Mobile may comprise Healthcare industry transitioned to use iPads and smart phones, BigData may comprise Images, Records, Transactions and Claims, and Social may comprise Communities such as Weight Watchers, or Progress info sharing. In another embodiment, the current disclosure may enable interoperability. In other embodiments, Healthcare Big Data Cloud IT may be determined by Healthbook like application. In some embodiments, Big data and cloud architecture may look more like Facebook's than that of a classic enterprise.

In certain embodiments, Healthcare applications and their owners may determine architecture. In some embodiments, the current disclosure may enable Analytics, Virtualization, Storage, or Security. In another embodiment, an Application may not own entire stack.

In some Embodiments, the current disclosure may address verticals, markets and geographies. In other embodiments, the current disclosure may build infrastructure for enterprise IT. In some embodiments, the current disclosure may meet the architectural needs of classic data center, may capture revenue from mature infrastructure markets, or may largely ignore application and vertical market differences.

In certain embodiments, the current disclosure may capture Healthcare value. In some embodiments, the current disclosure may horizontally address the current market requirements. In further embodiments, Application vendors may make applications, or Infrastructure vendors may make infrastructure. In other embodiments, the current disclosure may Qualify and certify applications and infrastructure. In some embodiments, Arms length relationship (e-lab) may ensure good citizenship within the application's environment.

In other embodiments, the current disclosure may enter application space to define underlying components. In further embodiments, the current disclosure may capture huge profit pie from the top of value chain. In some embodiments, the current disclosure may Enter and control emerging big data application market. In certain embodiments, the current disclosure may provide infrastructure to world of Facebook's like applications. In other embodiments, the current disclosure may Play a leading role in the application and infrastructure space, or may Determine and control the underlying infrastructure and architecture.

In some embodiments, the current disclosure may enable healthcare application and infrastructure products. In other embodiments, the current disclosure may enable partners to buy healthcare application and infrastructure products. In some embodiments, the current disclosure may enable partners to create healthcare value chain and control infrastructure architecture. In certain embodiments, the current disclosure may enable partners to make, buy, and partner.

In some embodiments, the current disclosure may enable parties to Research and create the required cost efficient architecture and infrastructure, may enable parties to Build data center and application prototypes, or may enable parties to Form Coalition of healthcare IT, Pharma, and Insurance business and channels. In some embodiments, applications may determine infrastructure.

In other embodiments, the current disclosure may enable Social, Cloud and Mobile internet designs and user interfaces. In certain embodiments, the current disclosure may enable management of Personal Health Record (PHR). In some embodiments, PHR may be a health record where health data and information related to the care of a patient is entered by the patient. In further embodiments, the current disclosure may enable Healthcare Circles. In another embodiment, Healthcare Circles may be a Group that share relevant and interesting data. In some embodiments, circle members may share data using Avatars masking true identity. In further embodiments, HealthCare Circles may have sponsors. In a certain embodiment, Sponsors may create business platforms and channels on circle. In other embodiments, sponsors may create a circle and invite people, may post advertisements, or may perform data analytics on circles. In further embodiments, user data may be anonymized, user data may be stored in a graph type object, node strength may be applied to nodes, or diagnosis may be made by mining data. In other embodiments, the current disclosure may cross reference symptoms treatments, may cross reference results of treatments, may provide "pseudo" studies based on breath of the data, may enable increased confidence by reducing error through the large sample size, may enable doctor's to examine data, may enable doctor's to examine data profiles, or may enable doctor's to examine mined data to make further extrapolations and diagnosis.

In some embodiments, the current disclosure may enable Open Science Data. In further embodiments, Open Science Data may enable Transparency in experimental methodology, observation, and collection of data may enable Public availability and reusability of scientific data, may enable Public accessibility and transparency of scientific communication, and may enable using web-based tools to facilitate scientific collaboration. In other embodiments, Open Science Data may comprise Calories, BMIs or other standards. In some embodiments, Open Science Data may comprise Protein, Vitamin, Supplements Data, Flu, Epidemic, outbreak information, Vaccination schedules, or Genome Information. In another embodiment, Open Science Data may be published by Scientists, Biotechs and Govt. In further embodiments, Open Science Data context with PHR and circle may be a valuable control point.

In certain embodiments, Healthbook may be a secure private book for healthcare. In some embodiments, HealthBook may enable Consumer and care providers to post or store health records. In other embodiments, Healthbook may organize data with timeline. In further embodiments HealthBook may enable Access to personal health information, anytime, anywhere, any device, any doctor, any insurance, any care provider like a social networking service. In some embodiments, Healthbook may build on social and mobile networking concepts such as circles and sponsors. In other embodiments, Healthbook circle members may store and share data and may connect with people. In certain embodiments, HealthBooks may be a business platform to businesses. In some embodiments, HealthBook may be a Platform to post coupons, advertisements, doctor ratings, prescriptions, drug ingredients etc. In further embodiments, HealthBook may automatically drive consumers from facebook and other social networks into healthbook. In certain embodiments, Healthbook may provide open science data and analytics. In still further embodiments, HealthBook may enable in context Census, Epidemic, Product Recalls, Labs and Genetic information to research community. In some embodiments, Healthbook circle may protect and de-couples personal privacy and open data.

In some embodiments, Greenplum Hadoop Distribution may enable census and analytics. In other embodiments, Isilon Hadoop Distribution may enable scale out. In certain embodiments, EMC-SP/NGDC Architecture and Principles, and POD concepts may help to design the data center blueprints.

In other embodiments, Healthbooks may improve quality of life at affordable costs. In other embodiments, HealthBook may provide personal book to organize health data, or may have consumer controlled personal health data management cloud, web and mobile apps.

In some embodiments, HealthBook may enable Consumer to have one place for heath records, communication, coupons, more information such as ratings and lower cost services. In other embodiments, HealthBook may enable Diagnostic Lab to have one place to upload lab results. Connections and marketing with doctors and hospitals. In further embodiments, HealthBook may enable Healthcare Providers (Doctors, Hospitals, Wellness Centers) to have Business and Network Creation: Ratings, Marketing, Customer Acquisition. In other embodiments, HealthBook may enable Pharmaceuticals to have Channel addition. In certain embodiments, Channel addition may enable Pharmaceuticals to Connect directly with consumers, to get direct consumer feedback or targeted marketing and coupons. In some embodiments, HealthBook may enable Retailers and Pharmacies to have Products commoditization over circles, to have Offers and walk-in clinic ads, appts and records. In still other embodiments, HealthBook may enable Research Community and Scientists to have Open science data and analytics.

In some embodiments, HealthBook may be a new privatebook. In other embodiments, HealthBook may enable a Pinboard and Timeline for personal health care and data management. In certain embodiments, HealthBook may enable Doctor Appointments to be made. In other embodiments, Healthbook may enable Prescriptions to be written or filled. In further embodiments, HealthBook may enable managements of records, image, or other private data created by care providers. In certain embodiments, the current disclosure may enable APIs to integrate facebook, google+ and other apps to pull data inside healthbook. In other embodiments, HealthBook may have Message boards to connect with care providers, insurance or labs. In other embodiments, HealthBook Circles may enable Alerts management, including Recalls, Vaccination, appts, prescriptions, new drugs etc. In some embodiments, HealthBook may enable Sponsor created circles where consumers can join for additional information and share experiences. In some embodiments, HealthBook may have Targeted Circle Advertisements, Videos and Banners may have Product and care provider Ratings, Likes, Coupons, may have Private rooms within circles to discuss personal data. In other embodiments, HealthBook may enable Web, apps, email and messaging features. In further embodiments, HealthBook may enable Web, apps, email and messaging features. For different platforms such as android, webos ios, mac, pc.

In further embodiments, Healthbook Data Storage may enable a Monthly subscription fee. In other embodiments, monthly fees may create the rights to information psychology. In some embodiments, Open Data Analytics may have a Monthly subscription fee. In some embodiments, Care Providers and Pharma may be enabled to have consumer connectivity. In other embodiments, HealthBook may enable Advertisements, Business and Network Creation, Coupons, Recalls, appt and prescription deliveries.

In some embodiments, HealthBook may enable applications to produce a new generation of information-based products & services, granularity and prediction in enterprise apps. In other embodiments, HealthBook may enable creation of Predictive analytics; demand for data scientists who can work on massive, unstructured data. In other embodiments, Analytics may be enabled to use 2+2=3.9 philosophy. In some embodiments, Healthbook may enable reporting. In certain embodiments, HealthBook may enable creation beyond dashboards visualizations, code swarms, etc. In other embodiments, HealthBook may enable a repository. In further embodiments, the repository may produce new architectures for scale out to handle massive data or unstructured data, such as Data Lakes. In further embodiments, HealthBook may enable more complex integration of diverse data. In certain embodiments, HealthBook may enable more complex integration of diverse data using automation and management tools. In other embodiments, HealthBook may enable collection of more data Coming from mobile, social, sensors, etc.

In further embodiments, the current disclosure may enable a Methodology to study the Economics of Social Capital In the context of the healthcare network. In some embodiments, Radcliffe-Brown's Theory may be applied To Healthcare. In certain embodiments, the Original theorem may be seen as a complex network of social relations, labeled social structure and he social structure can be uncovered through the development of a particular branch of mathematics that would focus on quantifying and analyzing relations as units of analysis. In some embodiments, Healthcare Network Analysis may enable Understanding the social structure of the healthcare system and focusing on quantifying, analyzing and understanding the impact of relations in the social structure. In certain embodiments, the current disclosure may enable a Healthcare System Model. In further embodiments, the current disclosure may enable a data model top level hierarchy. In another embodiment, the current disclosure may enable a healthcare data model drill down on medicine and participant. In some embodiments, the current disclosure may enable a healthcare data model to be drilled down on anatomy. In other embodiments, the current disclosure may enable a Healthcare Network (HCN) Model. In further embodiments, the current disclosure may enable HCN Data Model Top Level Hierarchy Relationships. In other embodiments, the current disclosure may enable HCN Data Model to be drilled down on a person. In certain embodiments, the current disclosure may enable HCN Data Model to be drilled down on organization. In another embodiment, the current disclosure may enable HCN Data Model Participants and Roles. In some embodiments, the current disclosure may enable HCN Data Model to be drilled down on professions, relationships, a condition, a record, or a treatment.

INDR: may be Individual patients

POPR: may be populations.

ELECTRONIC HEALTH RECORD (EHR): may be a systematic collection of electronic health information about INDR or POPR;

ELECTRONIC MEDICAL RECORD (EMR): may be a computerized medical record created in an organization that delivers care, such as a hospital or physician's office.

PERSONAL HEALTH RECORD (PHR): may be a health record where health data and information related to the care of a patient is maintained by the patient.

In some embodiments, an EHR may be enabled to be recorded in digital format that is theoretically capable of being shared across different health care settings. In further embodiments, EHRs may be enabled to include a range of data, including Demographics, Medical history, Medication and allergies, Immunization status, Laboratory test results, Radiology images, Vital signs, Personal stats like age and weight, or Billing information.

In certain embodiments, EMRs may be enabled to be a part of a local stand-alone health information system that allows Storage, Retrieval, or Modification of records.

In further embodiments, PHR may stand in contrast to the more widely used electronic medical record, which is operated by institutions (such as hospitals) and contains data entered by clinicians or billing data to support insurance claims. In some embodiments, the intention of a PHR may be to provide a complete and accurate summary of an individual's medical history which is accessible online. In certain embodiments, the health data on a PHR may include patient-reported outcome data, lab results, data from devices such as wireless electronic weighing scales or collected passively from a smartphone.

In other embodiments, the current disclosure may enable an HC Industry Model. In further embodiments, the current disclosure may enable an healthcare (HC) Industry model to be drilled down on an EMRs, a disease management system, a clinical system, doctors, hospitals, or PHRs, In some embodiments, the current disclosure may enable a sample topology. In further embodiments, the current disclosure may enable a sample topology participant and roles centric view. In certain embodiments, the current disclosure may enable a One-Mode HN People Social Fabric. In other embodiments, the current disclosure may enable a One-Mode HN Doctor Social Fabric. In still other embodiments, the current disclosure may enable a ONE-Mode HN Doctor Network. In some embodiments, the current disclosure may enable a Two-Mode HN Bipartite Graph People Doctor Social Fabric. In further embodiments, the current disclosure may enable a sample topology records centric view.

In some embodiments, the current disclosure may enable SNA concepts applied to Healthcare Network Analysis (HNA). In further embodiments, the current disclosure may enable Complete Networks. In certain embodiments, the current disclosure may enable Ego Networks. In further embodiments, the current disclosure may enable Networks where actors in the network are known beforehand and where the ties linking these actors together are then measured, such as an organization and its employees. In other embodiments, the current disclosure may enable ego networks to be formed by Studying personal, immediate networks surrounding an ego.

In certain embodiments, Edges may carry a sign, positive or negative. In some embodiments, the current disclosure may enable structural balance. In further embodiments, the current disclosure may enable Different Levels of Balance. In some embodiments, a balanced structure may indicate paths joining the same pair of nodes held the same sign. In some embodiments, a signed graph of any size may be considered balanced if the points can be separated into two mutually exclusive sub graphs. In further embodiments, these sub graphs may contain positive ties, and the ties between the sub graphs would be negative or absent.

In some embodiments, the current disclosure may enable Analysis of Ties (Links). In further embodiments, Positive Ties may represent Communication, Advice, or Friendship. In other embodiments, Negative Ties may represent Absence of ties, Dislike, or Distrust. In another embodiment, strength of ties may represent structural force.

In further embodiments, the current disclosure may enable automation HN topology analysis. In some embodiments, the current disclosure may enable analysis of HN shape and properties, may enable identification, may enable categorization, and may enable dynamic analysis.

In some embodiments, the current disclosure may enable centrality analysis. In further embodiments, centrality analysis may focus on people who occupy a central position in a network. In some embodiments, people who occupy a central position may be more visible, or may tend to know many people or many people tend to know them. In certain embodiments, the current disclosure may enable measurement of which actors are important to the network and/or important because of their network position. In another embodiment, the current disclosure may enable focusing on People that might be considered leaders, or may be at the center of gossip circles, or may be among the first to hear of any news. In certain embodiments, the current disclosure may enable actor level analysis. In further embodiments, actor level analysis may focus on measures of centrality. In other embodiments, actor level analysis may measure degree centrality or eigenvector centrality. In some embodiments, actor level analysis may analyze potential control or betweenness. In other embodiments, actor level analysis may analyze mobilization power, access, influence, independence, or closeness.

In some embodiments, actor level analysis may focus on degree centrality. In some embodiments, degree analysis may measure the number of immediate contacts an actor has in a network; may measure the level of involvement or activity; may consider how influential or popular the actor is. In some embodiments, degree analysis may interpret a high degree as a major channel for information. In other embodiments, Normalized centrality measures may allow for meaningful comparisons among actors in different networks. In some embodiments, degree analysis may not consider the rest of the network; may look at immediate ties of each actor. In further embodiments, degree analysis may ignore important pieces of information, namely, the other actors and ties in the network. In other embodiments, the degree analysis may focus on highest degree of ties to others, may focus on falls between other nodes may focus on who has the shortest path lengths to all other actors, or may focus on the closest actor to all others.

In further embodiments, actor level analysis may use outdegree or indegree analysis. In some embodiments, outdegree and indegree analysis may be measured on digraphs. In certain embodiments, indegree analysis may focus on the number of ties received by an actor, may focus on a measure for receive, or may focus on a measurement of prestige or popularity. In other embodiments, outdegree analysis may focus on the number of ties given by that actor to others, may focus on a measure for giving, or may focus on a measure for expansiveness.

In other embodiments, actor level analysis may use eigenvector centrality. In some embodiments, Eigen vector centrality analysis may expand the notion of degree centrality to look at the local network of actors immediately adjacent to your focal actor, which may providing a wider view of the network. In other embodiments, Eigen vector centrality analysis may focus on an actor's connections to other actors. In another embodiment, Eigen vector analysis may weight actor's connection to other actors by their degree centrality.

In further embodiments, actor level analysis may use betweenness. In some embodiments, betweenness may measure how often an actor rests between two other actors. In certain embodiments, betweenness analysis may focus on how many times the actor sits on the geodesic or shortest path, linking two other actors together. In other embodiments, betweenness analysis may enable the calculation of the length of geodesics linking pairs of actors. In some embodiments, betweenness analysis may require an actor to be an intermediary. In further embodiments, betweenness analysis may take into consideration the rest of the network when computing a score for an individual actor. In other embodiments, betweeness analysis may focus not on how many people an actor knows, but rather where the actor is placed within the network. In further embodiments, betweenness analysis may focus on the strategic and other advantages such an actor gains from occupying this position. In some embodiments, betweenness analysis in communications networks may measure how much control an actor has over the flow of information. In certain embodiments, an actor with high betweenness may greatly influence the network by choosing to withhold or distort information she/he receives. In some embodiments, normalized betweenness centrality scores may allow scores of actors from one network to those actors' scores of another network to be compared.

In another embodiment, actor level analysis may focus on closeness. In further embodiments, closeness may emphasize an actor's dependency. In some embodiments, closeness analysis may recognize that if an actor is not central, it relies on others to relay messages through the network. In some embodiments, closeness analysis may recognize that an actor that is close to many other actors is a very independent actor. In further embodiments, closeness analysis may recognize that a close actor can quickly reach others without having to rely much on intermediaries. In some embodiments, closeness analysis may recognize that an actor with high closeness may more easily mobilize a network, as the actor can more easily reach out to everyone in the network. In other embodiments, closeness analysis may be associated with an actor's power, influence, or ability to Access information in the network. In some embodiments, closeness may be determined by the short path lengths linking actors together. In other embodiments, closeness analysis may measure centrality as the distance between actors, where actors who have the shortest distance to other actors are seen as having the most closeness centrality.

In some embodiments, actor level analysis may focus on Beta-Centrality. In some embodiments, beta-centrality may recognize that the most powerful actor would be semi-peripheral ones, not the central ones. In further embodiments, beta-centrality analysis analyzes the nature of the relational context. In some embodiments, beta-centrality analysis may recognize positive relationships, such as communication, traditional may be good. In further embodiments, beta-centrality analysis may recognize that for negative relations, traditional may fail. In other embodiment's, beta-centrality analysis may enable use of a parameter called beta that can be controlled by the analyst. In further embodiments, beta may reflect the extent to which power is linked to the centrality of others. In some embodiments, small values of beta may weigh towards the local structure surrounding the actor. In other embodiments, larger value may weigh the equation towards the wider network.

In certain embodiments the current disclosure may enable an ego network view. In further embodiments, the ego network view may Focus on a focal Actor, or Ego. In some embodiments, the ego network view may represent all other Actors to whom Ego is connected to. In certain embodiment's, the Ego may be the central view of an ego network. In other embodiments, the ego network view may be composed of itself, the ego, and its intermediate contacts, referred to as alters. In further embodiments, ties may be measured between the ego and the alters, as well as between the alters. In other embodiments, measures of ego networks may be the Size of an ego-network, or How many alters an ego is tied to, Density, or the Extent to which ego's alters are also tied to one another, or the Strength of the ties connecting ego to alters. In certain embodiments, ego network analysis may enable areas of study including Structural holes of an ego, Broker roles of an ego, and Homophiious ties connecting egos and alters together. In some embodiments, ego network size may be calculated by adding the number of nodes in the ego network. In certain embodiments, alters may not be connected to the ego directly, but connected to an alter connected to the ego. In further embodiment's, ego network density may be calculated by dividing the number of ties present in the network which may not involve the go by the number of pairs of alters in the network. In another embodiment, dense networks may not have by definition structural holes. In other embodiments, a high density score for an ego may indicate that the ego's network does not have many structural holes. In further embodiments, certain network structures may give individuals a strategic advantage over others. In other embodiments, empty spaces in social structure may be from actors not having a tie between them. In certain embodiments, the present disclosure may recognize the role of structural holes in a company's innovation capacity. In other embodiments, structural holes may help an individual attain status. In certain embodiments, the present disclosure may recognize a relationship between structural holes and an ego's employee performance evaluations. In other embodiments, the present disclosure may recognize the role of structural holes in the performance and the success of individuals and work teams. In further embodiments, the present disclosure may recognize how structural holes relate to the capacity for generating good ideas.

In some embodiments, the present disclosure may enable brokers. In further embodiments, brokers between others benefit from the broker role. In some embodiments, Teritus Gaudens may represent the concept of brokers between others. In further embodiments, Teritus Gaudens may be similar to betweenness but central to one person. In some embodiments, Teritus Gaudens may be betweenness for a complete network. In other embodiments, brokers may benefit from profit, higher salaries, or good ideas within an organizational setting. In some embodiments, a coordinator broker may be an ego broker between two alters that are part of the same group. In another embodiment, a consultant broker may be an ego broker between two alters that are not part of the same group, but ego is in the same group as one of them. In other embodiments, brokers between groups may include representative brokers, gatekeeper brokers, or liaison brokers. In some embodiments, the current disclosure may analyze homophily. In other embodiments, homophily may refer to the social situation of actors preferring to have social relationships with others who are similar to themselves.

In other embodiments, an ego network may have representations of actors. In further embodiments, an actor may be a participant. In some embodiments, a participant may be people, may be organizations, or may be both people and organizations. In further embodiments, participant roles may be doctor or patients. In some embodiments, participant roles may be doctors and patients connected via a Serves relationship. In other embodiments, participant roles may payers or insurers. In some embodiments, the ego network may consist of People and their Roles.

In some embodiments, ego network analysis of HCN may focus on Ratio of Doctor Patient. In some embodiments, Ratio of Doctor Patient analysis may focus on doctor role and patient role connected via a Serves relationship. In other embodiments, Ratio of Doctor Patient analysis may measure the density of the graph.

In other embodiments, HNA may enable Dyads and Tryads Studies. In certain embodiments, Dyads and Tryads studies may disregard the role that larger structures have on the development and continuance of these dyad ties. In further embodiments, some organizations may encourage the creation of ties, such as Workplaces, Neighborhoods, Organizations, or Clubs. In other embodiments, Dryads and Tryads studies analysis may ignores how people make use of indirect ties to gain access to resources or other segments of the network. In other embodiments, dyads and tryads analysis may study the fundamental quality of the dyads. In further embodiments, Dyads and triads analysis may study Ties Between Pairs of Actors. In other embodiments, dyads and triads analysis may study how ties are, Initiated, Continued, or terminated. In further embodiments, dyads and triads analysis may Study what kinds of resources are exchanged, may Study reciprocity between actors, or may Study the strength of ties. In other embodiments, dyads and triads analysis may enable a dyad census. In some embodiments, a dyad census may enable a way to understand or characterize ties, such as a kind of relational tie, strength of the tie, direction of the tie, or duration of the Tie. In further embodiments, dyads and triads analysis may recognize three states of ties. In another embodiment, a mutual tie state may be more stable, more trust and more positive affection. In a further embodiment, an asymmetric tie may be based on exchange, or may signify Power, knowledge and expertise are distributed unevenly in a network. In a still further embodiment, a null tie state may characterize an empty network. In some embodiments, dyads and triads analysis may study strength of ties and multiplexity. In some embodiments, dyads and triads analysis may analyze Strength as relative concept, comprising a combination of how much time both actors spent together, emotional intensity of the relationship, Level of intimacy and/or mutual confiding, or Amount of reciprocal services or favors. In further embodiments, dyads and triads analysis may study multiplexity or sharing more than one kind of tie.

In further embodiments, dyads and triads analysis may enable Social Comparison Theory. In further embodiments, social comparison theory may refer to the process whereby individuals exchange views with one another, comparing their own views with those of others to arrive at a sense for having, ultimately, the correct perspective. In some embodiments social comparison theory may be studied at the dyad level through Frequency of interaction, Tie Multiplexity, Strength of tie, or Asymmetry.

In other embodiments, Dyads and Triads analysis may study Simmelian Ties. In some embodiments, Simmelian Ties analysis may study dyads in relation to Triads. In further embodiments, two actors involved in a dyad relation may tend to share a stronger, more durable tie if that dyad were embedded within a triad. In some embodiments, these actors may be more stable over time.

In certain embodiments, triads may Consist of three actors (or nodes) and all the arcs between them. In some embodiments, triads may be composed of different kinds of dyad configurations among a set of three actors. In some embodiments, dyads and triads analysis may enable a Structural Concept of Transitivity. In certain embodiments, transitivity may comprise the Main structural characteristic of networks. In some embodiments, transitivity may be explored through the use of a triad census. In certain embodiments, if Actor i is tied to actor j, and Actor j is tied to actor k, then Actor i is likewise tied to actor k. In other embodiments, dyads and triads analysis may study Intransitive Triads. In some embodiments, dyads and triads may study Granovetter's Forbidden Triangle.

In further embodiments, dyads and triads analysis may study Strong Ties and Weak Ties. In certain embodiments, Strong Ties may be Bi-Directional Ties. In some embodiments, strong ties may Creates a structural force or may Pressure actors to acknowledge one another's presence and may form some kind of social tie with each other. In other embodiments, when a triad consists of strong ties, an open triad may be forbidden. In further embodiments, Weak Ties may be Uni-Directional Ties.

In other embodiments, Dyads and Triads may enable Structural Biases. In some embodiments, structural biases may be Different from random networks. In further embodiments, Social Networks may have structural biases that include the tendency for reciprocity between dyads. In other embodiments Reciprocity Bias may enable Positive Ties such as Reciprocal Ties or Bi-directional Ties.

In certain embodiments, the current disclosure may analyze the multiplexity of ties between people as inferred by the ties between the roles they play. In some embodiments, a person A may be a doctor and a friend of person B and just a doctor of person C.

In other embodiments, the current disclosure may enable a subgroup level analysis. In some embodiments, a subgroup may refer to an area of a network larger than a dyad or triad yet smaller than an entire network. In other embodiments, a subgroup when viewed as a form of network structure may influence the behavior and/or values of individuals and the collective. In certain embodiments, a cohesive subgroup may be a subgroup in which a high proportion of the actors within the subgroup share ties that are strong, direct, mutual, frequent or positive ties. In yet further embodiments, a subgroup level may be cohesive. In another embodiment, a cohesive subgroup may be difficult to break apart by the removal of one or more of its ties. In another embodiment, if two actors are well connected to one another, then there may be more than one path connecting them together. In other embodiments, if you remove of these paths, the two actors may remain connected to each other. In some embodiments, subgroup level components may be the most minimum requirement for a cohesive subgroup. In further embodiments, a component may consist of a subgroup of individuals, whereby all the individuals may be connected to one another by at least one path. In other embodiments, an isolate component may be an actor not having any ties to anyone else. In further embodiments, components may be strong or weak. In another embodiment, a weak component may indicate actors are connected to one another, regardless of the direction of the ties. In further embodiments, a weak path may be a path linking an actor to all other actors, when the direction of the arcs is ignored. In certain embodiments, weak components may be the ones where the actors are connected via weak paths. In other embodiments, a Strong Component may refer to actors being connected to one another via direct or indirect ties. In further embodiments, a path linking an actor to all other actors, when the direction of the arc is recognized, may be called a strong path. In some embodiments, a Strong component may be connected via strong paths.

In some embodiments, subgroup analysis may enable Cliques and n-Cliques analysis. In some embodiments, informal groupings of people in which feelings of intimacy exist, and where the presence of particular group norms and sub-culture exist may provide a Sense for strong cohesiveness. In certain embodiments, a subgroup may start developing its own set of norms, rules and culture different from the larger network or social system in which it is embedded. In other embodiments, this may be important as reference points for individuals and an individual's identity. In some embodiments, Clique may be subgroups of people consisting of mutual ties.

In some embodiments, cliques may be a complete subgraph, one consisting of three or more actors, who are directly connected to one another through mutual ties. In other embodiments, cliques may be defined solely on network structural features, and may not depend on notions of culture, norms or intimacy. In other embodiments, cliques may be analyzed on graphs as opposed to digraphs. In certain embodiments, clique analysis may recognize clique overlap. In some embodiments, clique overlap may occur whenever one or more actors from one click can simultaneously be included as a member(s) of another clique. In further embodiments, this co-membership in cliques may be reflective of the notion of social circles in sociology, where actors belonging to multiple groups are seen as playing important bridging roles that link social groups together and build cohesion on the social level. In some embodiments, n-cliques may be a subgroup in which each every PAIR of actors is connected by a path of length n or less. In certain embodiments, N may stand for the length of the path connecting one actor to another. In other embodiments, if ties mean friendship for example, 1-Clique may indicate everyone is friends with everybody. In other embodiments, if ties mean friendship for example, 2-Clique may indicate everyone is at least a friend of a friend.

In some embodiments, subgroup level analysis may analyze K-core. In further embodiments, K-cores may not be cohesive per se but they may contain cohesive groups. In certain embodiments, K-core analysis may be built on the concept of degree centrality. In other embodiments, an actor may be part of a k-core if they have at least a degree centrality of k within that group. In some embodiments, an actor may be part of k-core if they are part of k members of that sub-group. In further embodiments, as the value of k becomes lower, subgroup sizes may increase, and may become easier to draw a boundary of that group. In other embodiments, as the value of k becomes higher, it may become harder for an actor to join that group. In certain embodiments, the lower and higher values for k may translate into a hierarchy of subgroups and the k-cores may be seen as nested in one another. In some embodiments, actors involved in higher level k-cores may be seen as the more important actors for holding the network together.

In certain embodiments, subgroup analysis may analyze Lambda sets. In further embodiments, lambda sets may build on the idea of connectivity between two actors, and may also into consideration how connectivity within a group compares to connectivity outside of this group. In some embodiments, for example, two actors I and J may be considered to be part of the same lambda set if the number of paths connecting I and j together is larger than the number of paths connecting I to an outside actor, for example j, or j to k. In other embodiments, as the lambda value increases, this may restrict how many actors can join the set. In further embodiments, high values of lambda may imply a high number of independent paths linking two actors together. In certain embodiments, a lambda set with a high value may identify the vulnerable bridges in a network. In another embodiment, deleting or eliminating the ties in this particular set may disrupt and fragment the network.

In other embodiments, subgroup level analysis may analyze Girvan-newman Algorithm. In certain embodiments, Girvan-Newman analysis may be based on the identification and removal of between edges. In further embodiments, Girvan-Newman analysis may break down a complex network into clusters or communities. In other embodiments, Girvan-Newman analysis may work by removing edges that sits between cohesive segments of the network. In another embodiment, it may be a fragmentation process whereby the edges that remain are those contained in a cohesive subgroup. In some embodiments, for example teenager behavior may be strongly linked to membership in a clique, whereby individual teenagers' behaviors may mirror those of other clique members.

In further embodiments, subgroup analysis may analyze affiliation networks. In certain embodiments, a two-mode network may be where actors are shown in relation to events or organizations, resulting in an actor×event matrix and/or a bipartite graph. In some embodiments, affiliation networks may be used for uncovering subgroups where actors are organized into subgroups by virtue of their affiliation to different organizations or events.

In certain embodiments, the current disclosure may enable network level analysis. In some embodiments, network level analysis may attempt to uncover some features of the network that characterize the network as a whole. In further embodiments, network level analysis may analyze the tendency the network has for transitive triads. In other embodiments, network level analysis may enable a network to be characterized as transitive or not. In further embodiments, network level analysis may imply other Global Structures, such as clustering.

In some embodiments, the current disclosure may enable a Triad Census. In certain embodiments, conducting a triad census may be seen as linking micro-level structures to global ones. In other embodiments, triad census analysis may uncover lower-level structural tendencies. In further embodiments, triad census analysis may enable a determination about the network as a whole. In further embodiments, tried census analysis may recognize the extent of which a network stays together versus the extent to which a network breaks apart. In other embodiments, the extent to which a network does not break into these sub-structures may depend on issues of cohesion.

In further embodiments, network level analysis may analyze density. In some embodiments, density may refer to the proportion of ties in a network that are actually present. In other embodiments, density analysis may examine the extent of which all the individual actors in a network are linked together. In certain embodiments, density analysis may count how many of the actual ties exist in a network, and expresses this number as a proportion of the potential ties that could exist in the network. In further embodiments, a higher the density score may indicate a denser your network, and thus, a more cohesive network. In some embodiments, density analysis may analyze the Role of Subgroups in Density Scores. In further embodiments, density analysis may recognize issues with understanding the link between density score and the conclusion that a network is or is not cohesive. In some embodiments, such issues may include centralization, or increasing density through one person, decreasing density through increasing network size, or increasing density through number of cohesive subgroups.

In other embodiments, network level analysis may analyze centralization. In further embodiments, centralization analysis may recognize high density through ties occurring main through one person. In certain embodiments, centralization analysis may consider density to represent average. In further embodiments, good cohesiveness average throughout the network may imply low variance. In other embodiments, network centralization may also be used as an indicator for a core-periphery structure. In certain embodiments, high centralization score may mean a clear delineation between core and periphery.

In some embodiments, network level analysis may analyze different structures of the same density. In some embodiments, network level analysis may enable decreased density through Increased Network Size. In some embodiments, larger networks may have a greater potential for more ties, and may make harder for larger networks to have a higher density value. In another embodiment, network level analysis may be required to consider network size. In some embodiments, when comparing density of networks, they may be required to be the same size;

In another embodiment, network level analysis may enable increased density through Cohesive Groups. In further embodiments, high network density may result from many subgroups. In some embodiments, low densities in larger networks may reflect more structural cohesion than higher densities in smaller networks; as such large networks have fewer cohesive subgroups, and hence, less amount of fragmentation.

In certain embodiments, network level analysis may analyze Network Diameter. In further embodiments, network diameter may represent average path length. In some embodiments, average path length may be the longest geodesic in a network, where a geodesic refers to the shortest path between two actors. In some embodiments, if the diameter is relatively small, then everyone may be relatively close to one another, and therefore the network may be cohesive. In other embodiments, the average path length may equal the average of the geodesics in the network as an indicator for how close together actors are to one another.

In further embodiments, network analysis may analyze small worlds. In certain embodiments, small worlds may be characterized as Low density, High average, Clustering, or Short average path length. In some embodiments, while they may contain a large number of actors, actors may reach all other actors through a small number of intermediary links in a chain of acquaintance. In some embodiments, measures for average clustering may be calculated by taking the average of all ego network density scores found in a given network.

In some embodiments, the current disclosure may enable Healthcare Network Analysis. In a particular embodiment, Position and Roles Analysis may be enabled. In an embodiment, Position and Roles Analysis may leverage concepts in sociology and in network analysis. In other embodiments, analysis may begin with a positional analysis and then derives the role analysis where a position may be for an actor within a group and a relation may be between groups. In alternative embodiments, a position of an actor may be defined by the group or block to which an actor is assigned. In further embodiments, roles may be defined by the relations between blocks. In some embodiments, if one block seems to be more active in connecting with the other blocks, then the actor in this block may be seen as taking on the role of active communicators.

In certain embodiments, analysis may include position And Roles Analysis. In some embodiments, positional Blocks or Actors may be included in the representation or analysis. In certain embodiments, subsets of actors may be grouped together into positional blocks or classes, and these subsets may be derived from how actors within the subset share similar ties to other in a different subset. In some embodiments, subsets based on positions may be derived from how actors within the subset connect to others outside the subset as well as within the subset. In further embodiments, roles may be defined by how these positional blocks relate to one another. In other embodiments, Positional/role analysis may be done on multiple relations. In an embodiment, multiple relations that link positions together may give an analyst an overall picture of the role of the structure in a given network.

In a particular embodiment, roles may derive from multiple relations linking positions together. In certain embodiments, equivalence may be defined. In some embodiments, equivalence may be defined by structure. In other embodiments, equivalence may be regular and may share similar ties to similar others. In other embodiments, equivalence may not dependent on proximity. In other embodiments, equivalence may be determined by looking at Actor attribute data. In an embodiment, there may be a measure of equivalence which may be given by a Pearson r and or a Euclidian Distance. In other embodiments, actors may be assigned into positions.

In some embodiments, the current disclosure may enable Block Modeling. In certain embodiments, actors may be grouped into blocks according to how similar these actors are to one another in their relations to others. In other embodiments, a large network may be reduced to a smaller and simpler representation so that positions and roles can be more easily interpreted. In some embodiments, a block model may consist of two main components. In a first embodiment, actors may be partitioned in a network into blocks based on multi relational data, where each block represents a unique position in the network. In another embodiment, there may be a representation of the ties within and between positions. In some embodiments, block models may be represented as formal models of hypotheses about multi-relational networks. In further embodiments, the analysis may consider Structural Equivalence. In some embodiments, actors may be structurally equivalent if they share one or more of the same ties with the same others, and in addition, the same values, type of relations, and direction of ties. In further embodiments, structural equivalence may be an ideal in which analysts study to what degree actors get close to this ideal. In other embodiments, analysis may examine the extent to which actors approximate structural equivalence. In a further embodiment, position and roles analysis may examine network to determine the roles that emerge from the way positional blocks relate to one another. In another embodiment, position and roles analysis may enable a core-periphery network analysis. In certain embodiments, a core-periphery network may contain a core whose actors relate to others in the core and periphery. In further embodiments, a core-periphery network may contain a periphery whose actors relate to those in the core, and no one in the periphery. In other embodiments, a core-periphery network may indicate which subset of actors, i.e., those occupying the core, have more power than others.

In some embodiments, a health care analysis enables a network levels analysis. In further embodiments, network levels analysis may examine group effect, macro level structures, or social phenomena. In other embodiments, network level analysis may focus on micro social interactions among individuals and small groups. In some embodiments, a dyad may represent a relationship between two people. In further embodiments, people may maintain their identity. In some embodiments, a triad may represent a relationship between three or more people. In other embodiments, a triad may change the social dynamics in crucial ways. In some embodiments, a triad may enable an understanding society at large, for example, how larger structures constrain individuals. In certain embodiments, a group effect may be more likely to occur. In some embodiments, a mediator may mediate between individuals and benefit from that position as teritus gaudens.

In other embodiments, healthcare network analysis may use a social influence network theory approach. In certain embodiments, a social influence network theory approach may examine the role networks play in shaping and influencing actor's perceptions, behaviors and attitudes. In some embodiments, social influence network theory approach may suggest that actors that are similar according to attitudes, values and behaviors are likely to be socially tied to one another. In certain embodiments, social influence network theory approach may suggest that it is through these social ties that actors mutually influence one another and become similar to one another over time.

In further embodiments, healthcare network analysis may use a social exchange theory approach. In some embodiments, a social exchange theory approach may consider exchanging social and material resources is fundamental to all human interaction. In other embodiments, social exchange theory approach may indicate that such exchange interactions are shaped by unequal power relationships between individuals, which in turn may be influenced by the network structure in which actors are found.

In some embodiments, a healthcare network analysis may examine exactness. In further embodiments, a healthcare network analysis may examine social capital. In other embodiments, a social capital analysis may examine bridging social capital. In other embodiments, bridging social capital approach may examine weak ties and open networks. In further embodiments a social capital analysis may examine bonding social capital. In some embodiments bonding social capital approach may examine strong ties or dense social networks. In other embodiments a healthcare network analysis may include small worlds research. In furthers embodiments, a small world research approach may examine large networks of heterogeneous actors who are linked together through a small number of intermediaries. In still a further embodiment, healthcare network analysis may examine conditional dependence. In other embodiments, healthcare network analysis may examine exponential random graph models (ERGM).

In some embodiments, healthcare network analysis may be performed based on the connectivity strength. In certain embodiments connectivity strength may represent how many consumers are connected to a provider or may represent how many consumers connected to a specific treatment or drug. In other embodiments healthcare network analysis may be performed based on cost. In certain embodiments an analysis based on cost may compare provider costs on specific services or may examine location based searches for services. In further embodiments, a graph algorithm comprises cost and quality inferences based on connectivity strengths.

Data Model

In most embodiments a data model or modeling structure may be used to process data across clusters. In most embodiments, the data model may enable representation of multiple data sets. In certain embodiments, this model may include data notes, data clusters, data centers, clouds, and skies.

In most embodiments, the classes, objects, and representations referenced herein may be an extension of known distributed system models, such as the EMC/Smarts Common Information Model (ICIM), or similarly defined or pre-existing CIM-based model and adapted for the environmental distributed system, as will be discussed. EMC and SMARTS are trademarks of EMC Corporation, Inc., having a principle place of business in Hopkinton, Ma, USA. In certain embodiments, this exemplary model may be an extension of the DMTF/SMI model. Model based system representation is discussed in commonly-owned U.S. patent application Ser. No. 11/263,689, filed Nov. 1, 2005, and Ser. No. 11/034,192, filed Jan. 12, 2005 and U.S. Pat. Nos. 5,528,516; 5,661,668; 6,249,755 and 6,868,367, and 7,003, 433, the contents of all of which are hereby incorporated by reference. An example of a Big Data Set may be found in commonly-owned U.S. patent application Ser. No. 12/977, 680, filed Dec. 23, 2010, entitled "INFORMATION AWARE DIFFERENTIAL STRIPING" the contents of which are hereby incorporated by reference. An example of modeling Big Data Set may be found in commonly-owned U.S. patent application Ser. No. 13/249,330, filed Sep. 30, 2011, and entitled "MODELING BIG DATA" the contents of which are hereby incorporated by reference. An example of analyzing Big Data Set may be found in commonly-owned U.S. patent application Ser. No. 13/249,335, filed Sep. 30, 2011, and entitled "ANALYZING BIG DATA" the contents of which are hereby incorporated by reference.

Generally, referred-to US Patents and patent applications disclose modeling of distributed systems by defining a plurality of network configuration non-specific representations of types of components (elements or devices) managed in a network and a plurality of network configuration non-specific representations of relations among the types of managed components and problems and symptoms associated with the components and the relationships. In some embodiments, the configuration non-specific representations of components and relationships may be correlated with a specific Big Data set for which the associated managed component problems may propagate through the analyzed system and the symptoms associated with the data set may be detected an analyzed. In certain embodiments, an analysis of the symptoms detected may be performed to determine the root cause—i.e., the source of the problem—of the observed symptoms. Other analysis, such as impact, fault detection, fault monitoring, performance, congestion, connectivity, interface failure, in addition to root-cause analysis, may similarly be performed based on the model principles described herein.

Healthcare

Typically, health care networks are divided into disparate systems that do not share data between systems. Generally, this may lead to several siloed systems acting in isolation. Conventionally, information such as the cost of a procedure may not be accessible at different hospitals. Usually, there may not be a way to combine information across these systems. Conventionally, this lack of information may lead to higher prices and not enable each system to share information with each other system.

In certain embodiments, the current disclosure may enable integration of different health care players or systems into a single system or model. In some embodiments, a health care topology may be created upon which analysis may be performed. In further embodiments, the current disclosure may enable deployment of services and data in a health care network. In certain embodiments, the instant disclosure may lower costs in a health care network or system. In most embodiments, relationships between entities may have properties, which may record information about the relationship. In further embodiments, information sharing may be enabled at the patient level. In some embodiments, one or more health care networks or systems may be modeled to enable information sharing and analysis across the models.

Figure 1:
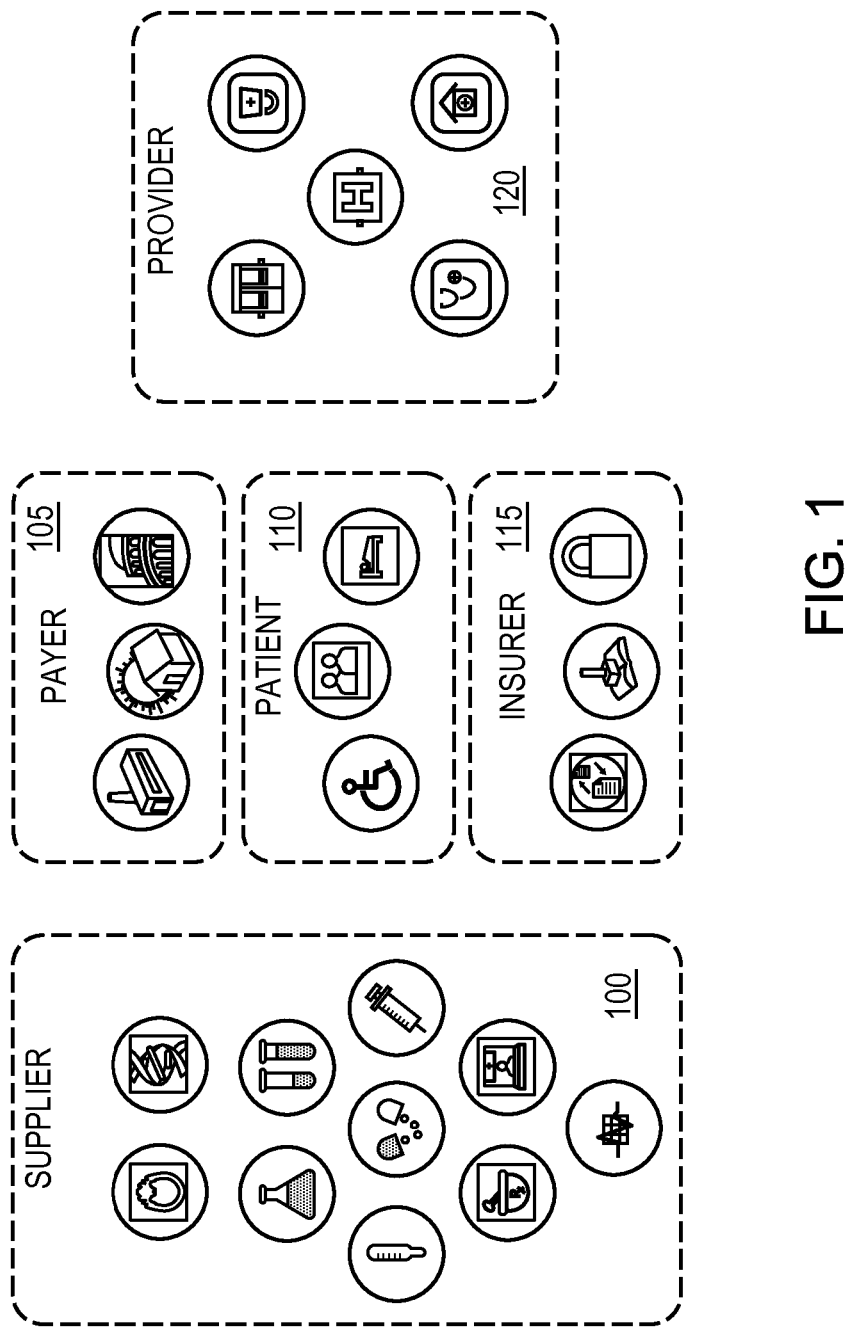
FIG. 1 is a simplified illustration of players in a health care system, in accordance with an embodiment of the present disclosure.

Refer now to the example embodiment of FIG. 1, which illustrates players in a health care system. In the example embodiment of FIG. 1, there are 5 different players, supplier 100, payer 105, patient 110, insurer 115, and provider 120. In the example embodiment of FIG. 1, each of these players is isolated from each other. In certain embodiments, the different players may represent actors within a health care system or network.

In certain embodiments, the current disclosure may enable sharing between the players in a health care system. In some embodiments, sharing of data between the players may lower cost. In most embodiments, sharing of the data between players may enable optimization of the health care system.

Figure 2:
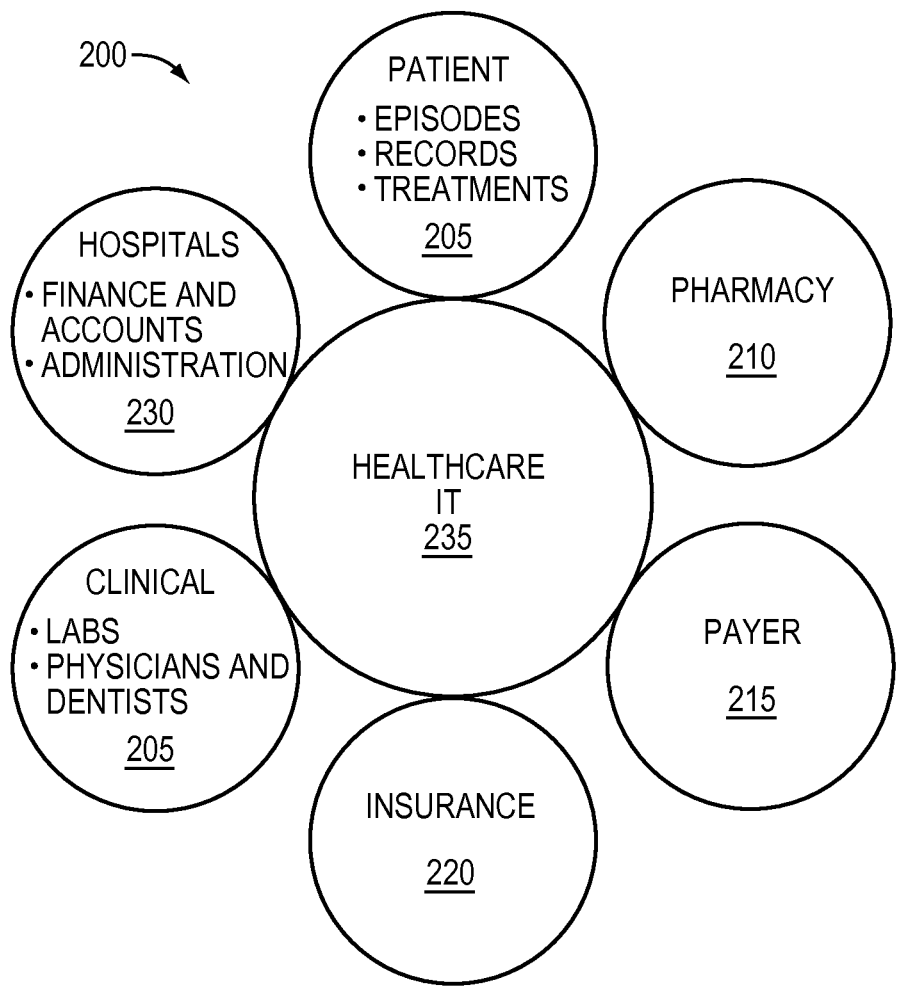
FIG. 2 is a simplified illustration of information sharing between players in a health care system, in accordance with an embodiment of the present disclosure.

Refer now to the example embodiment of FIG. 2, which illustrates information sharing between players in a health care system. In the example embodiment of FIG. 2, patient 205, pharmacy 210, payer 215, insurance 220, clinical 225, and hospitals 230 are linked together through healthcare Information technology 235. In this embodiment, each player in the health care system is enabled to share information with each other player. In certain embodiments, sharing of information may be limited by regulation, such as privacy or other laws.

Figure 3:
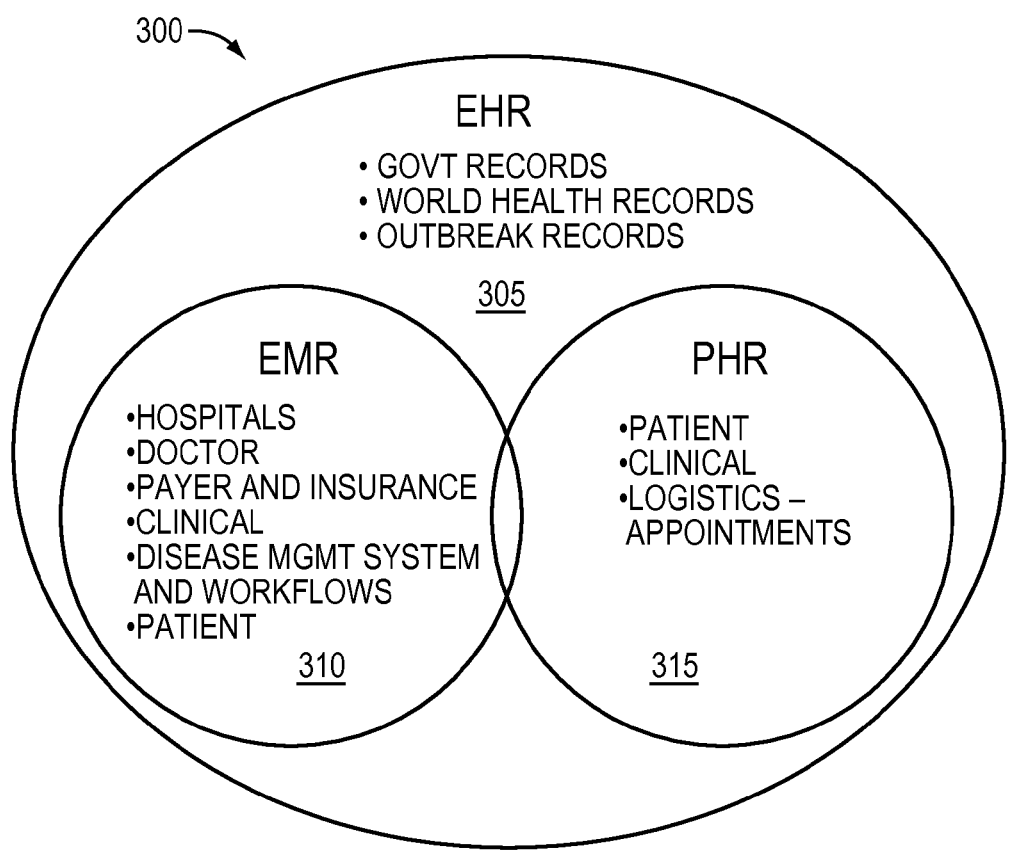
FIG. 3 is a simplified illustration of health care records, in accordance with an embodiment of the present disclosure.

Refer now to the example embodiment of FIG. 3, which illustrates health care records. In the example embodiment of FIG. 3, there is electronic health record (EHR) 305. Within EHR 305, there is electronic medical record (EMR) 310 and personal health record 315. EMR 310 has information on hospitals, doctors, payer and insurance information, clinical information, disease management systems and workflows, and patent information. Personal Health Record (PHR) 315 has patient, information, clinical information, and logistical and appointment information.

In further embodiments, the present disclosure may present a model to enable health care players to interact. In other embodiments, the current disclosure may enable representation of the characteristics and properties of the players in a health care system to facilitate data flow between the players. In further embodiments, the representation may contain information about each player or entity in the health care system.

Figure 4:
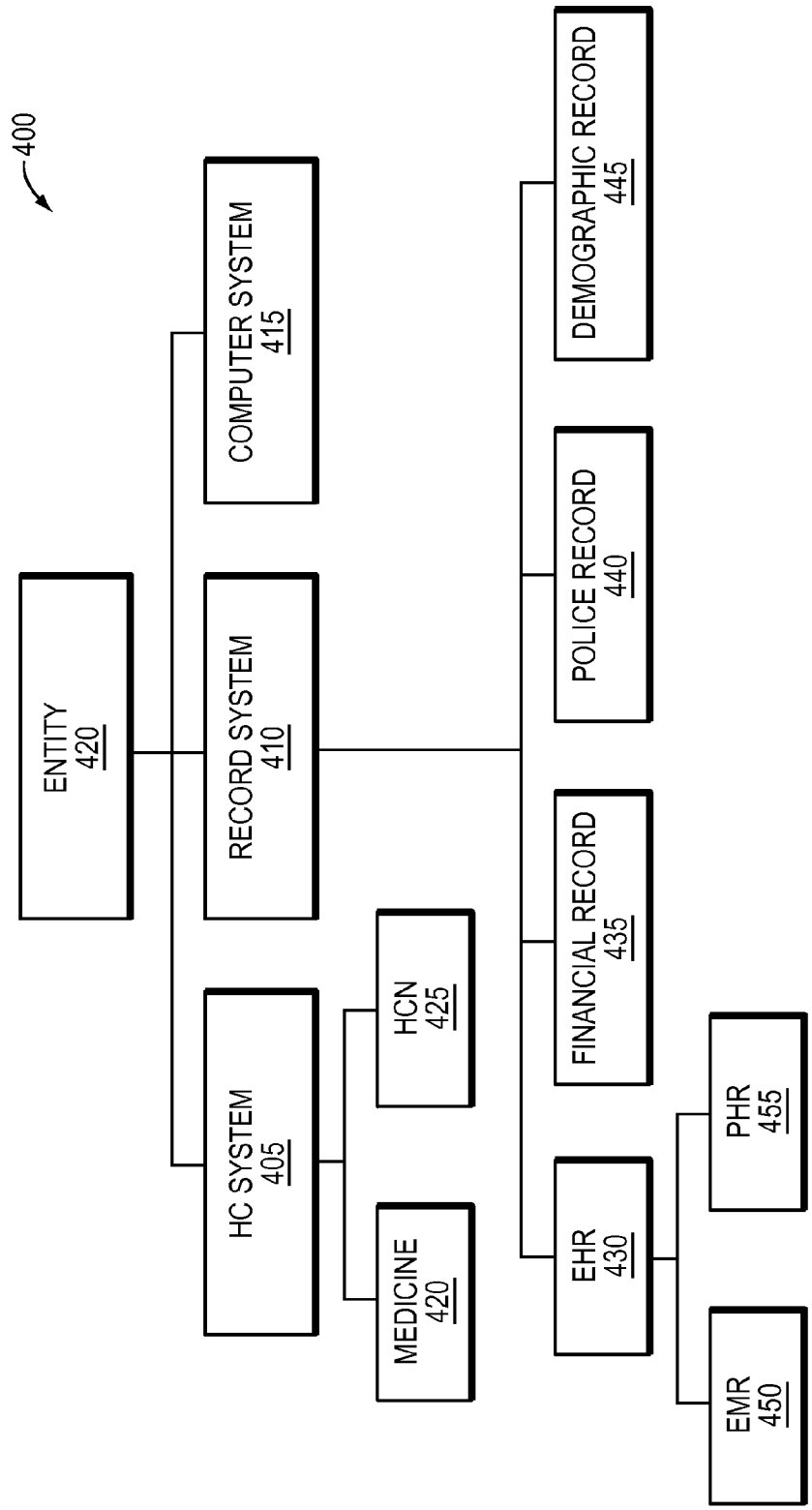
FIG. 4 is a simplified illustration of the relationship between actors in a health care system model, in accordance with an embodiment of the present disclosure.

Refer now to the example embodiment of FIG. 4, which illustrates relationship between actors in a health care system model. In the example embodiment of FIG. 4, entity 420 is connected to health care system 405, record system 410, and computer system 415. Health care system 405 has medicine 420 and health care network 425. Record system has electronic health care record 430, financial record 435, police record 440, and demographic record 445. Electronic health record 430 has electronic medical record 450 and personal health record 455.

Figure 5:
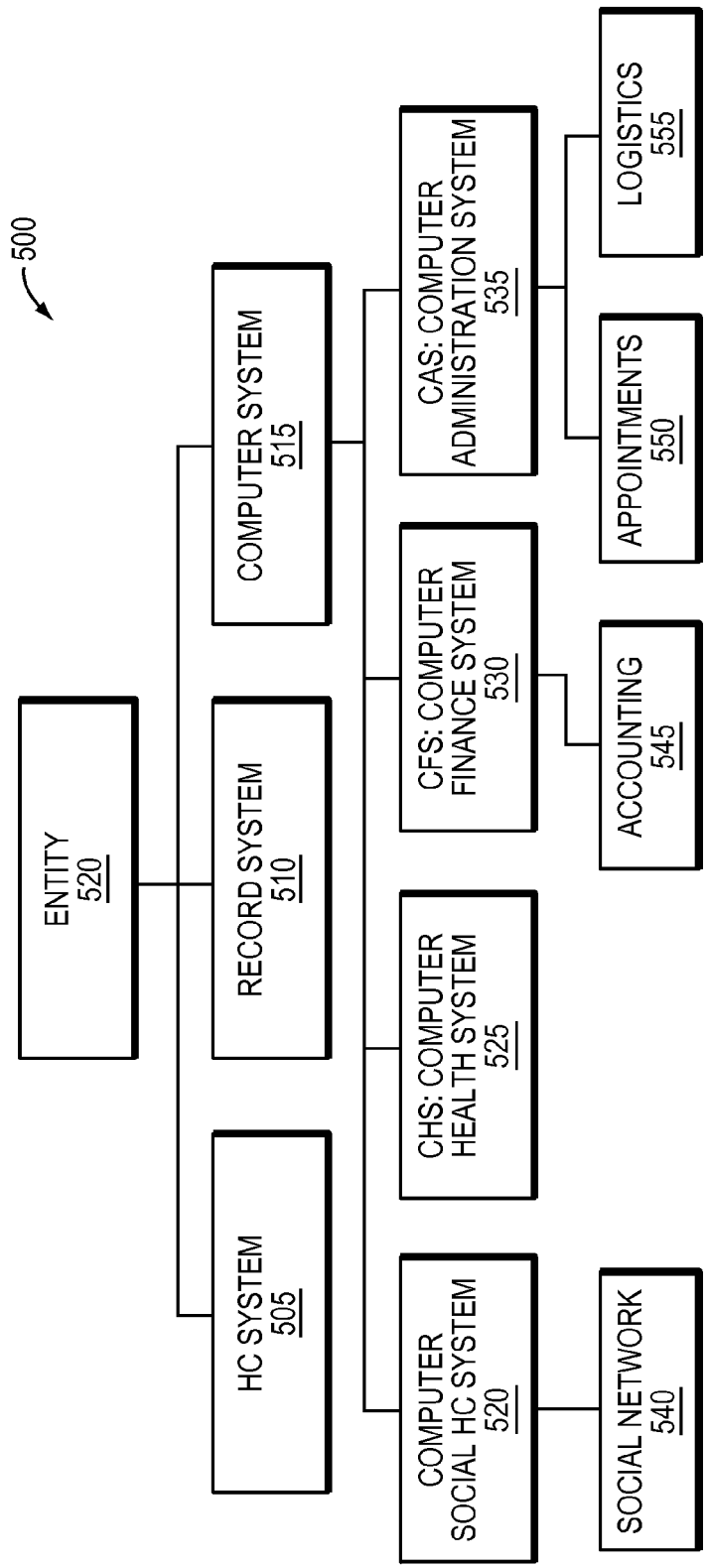
FIG. 5 is a simplified illustration of entities and relationships in a health care system model including a computer system and sub components, in accordance with an embodiment of the present disclosure.

Refer now to the example embodiment of FIG. 5, which illustrates entities and relationships in a health care system model. In the example embodiment of FIG. 5, there entity 520 has health care system 505, record system 510, and computer system 515. Computer system 515 has computer social health care system 520, computer health system (CHS) 515, computer finance system 530, and computer administration system 535. Computer social health care system 520 has social network 540. Computer finance system 520 has accounting 545. Computer administrative system 535 has appointments 550 and logistics 555.

Figure 6:
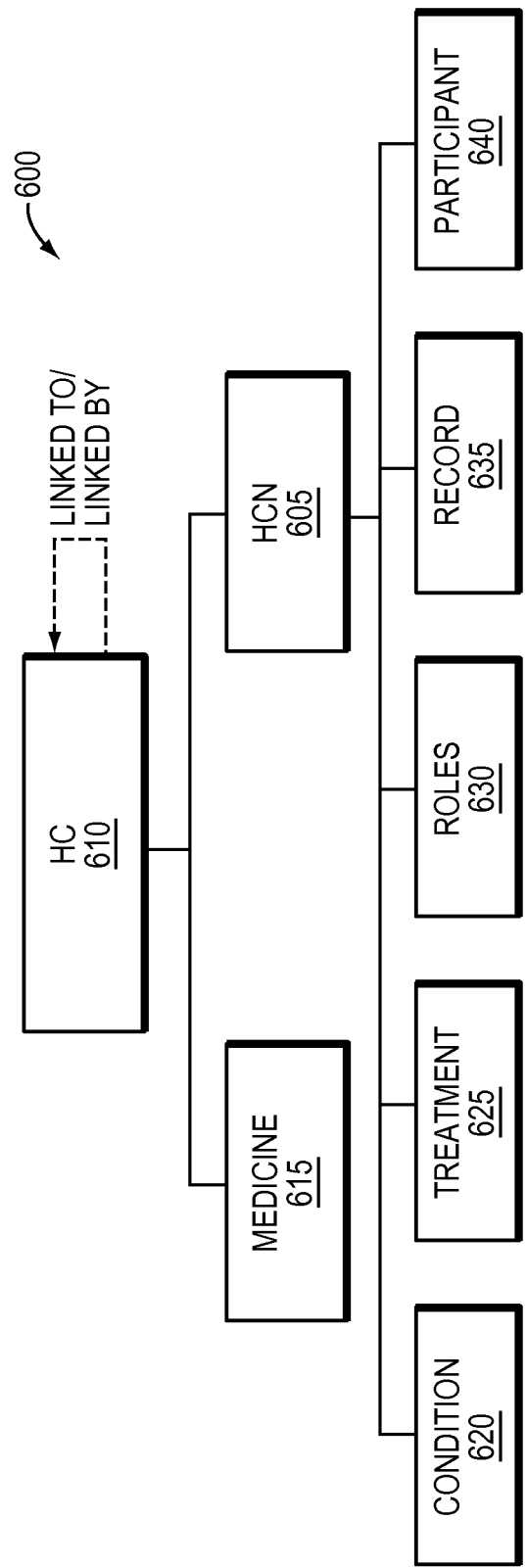
FIG. 6 is a simplified illustration of entities and relationships in a health care system model including conditions, treatments, roles, records, and participants, in accordance with an embodiment of the present disclosure.

Refer now to the example embodiment of FIG. 6, which illustrates entities and relationships in a health care system model. In the example embodiment of FIG. 6, health care 610 has medicine 615 and health care network 605. Health care network 605 has condition 620, treatment 625, roles, 630, record 635, and participant 640.

Figure 7:
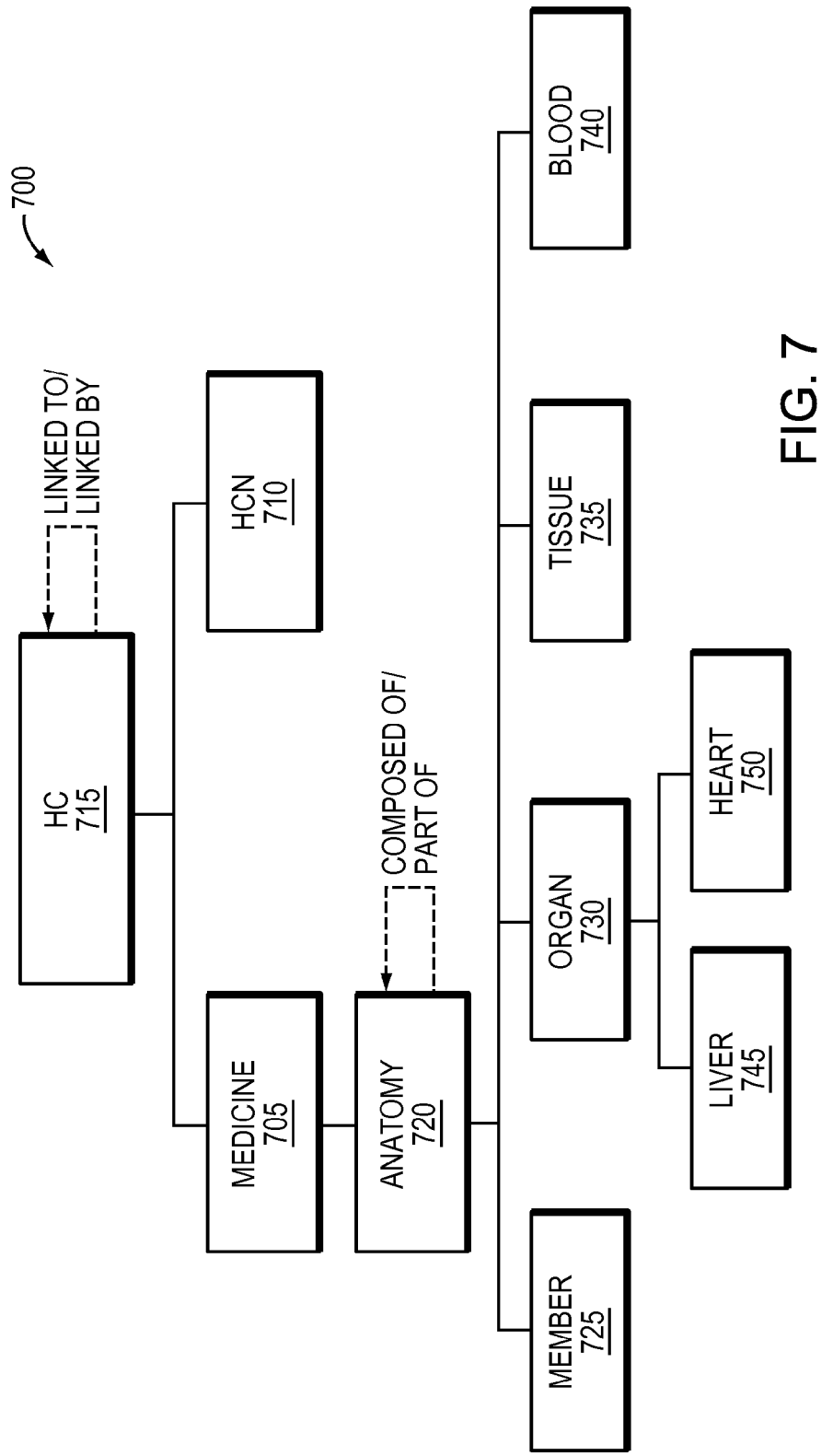
FIG. 7 is a simplified illustration of entities and relationships in a health care system model including anatomy, in accordance with an embodiment of the present disclosure.

Refer now to the example embodiment of FIG. 7, which illustrates entities and relationships in a health care system model. Health care 705 has medicine 705 and health care network 710. Medicine is linked to/Composed in part/part of anatomy 720. Anatomy 720 has member 725, organ 730, tissue 735 and blood 740. Organ 730 has liver 745 and heart 750.

Figure 8:
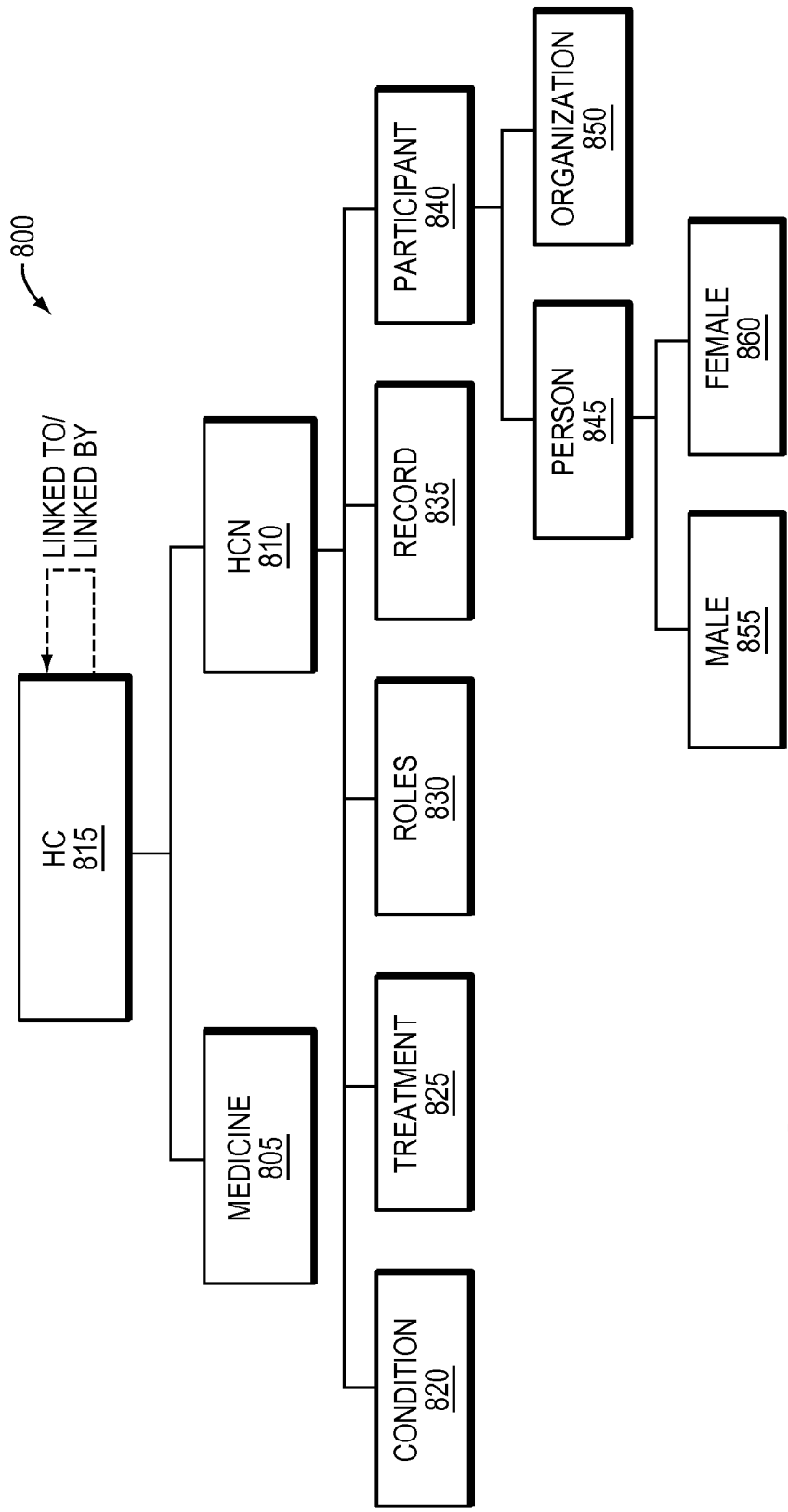
FIG. 8 is a simplified illustration of entities and relationships in a health care system model including participant information, in accordance with an embodiment of the present disclosure.

Refer now to the example embodiment of FIG. 8, which illustrates entities and relationships in a health care system model. In the example embodiment of FIG. 8, health care has medicine 805 and health care network 810. Health care network 810 has condition 810, treatment 825, roles 830, record 835 and participant 840. Participant 840 has person 845 and organization 850. Person 845 has attribute male 855 or female 860.

Figure 9:
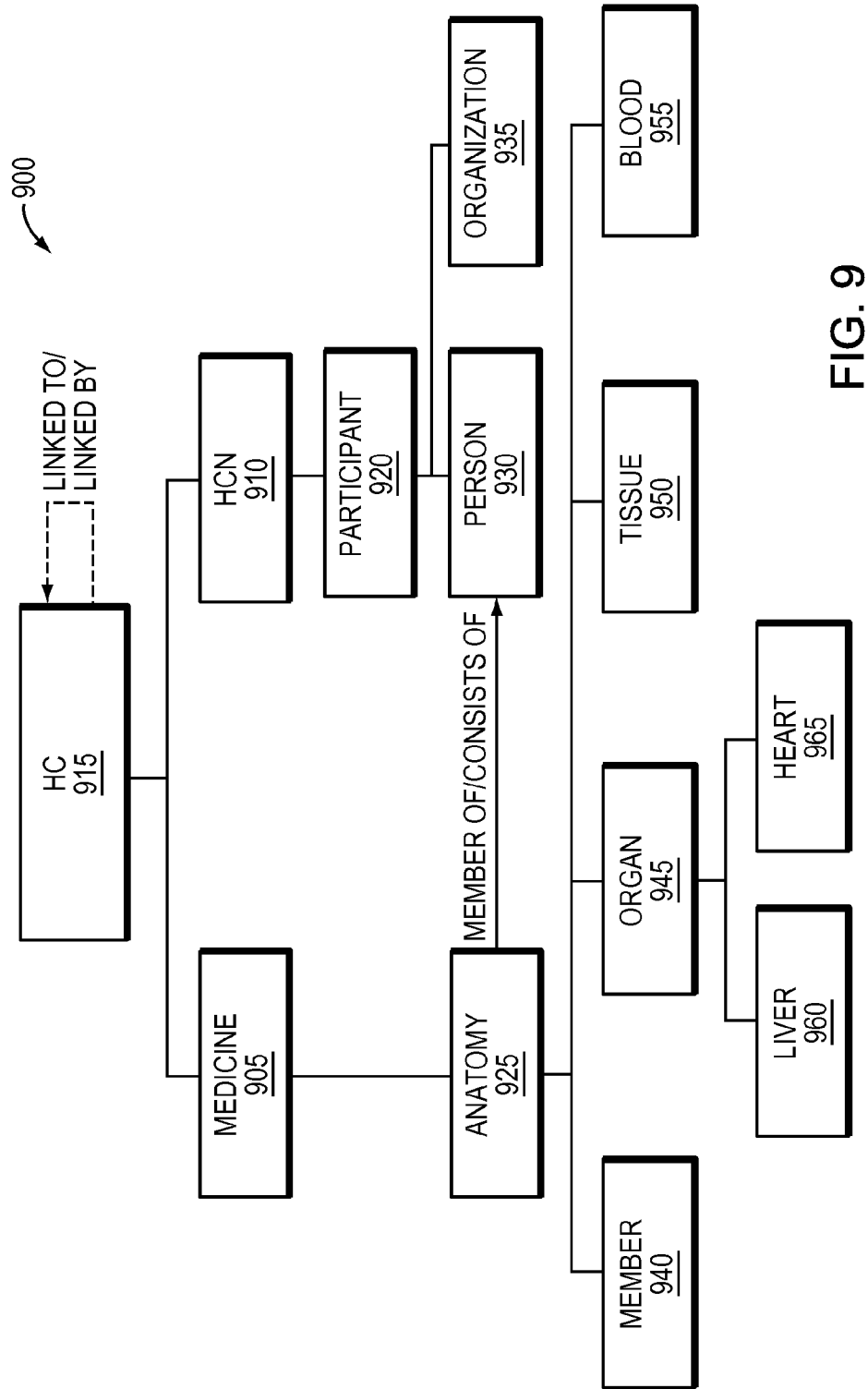
FIG. 9 is a simplified illustration of entities and relationships in a health care system model including a relationship between anatomy and person, in accordance with an embodiment of the present disclosure.

Refer now to the example embodiment of FIG. 9, which illustrates entities and relationships in a health care system model. Health care 905 has medicine 905 and health care network 910. Medicine is linked to/Composed in part/part of anatomy 920. Anatomy 920 has member 925, organ 930, tissue 935 and blood 940. Organ 930 has liver 945 and heart 950. Health care network 910 has participant 920. Participant 920 has person 930 and organization 935. Person 930 consists of anatomy 925.

Figure 10:
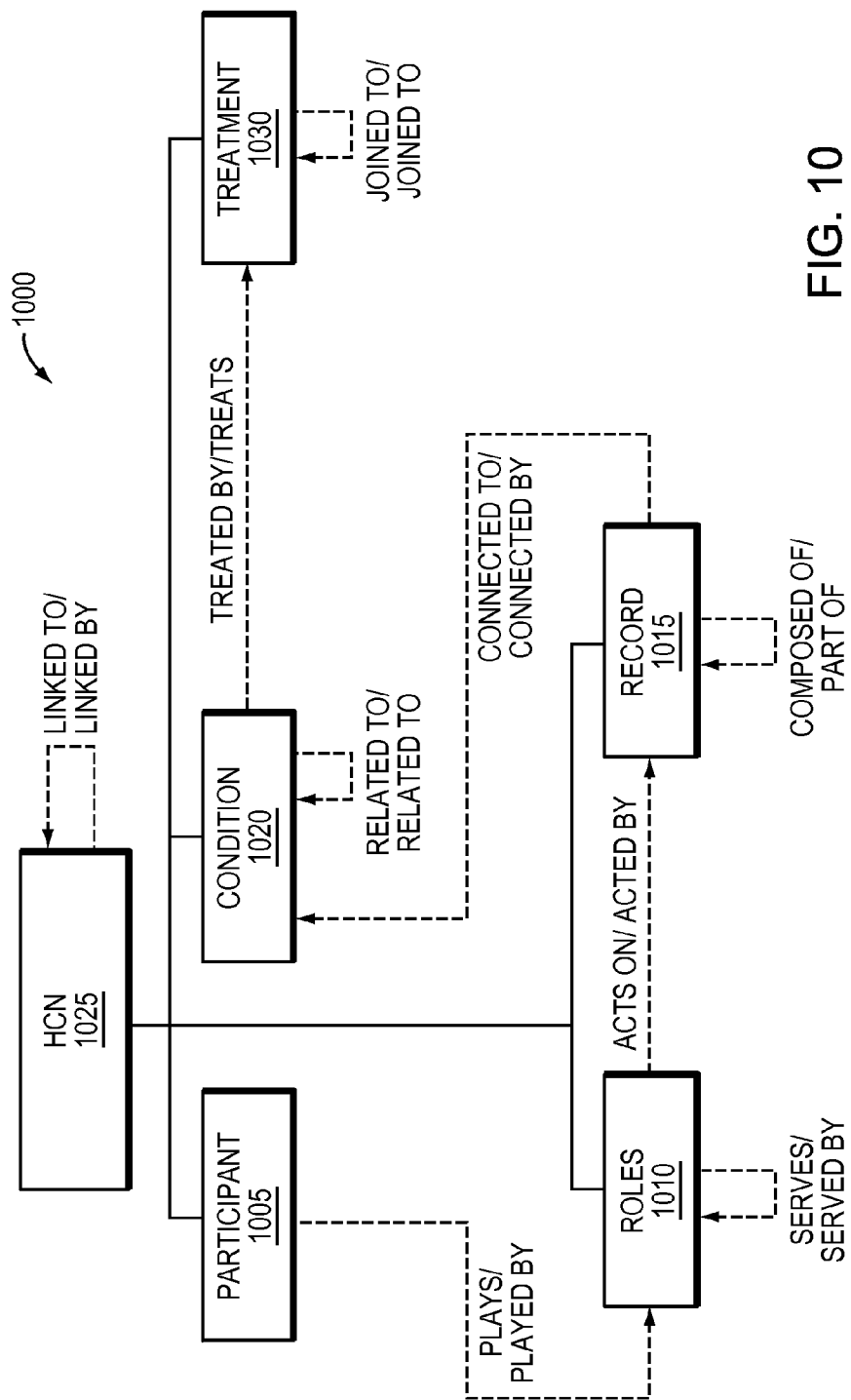
FIG. 10 is a simplified illustration of entities and relationships in a health care system model showing relationships between participant, roles, records, conditions, and treatment, in accordance with an embodiment of the present disclosure.

Refer now to the example embodiment of FIG. 10, which illustrates entities and relationships in a health care system model. In the example embodiment of FIG. 10, health care network 1025 has participant 1005 condition 1020 and treatment 1030. Participant 1005 plays roles 1010 and roles 1010 are played by participant 1005. Roles 1010 are acted on record 1015 and record 1015 is acted by roles 1010. Condition 1030 is treated by treatment 1030 and treatment 1030 is treats condition 1020. Condition 1020 is connected to record 1015.

Figure 11:
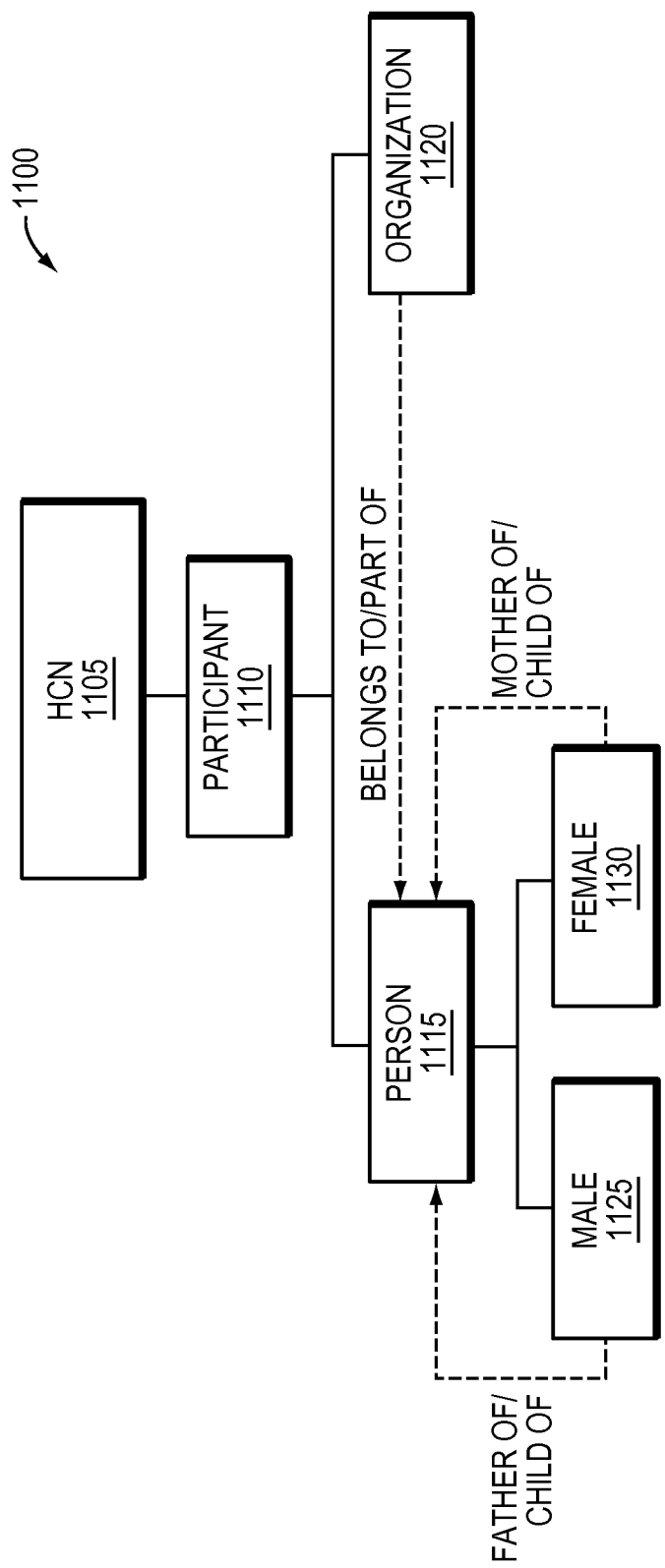
FIG. 11 is a simplified illustration of entities and relationships in a health care system model showing information about a person, in accordance with an embodiment of the present disclosure.

Refer now to the example embodiment of FIG. 11, which illustrates entities and relationships in a health care system model. In the example embodiment of FIG. 11, health care network 1105 has participant 1110. Participant 1000 has person 1115 and organization 1120. Person 1115 belongs to organization 1120. Person 1115 may be the child of male 1125 or female 1130. Male 1125 may be father of person 1115 and female 1130 may be the mother of person 1115.

Figure 12:
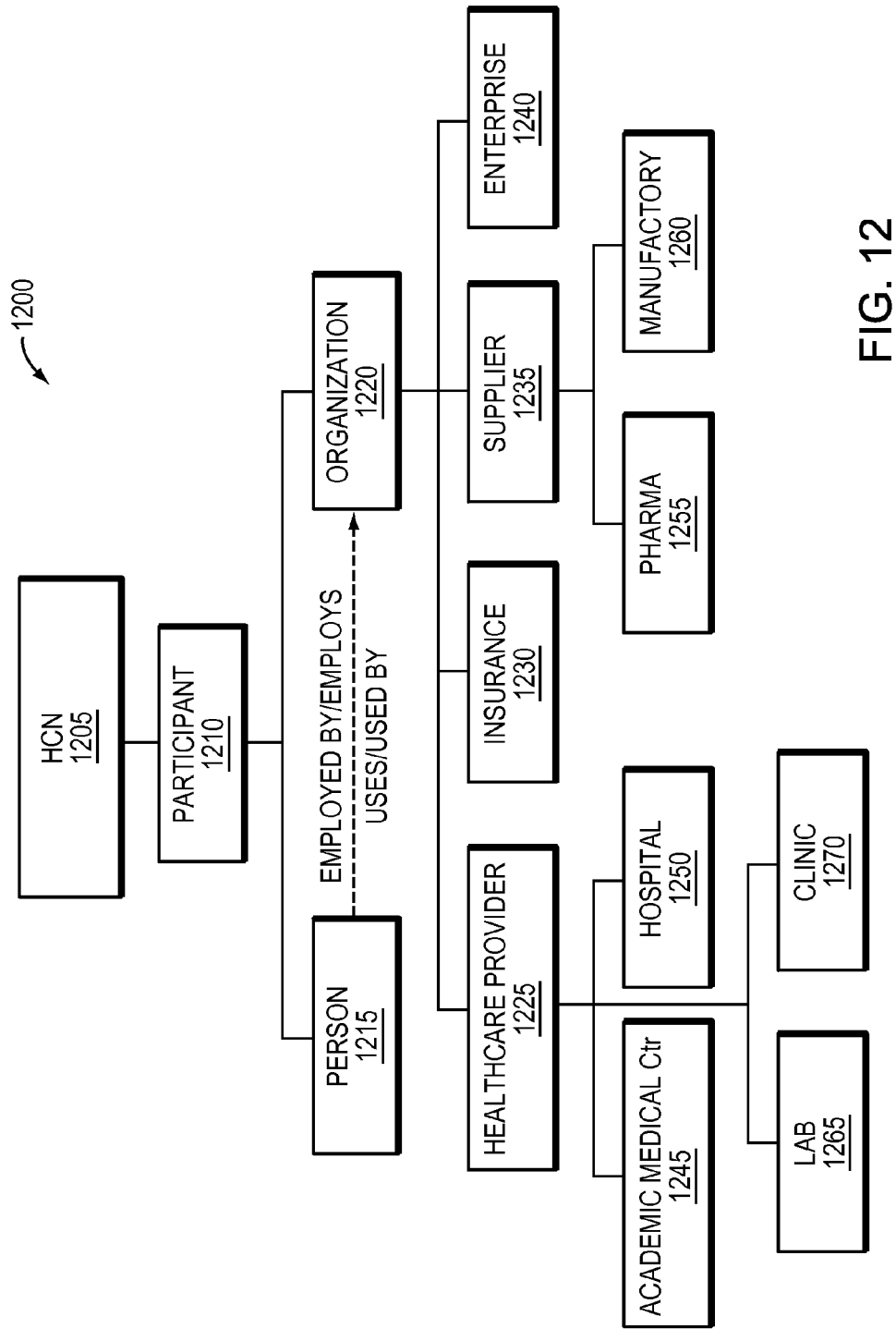
FIG. 12 is a simplified illustration of entities and relationships in a health care system model showing information about an organization, in accordance with an embodiment of the present disclosure.

Refer now to the example embodiment of FIG. 12, which illustrates entities and relationships in a health care system model. Health care network 1205 has participant 1210. Participant 1210 is composed of person 1215 and organization 1220. Person 1215 may be employed by organization 1220 and organization 1220 may employ person 1215. Organization 1230 includes of healthcare provider 1225, insurance 1230, supplier 1235, and enterprise 1240. Health care provider 1225 includes academic medical center 1245, hospital 1250, lab 1265, and clinic 1270. Supplier 1235 has pharmacy 1255 and manufacture 1260.

Figure 13:
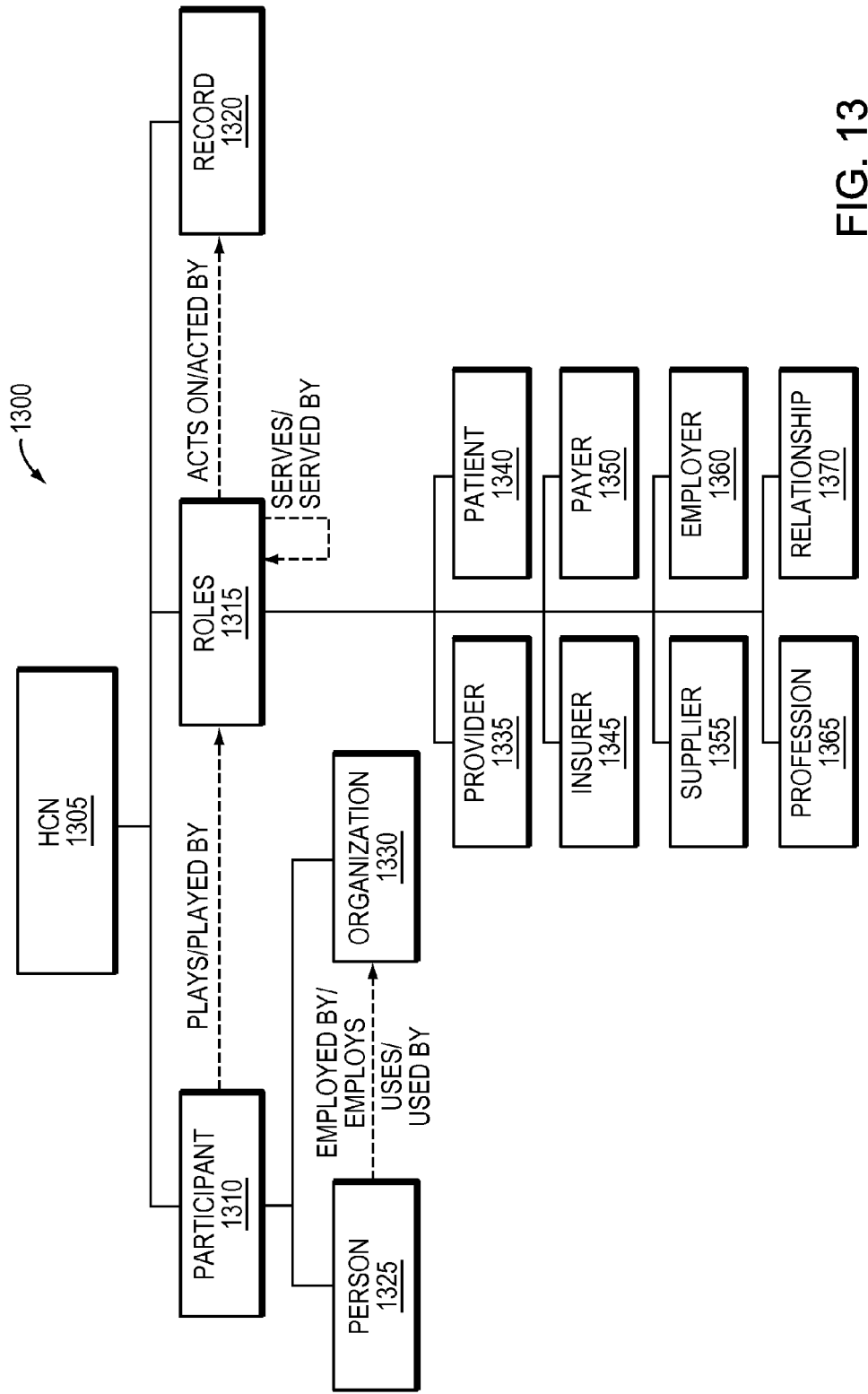
FIG. 13 is a simplified illustration of entities and relationships in a health care system model showing roles that may be served, in accordance with an embodiment of the present disclosure.

Refer now to the example embodiment of FIG. 13, which illustrates entities and relationships in a health care system model. In the example embodiment of FIG. 13, health care network 1305 has participant 1310 which pays roles 1315 which acts on record 1320. Participant 1310 has person 1325 which is employed by or uses organization 1330. Roles 1315 has provider 1335, patient 1340, insurer 1345, payer 1350, supplier 1355, employer 1360, profession 1365, and relationship 1370.

Figure 14:
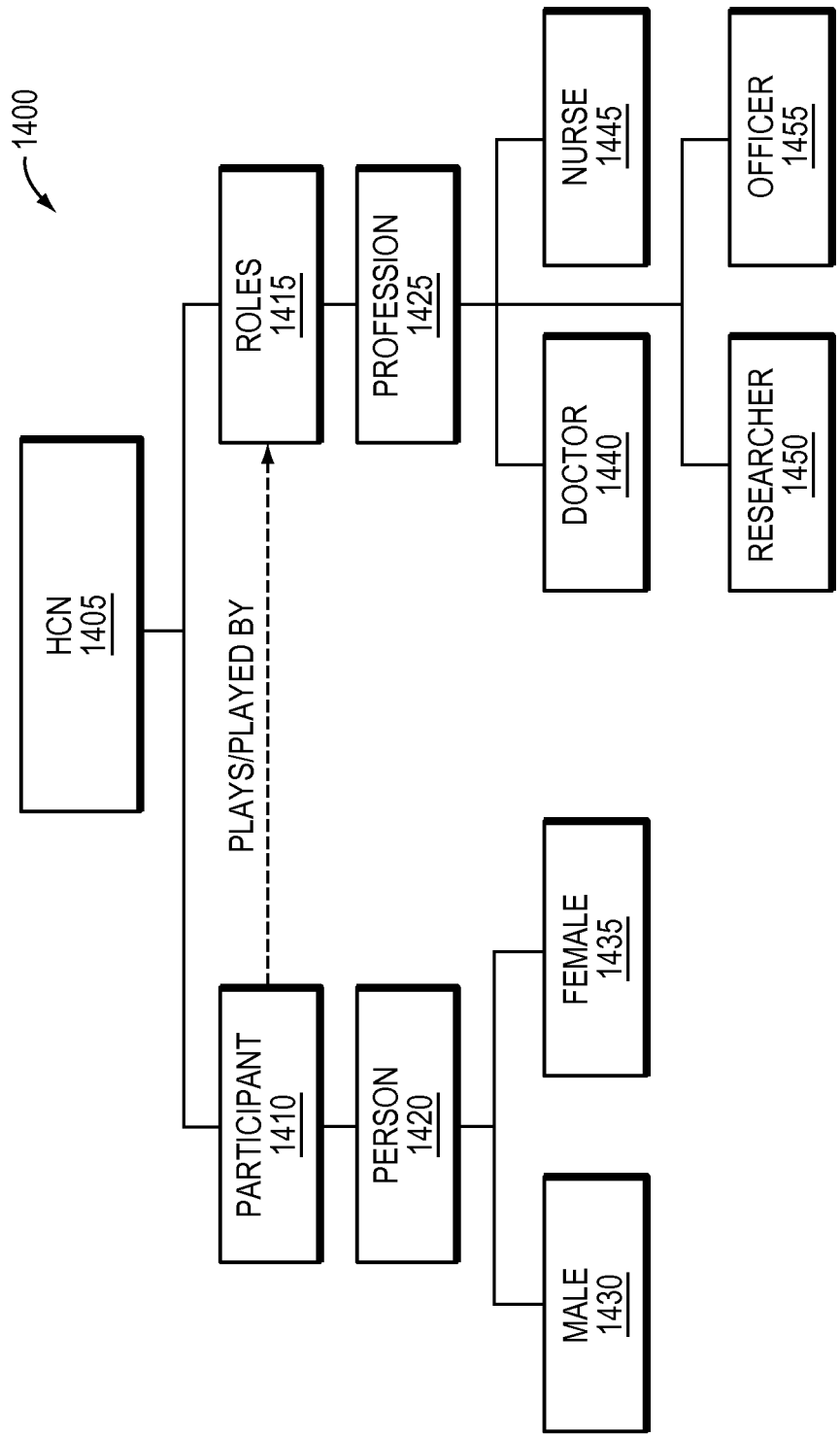
FIG. 14 is a simplified illustration of entities and relationships in a health care system model showing a link between a participant and roles, in accordance with an embodiment of the present disclosure.

Refer now to the example embodiment of FIG. 14, which illustrates entities and relationships in a health care system model. In the example embodiment of FIG. 14, health care network 1405 has patient 1410 which plays roles 1415. Patent 1410 has person 1420, which may be male 1430 or female 1435. Roles 1415 has profession 1425. Profession 1425 may be doctor 1440, nurse 1445, researcher 1450, or officer 1455.

Figure 15:
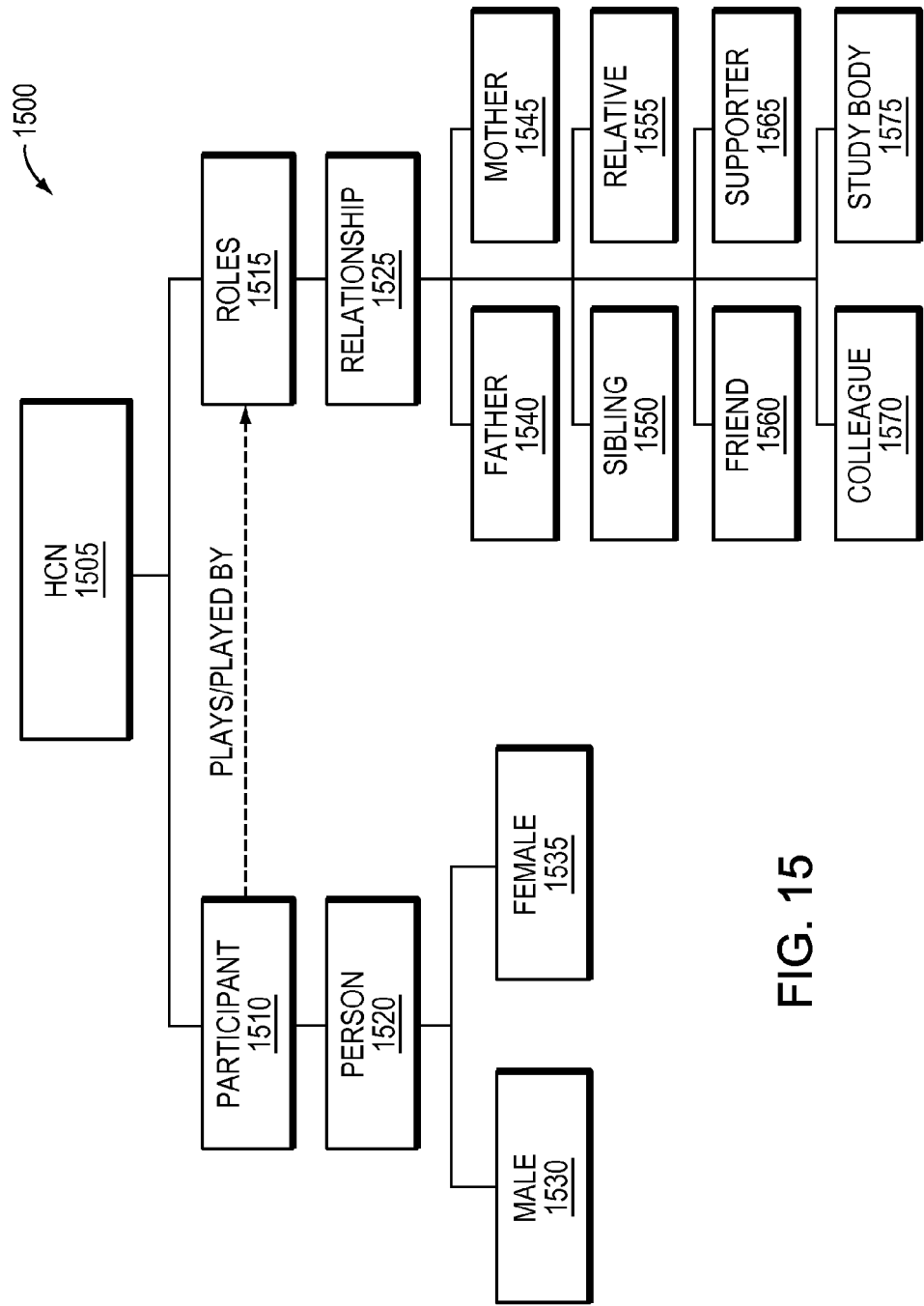
FIG. 15 is a simplified illustration of entities and relationships in a health care system model showing relationships, in accordance with an embodiment of the present disclosure.

Refer now to the example embodiment of FIG. 15, which illustrates entities and relationships in a health care system model. In the example embodiment of FIG. 15, health care network 1505 has participant 1510 which plays roles 11515. Participant 1510 may be person 1520, which may be male 1530 or female 1535. Roles 1515 has relationship 1525. Relationship 1525 may be father 1540, mother 1545, sibling 1550, relative 1555, friend 1560, supporter 1565, colleague 1570, and study body 1575.

Figure 16:
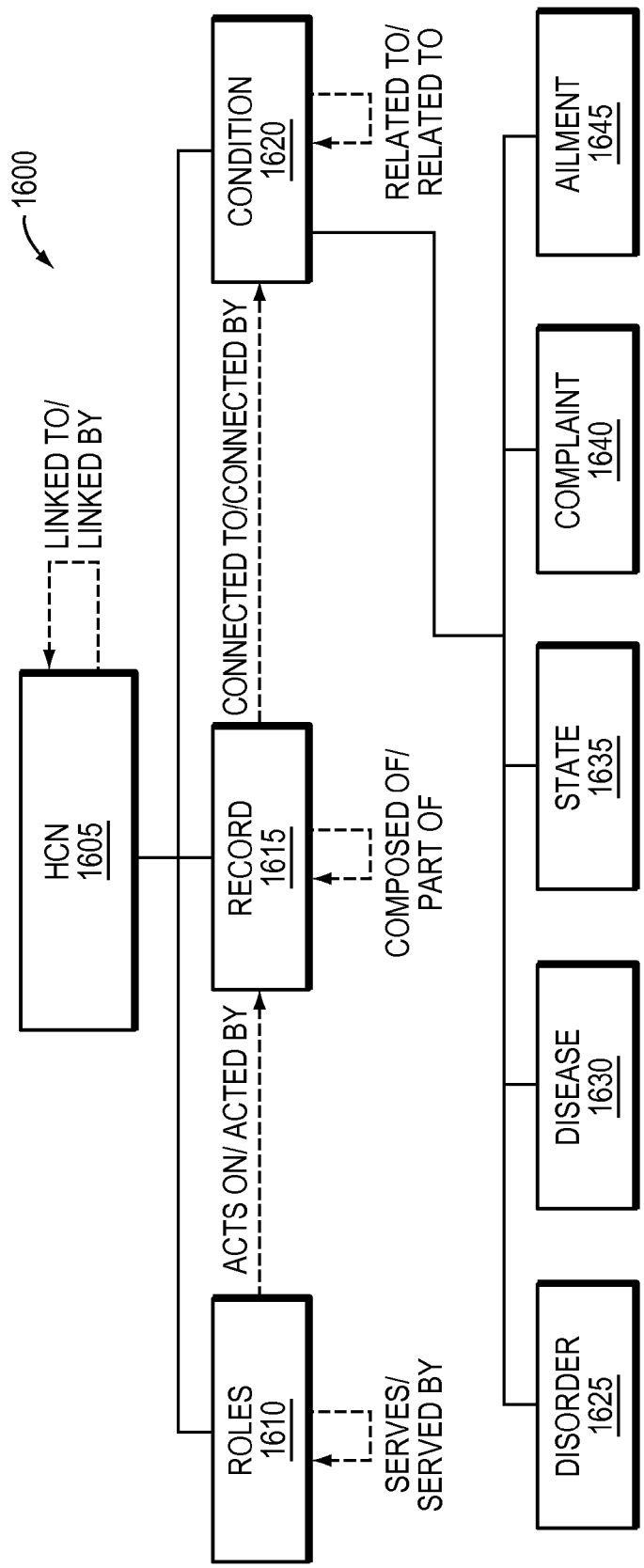
FIG. 16 is a simplified illustration of entities and relationships in a health care system mode showing conditions, in accordance with an embodiment of the present disclosure.

Refer now to the example embodiment of FIG. 16, which illustrates entities and relationships in a health care system model. In the example embodiment of FIG. 16, health care network 1605 has roles 1610 which acts on record 1615 which is connected to condition 1620. Condition 1620 has disorder 1625, disease 1630, state 1635, complaint 1640, and ailment 1645.

Figure 17:
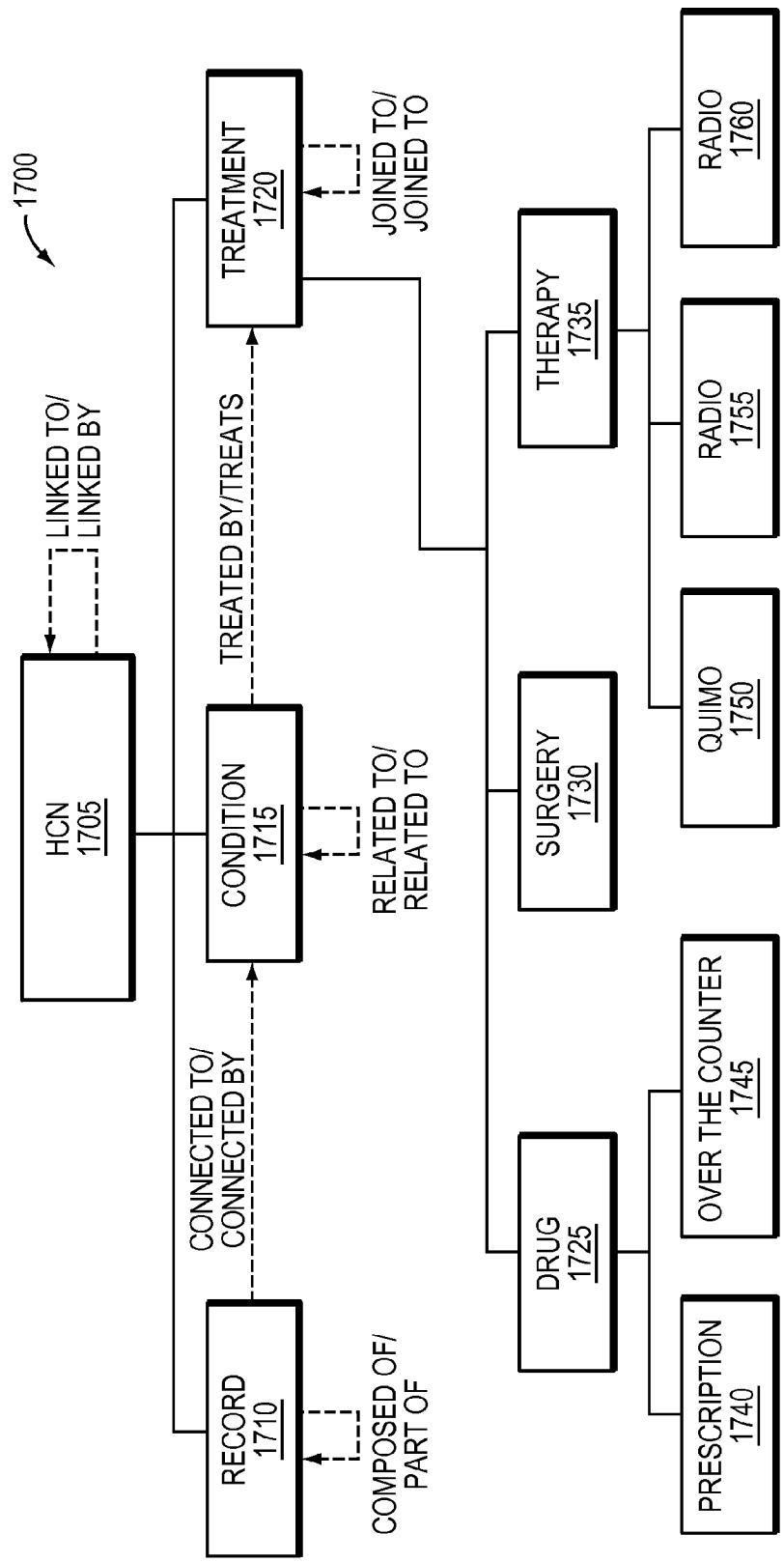
FIG. 17 is a simplified illustration of entities and relationships in a health care system model showing treatments, in accordance with an embodiment of the present disclosure.

Refer now to the example embodiment of FIG. 17, which illustrates entities and relationships in a health care system model. In the example embodiment of FIG. 17, health care network 1705 has record 1710 connected to condition 1715, which is treated by treatment 1720. Treatment 1720 may be drug 1725, surgery 1730, and therapy 1760. Drug 1725 may be prescription 1740 or over the counter 1745. Therapy 1735 may be quimo 1750, radio 1755, or ration 1760.

Figure 18:
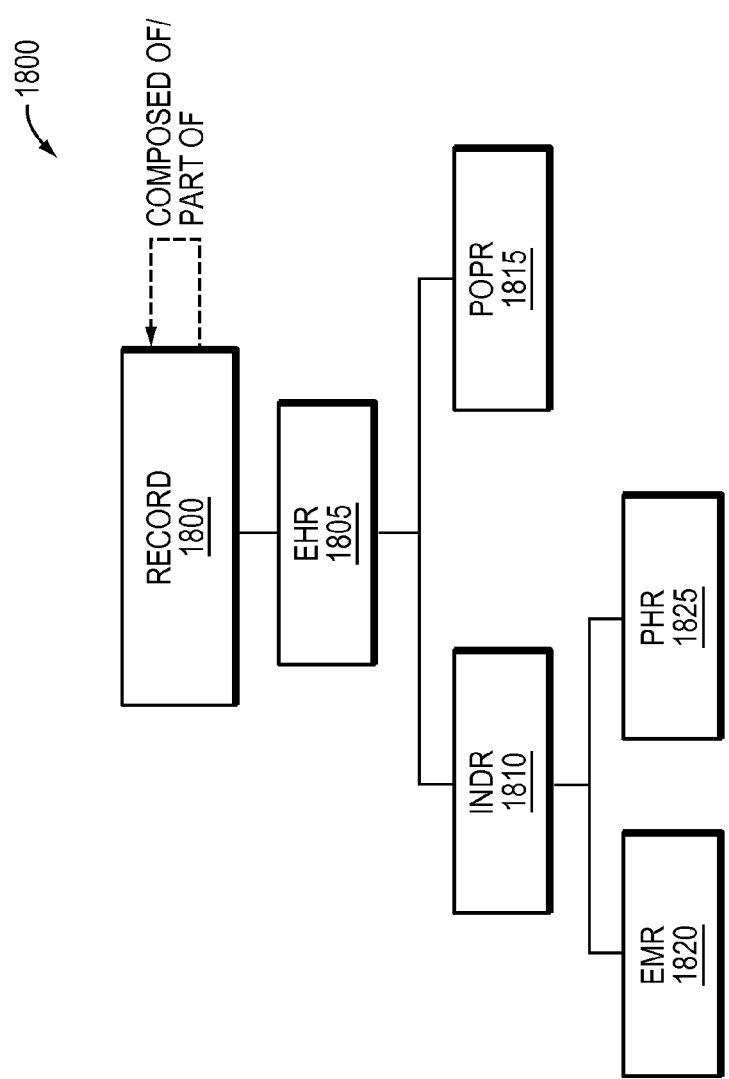
FIG. 18 is a simplified illustration of entities and relationships in a health care system model, in accordance with an embodiment of the present disclosure.

Refer now to the example embodiment of FIG. 18, which illustrates entities and relationships in a health care system model. In the example embodiment of FIG. 18, record 1800 has electronic health record 1805. Electronic health record 1805 may be individual patients (INDR) 1810 or populations (POPR) 1815. INDR 1810 may be Electronic medical record 1820 or Personal Health record 1825.

Figure 19:
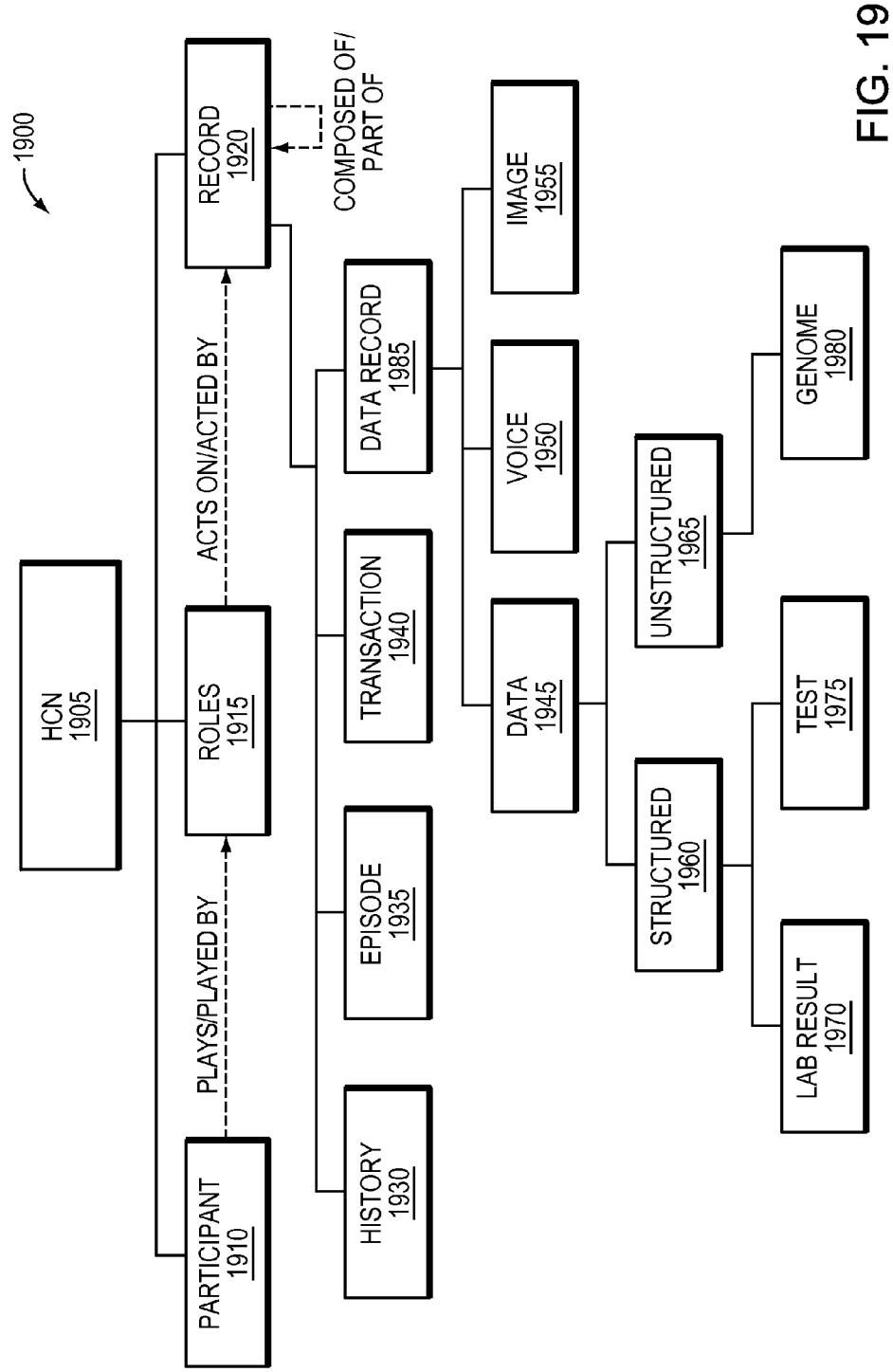
FIG. 19 is a simplified illustration of entities and relationships in a health care system model showing record information, in accordance with an embodiment of the present disclosure.

Refer now to the example embodiment of FIG. 19, which illustrates entities and relationships in a health care system model. In the example embodiment of FIG. 19, health care network 1905 has participant 1910 which plays roles 1915, which acts on record 1920. Record 1920 has history 1920, episode 1935, transaction 1940, and data record 1985. Data record 1985 has data 1945, voice 1950, and image 1955. Data 1945 may be structured 1960 or unstructured data 1964. Unstructured data may have genome 1980. Structured data 1960 may have lab result 1970 and test 1975.

Figure 20:
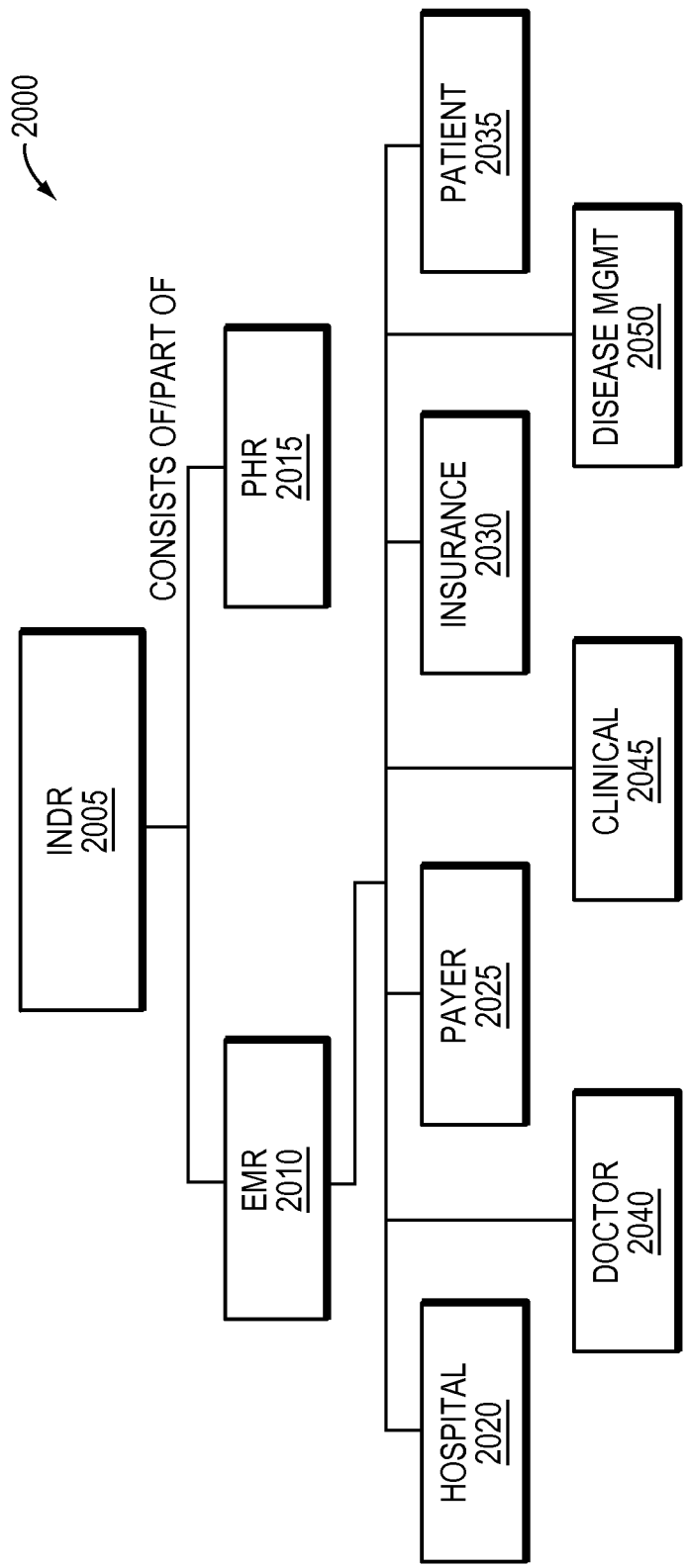
FIG. 20 is a simplified illustration of entities and relationships in a health care system model, in accordance with an embodiment of the present disclosure.

Refer now to the example embodiment of FIG. 20, which illustrates entities and relationships in a health care system model. INDR 2005 may consist of electronic medical record (EMR) 2010 and personal health record (PHR) 2015. EMR 2010 may have hospital 2020, payer 2025, insurance, 2030, patient 2035, doctor 2040, clinical 2045, and disease management information 2050.

Figure 21:
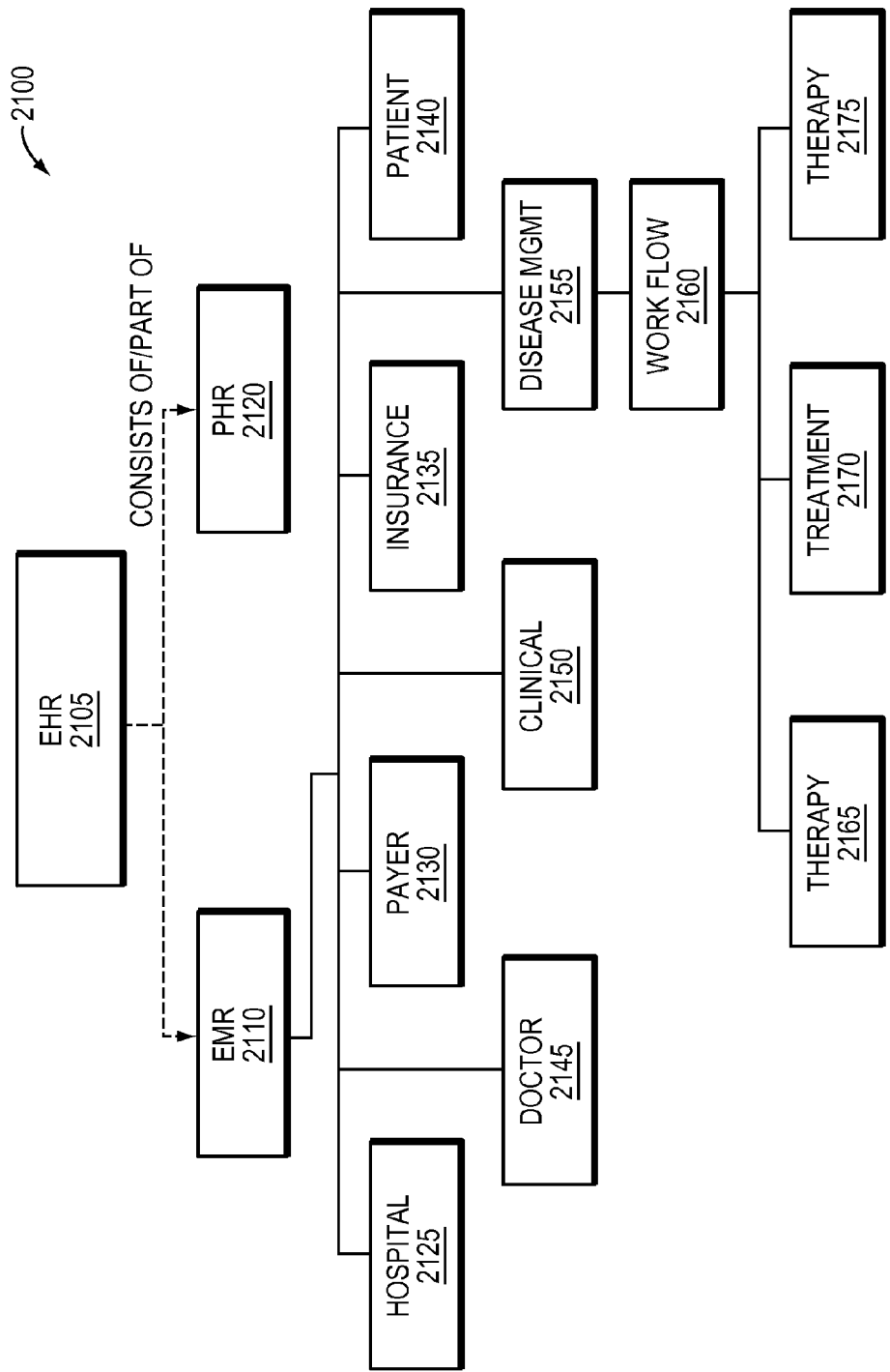
FIG. 21 is a simplified illustration of entities and relationships in a health care system model showing disease management, in accordance with an embodiment of the present disclosure.

Refer now to the example embodiment of FIG. 21, which illustrates entities and relationships in a health care system model. In the example embodiment of FIG. 21 electronic health record 2105 may have electronic medical record 2110 and personal health record 2120. electronic medical record 2110 may have hospital 2120, payer 2125, insurance, 1030, patient 2135, doctor 2140, clinical 2145, and disease management information 2150. Disease management 2155 may have work flow 2160. Workflow 2160 may have therapy 2165, treatment 2170, and therapy 2175.

Figure 22:
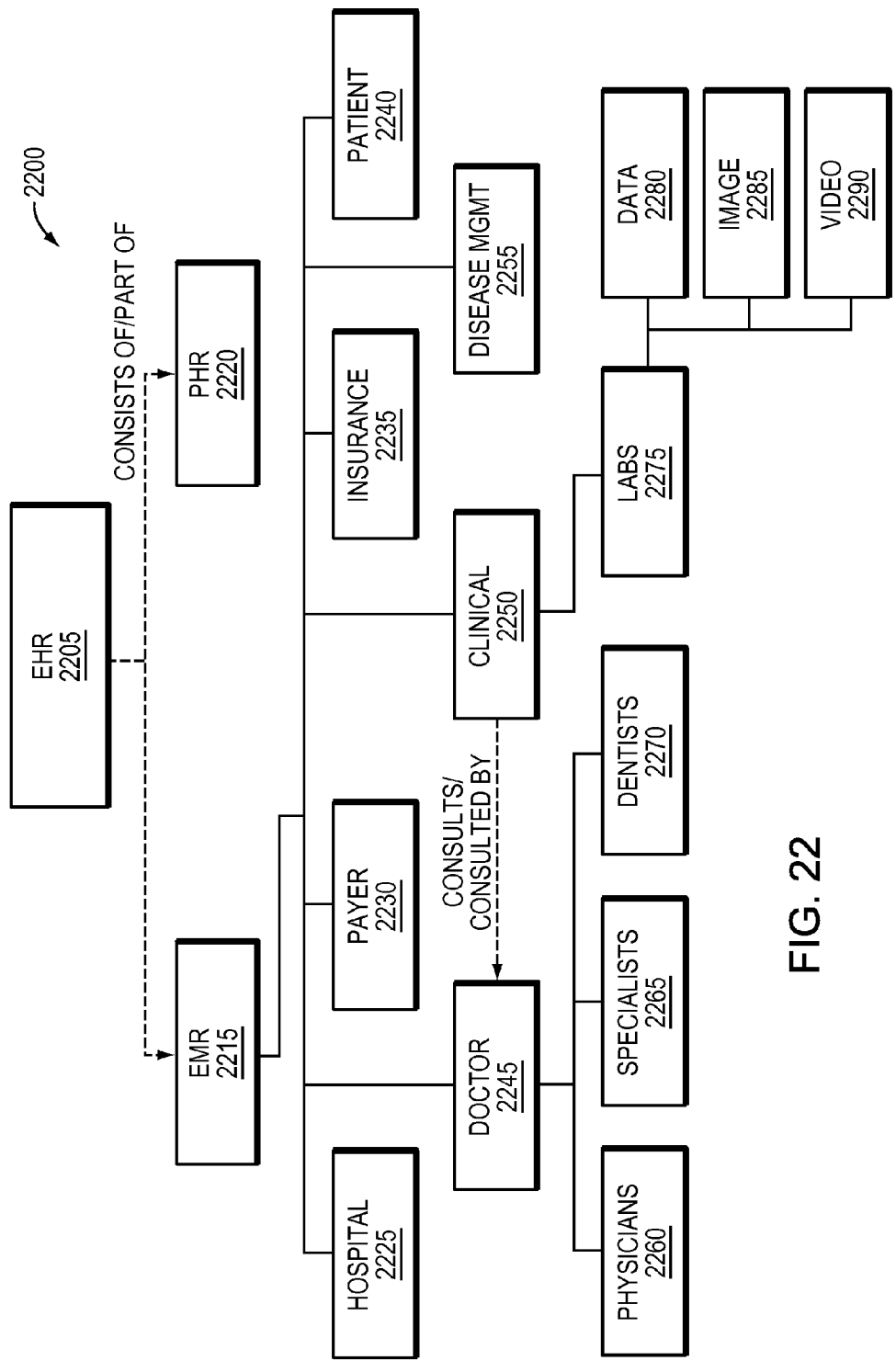
FIG. 22 is a simplified illustration of entities and relationships in a health care system model showing types of doctors, in accordance with an embodiment of the present disclosure.

Refer now to the example embodiment of FIG. 22, which illustrates entities and relationships in a health care system model. In the example embodiment of FIG. 22 electronic health record 2205 may have electronic medical record 2215 and personal health record 2220. EMR 2215 may have hospital 2225, payer 2230, insurance, 2235, patient 2240, doctor 2245, clinical 2250, and disease management information 2255. Clinical 2250 has labs 2275, which has data 2280, image 2285, and video 2290. Doctor 2245 may have or consist of physicians 2260, specialists 2265, and dentists 2270.

Figure 23:
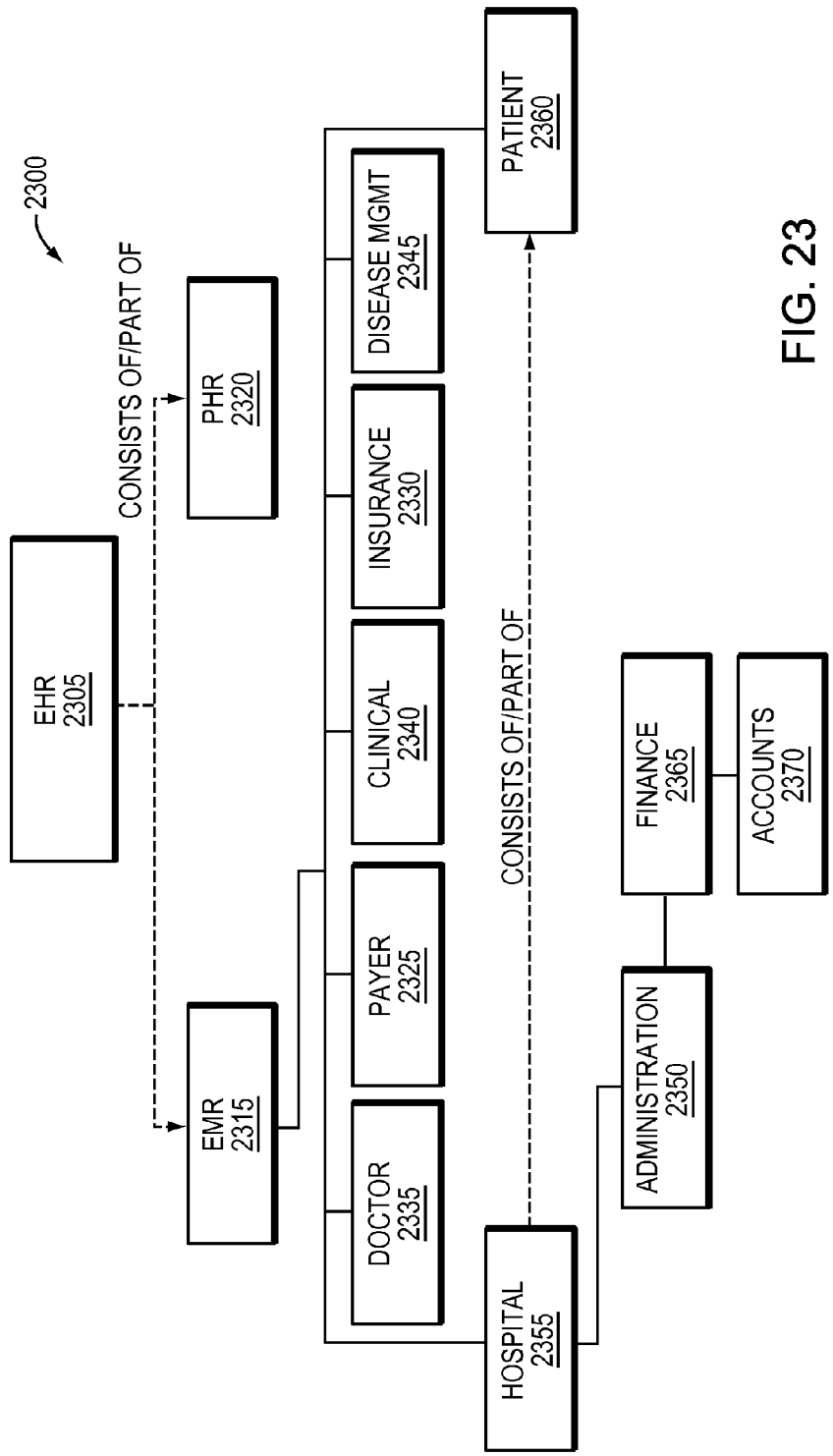
FIG. 23 is a simplified illustration of entities and relationships in a health care system model showing hospital administration, in accordance with an embodiment of the present disclosure.

Refer now to the example embodiment of FIG. 23, which illustrates entities and relationships in a health care system model. In the example embodiment of FIG. 23, electronic health record has electronic medical record 2314 and personal health record 2320. Electronic medical record (EMR) 2315 has hospital 2355, which consists of patient 2360. Hospital 2355 has administration 2350, which has finance 2365 and accounts 2370. EMR 2315 also has doctor 2335, payer 2325, clinical 2340, insurance 2330, patient 2360, and disease management 2345.

Figure 24:
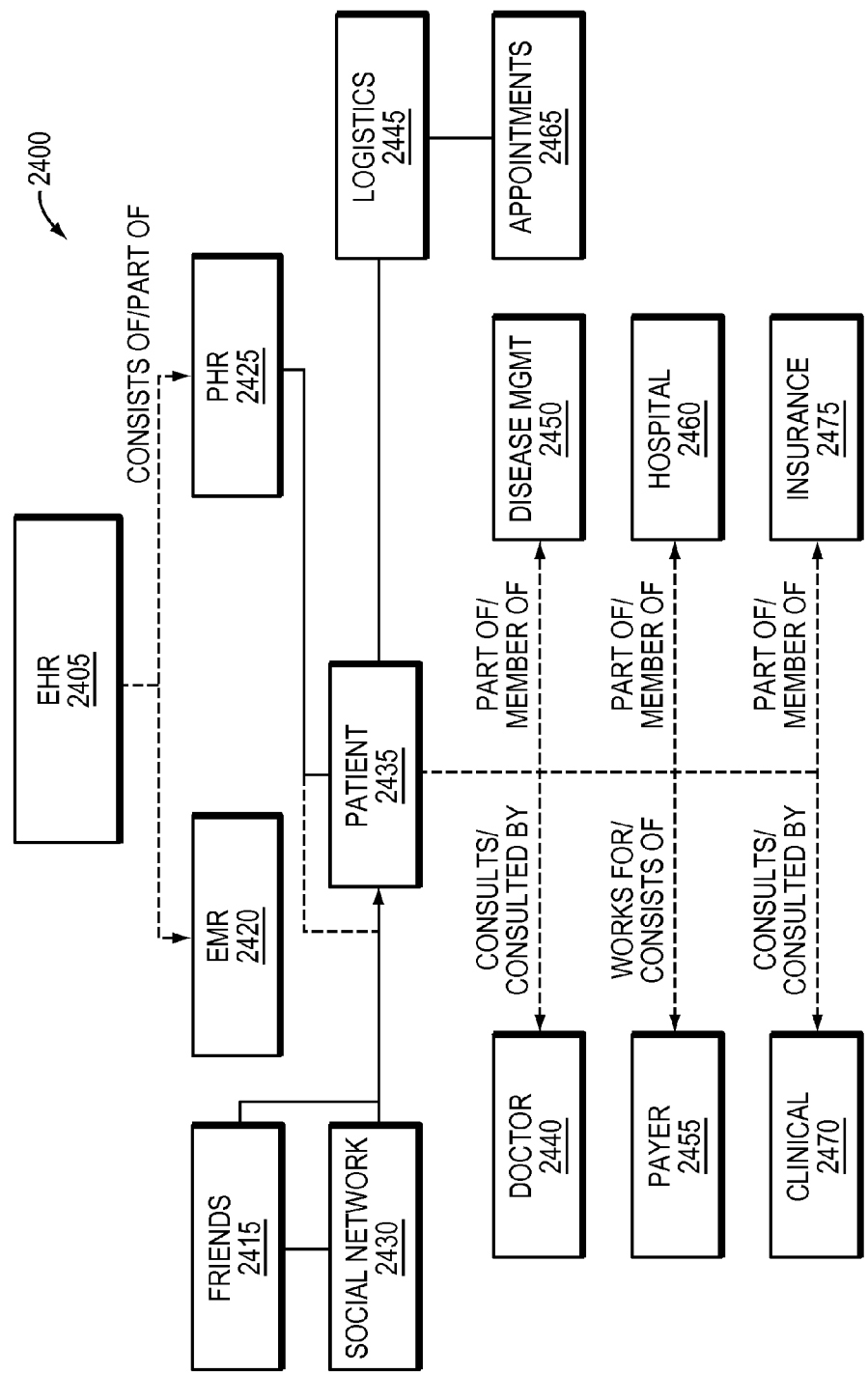
FIG. 24 is a simplified illustration of entities and relationships in a health care system model showing relationships between a patient, in accordance with an embodiment of the present disclosure.

Refer now to the example embodiment of FIG. 24, which illustrates entities and relationships in a health care system model. In the example embodiment of FIG. 24, electronic health record 2405 consists of electronic medical record 2420 and personal health record 2425. Personal health record 2425 has patient 2435. Patient 2435 has friends 2415 and social network 2430. Patient 2435 is connected to logistics 2445, which has appointments 2465. Patient 2435 may be consulted by doctor 2440. Patient 2435 may be part of disease management 2450. Patient 2435 may work for payer 2455. Patient 2435 may be part of hospital 2460. Patient 2435 may consult with clinical 2470. Patient 2435 may be part of insurance 2475.

Figure 25:
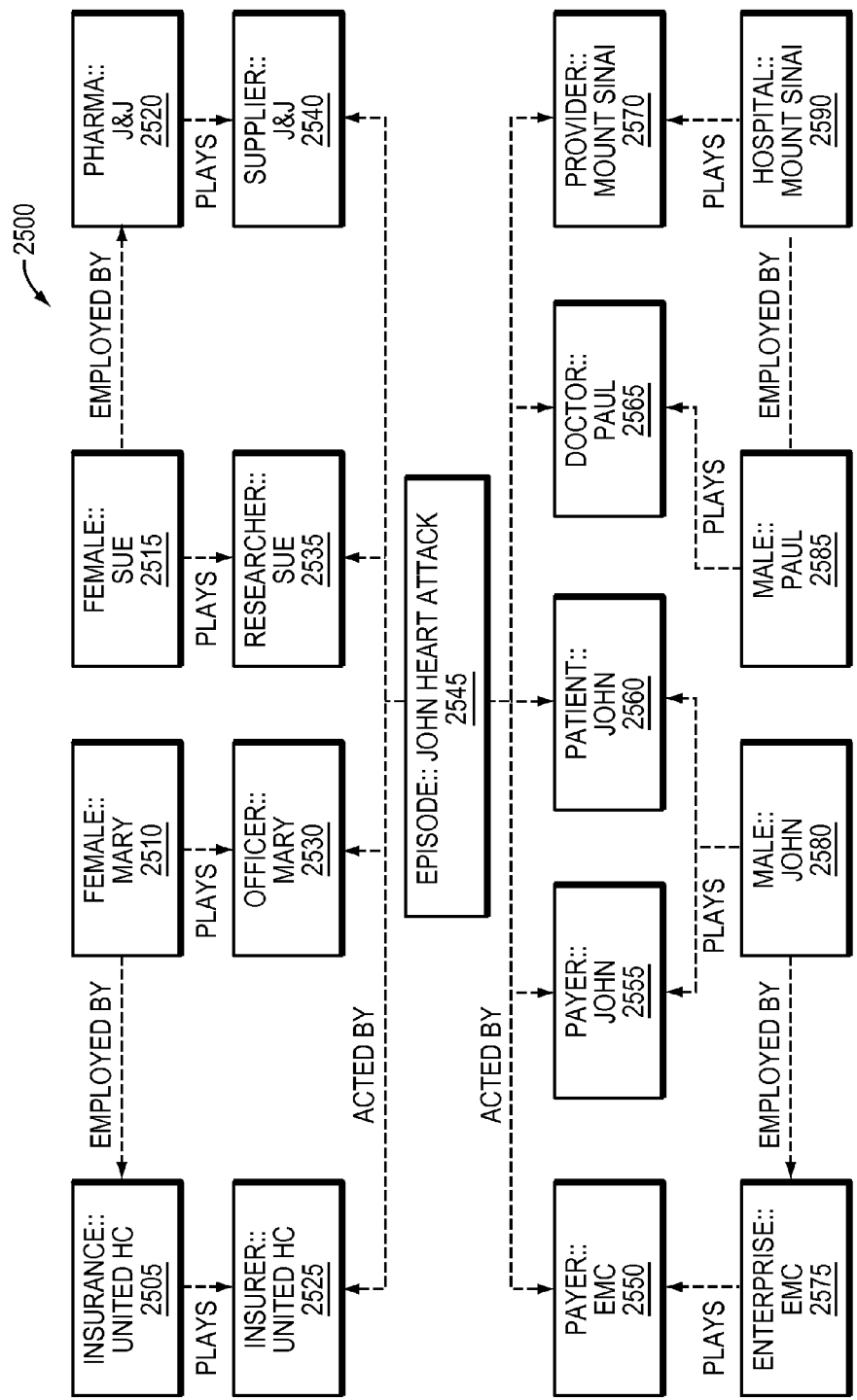
FIG. 25 is a simplified illustration of a sample topology showing relationships between objects in a model, in accordance with an embodiment of the present disclosure.

Refer now to the example embodiment of FIG. 25, which illustrates a sample topology showing relationships between objects in a model. In the example embodiment of FIG. 25, Female::Mary 2510 is employed by Insurance::United HC 2505. Insurance 2505 plays insurer::united health care 2525. Female::Mary 2510 plays officer::Mary 2530. Female::Sue 2515 is employed by pharma::J&J 2520. Pharma::J&J 2520 plays supplier::J&J 2540. Female::Sue 2515 plays researcher::sue 2535. Episode::John heart attack 2545 is acted on by insurer::united HC 2525, Officer::Mary 2530, Researcher::Sue 2535, and supplier::J&J 2540. Episode::John Heart Attack 2545 is also acted by payer::EMC 2550, payen:john 2555, Patient:John 2560, doctor::Paul 2565, and provider:: Mount Sinai 2570. Enterprise::EMC 2575 plays payer:: EMC 2550 and employs Male::John 2580. Male::John 2580 plays payer::John 2555 and patient::John 2560. Male::Paul 2585 plays Doctor::Paul 2565 and is employed by hospital:: Mount Sinai 2590 which plays Provider::Mount Sinai 2570.

Figure 26:
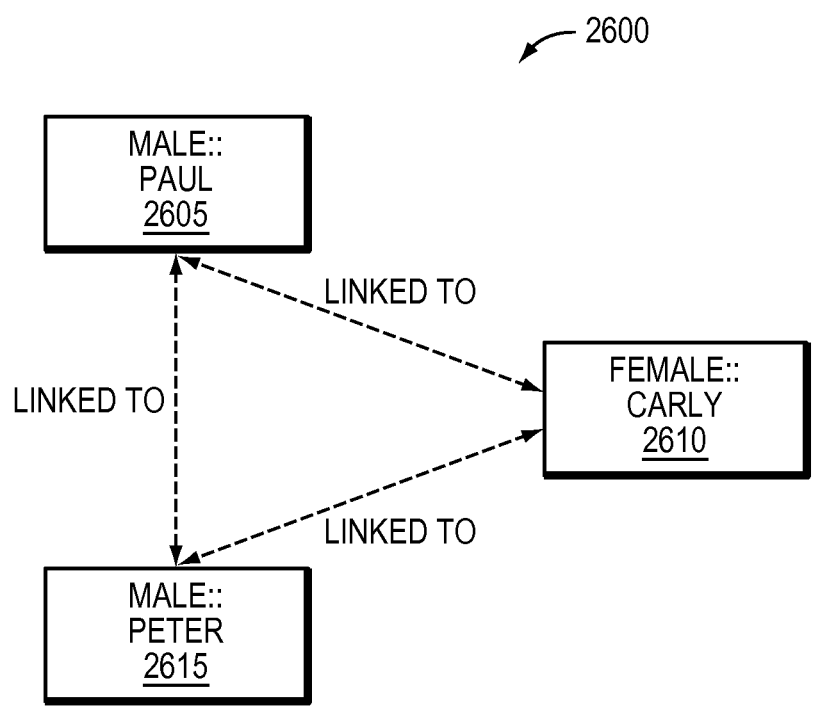
FIG. 26 is an alternative simplified illustration of a sample topology showing relationships between objects in a model, in accordance with an embodiment of the present disclosure.

Refer now to the example embodiment of FIG. 26, which illustrates a sample topology showing relationships between objects in a model. In this example embodiment, Male::Paul 2605 is bi-directionally linked to female::Carly 2610 and Male::Peter 2615. Similarly, Male::Peter 2615 is bi-directionally linked to Female::Carly 2620.

Figure 27:
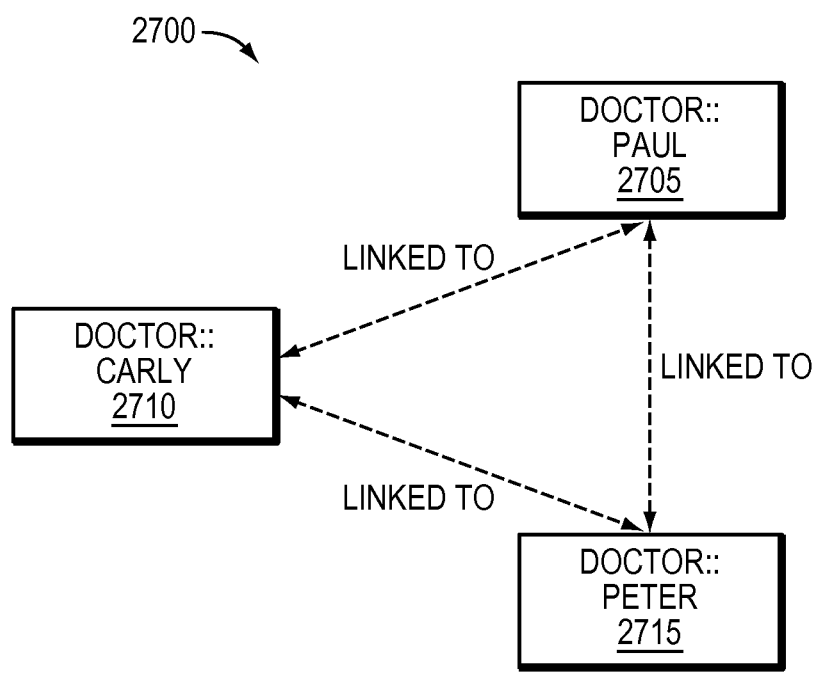
FIG. 27 is a further alternative simplified illustration of a sample topology showing relationships between objects in a model, in accordance with an embodiment of the present disclosure.

Refer now to the example embodiment of FIG. 27, which illustrates a sample topology showing relationships between objects in a model. Doctor::Carly 2710 is bi-directionally linked to doctor::Paul 2705 and Doctor::Peter 2715. As well, Doctor::Paul 2705 is bi-directionally linked to Doctor::Peter 2715.

Figure 28:
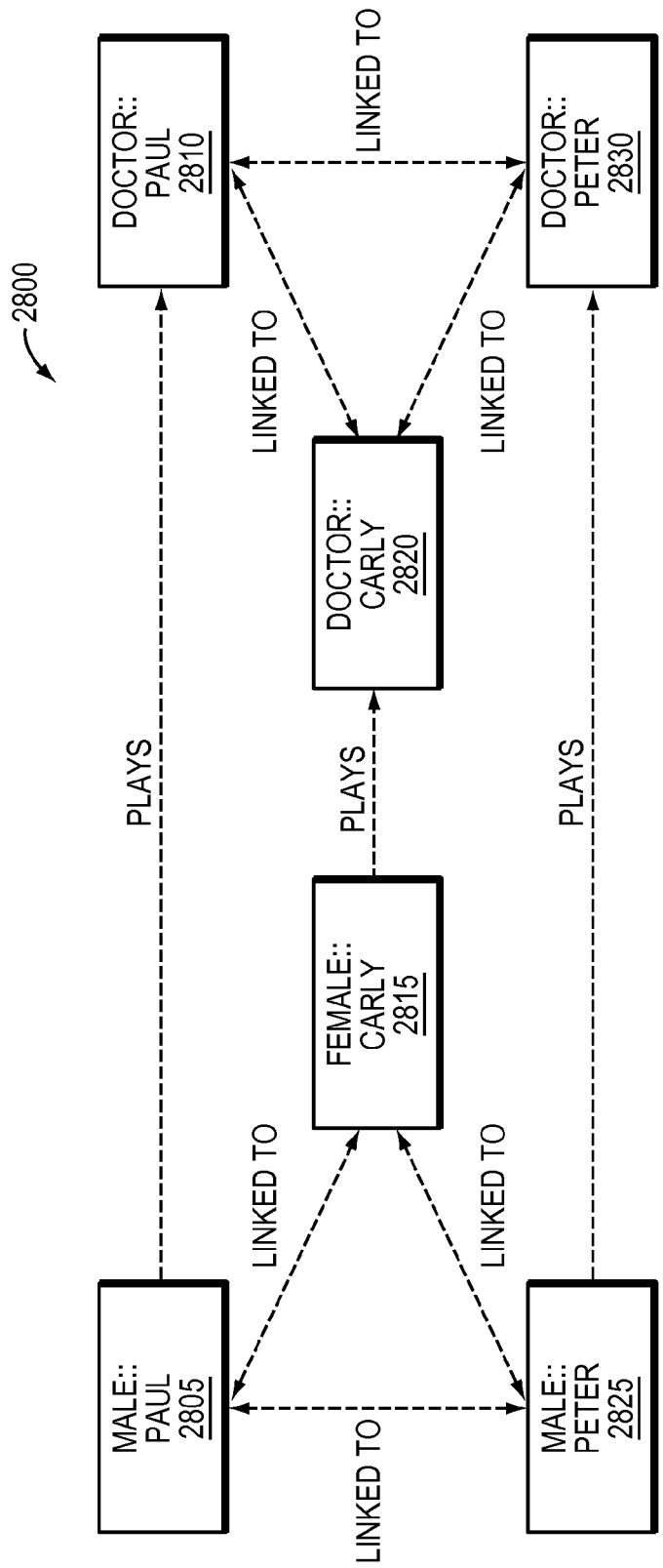
FIG. 28 is a simplified illustration of a combination of FIGS. 26 and 27 into a common topology, in accordance with an embodiment of the present disclosure.

Refer now to the example embodiment of FIG. 28, which represents a combination of FIGS. 26 and 27 into a common topology. Female::Carly 2815 plays Doctor::Carly 2820. Female::Carly 2815 has bi-directionally links to Male:: Paul::2805 and Male Peter::2825. Doctor::Carly 2820 has bi-directionally links to Doctor::Peter 2830 and Doctor:: Paul 2810. Male::Paul 2805 is bi-directionally linked to Male::Peter 2825. Doctor::Paul 2810 is bi-directionally linked to Doctor::Peter 2830.

Figure 29:
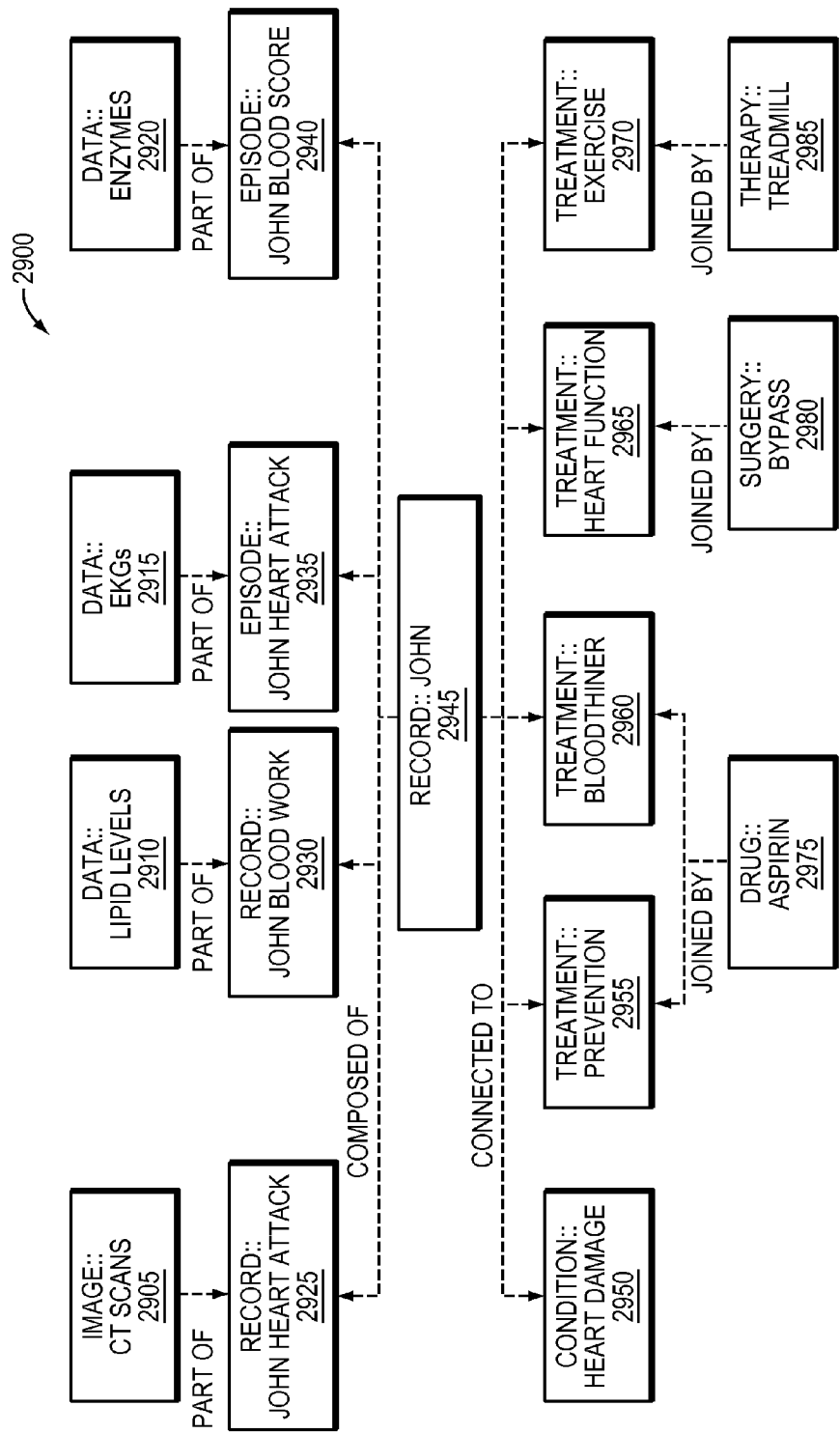
FIG. 29 is a simplified illustration of a sample health care network, in accordance with an embodiment of the present disclosure.

Refer now to the example embodiment of FIG. 29, which illustrates a sample health care network. In the example of FIG. 29, Record::John 2945 is composed of Record::John Heart attack 2925, Record::John Blood Work 2930, Episode::John Heart attack 2935, and episode::John Blood Score 2950. Image::CT Scans 2905 are part of Record::John Heart Attack 2925, Data::Lipid Levels 2910 are part of Record::John Blood Work 2930. Data::EKG 2915 is part of Episode::John Heart attack 2935. Data::Enzymes 2920 are part of Episode::John Blood Score 2940. Record::John 2945 is connected to condition::Heart damage 2950, treatment:: prevention 2955, treatment::blood thinner 2960, treatment:: heart function 2965, and treatment::exercise 2970. Drug:: Aspirin 2975 is joined by treatment::Prevention 2955 and treatment::blood thinner 2960.

Figure 30:
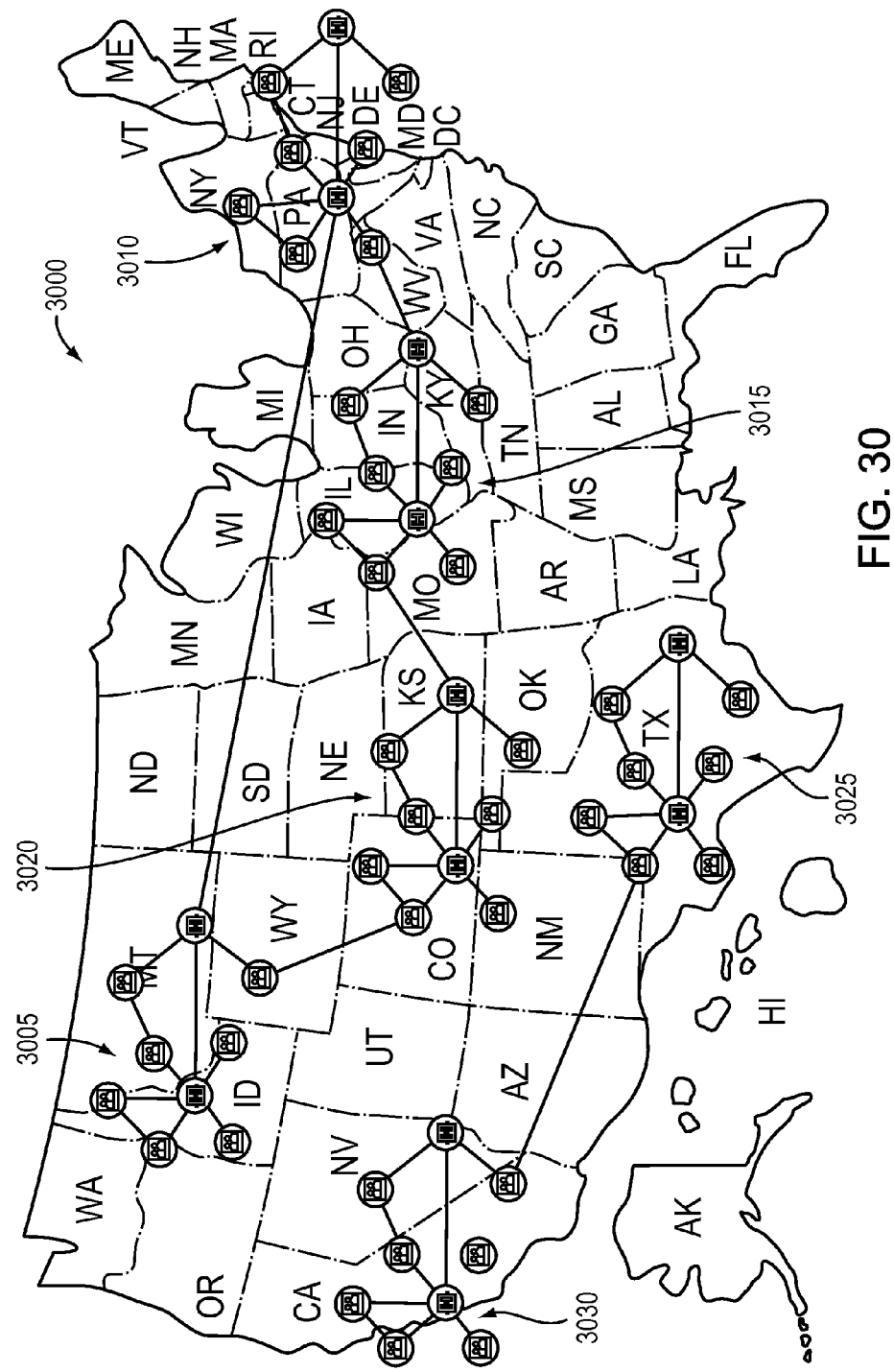
FIG. 30 is a simplified illustration of a topology overlaid on a geographic area, in accordance with an embodiment of the present disclosure.

Refer now to the example embodiment of FIG. 30, which illustrates a topology overlaid on a geographic area. In this example embodiment, map 3000 represents a geographic location. Health care network elements 53005, 3010, 3015, 3020, 3025, and 3030 are overlaid on map 3000.

Figure 31:
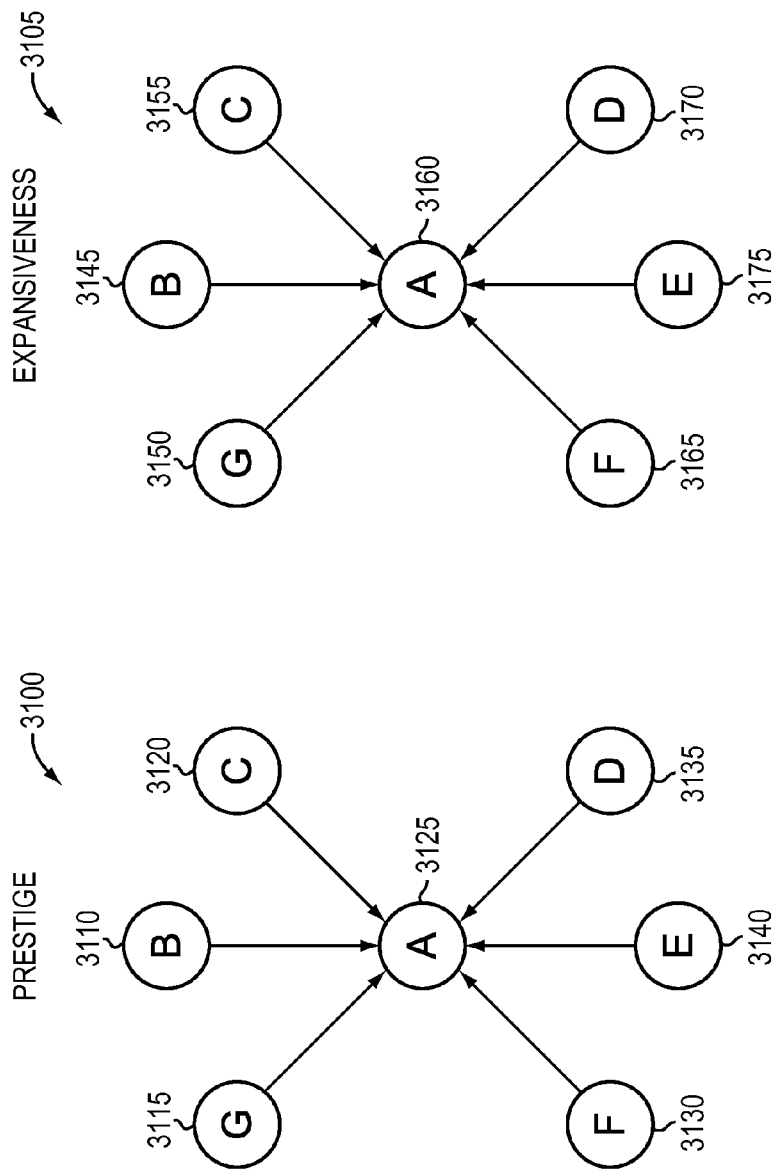
FIG. 31 is a simplified illustration of prestige and expansiveness, in accordance with an embodiment of the present disclosure.

Refer now to the example embodiment of FIG. 31, which illustrates prestige and expansiveness. In FIG. 31, Prestige 3100 may be denoted by the number of connections to an element. Elements B, 3110, C 3120, D 3135, E 3140, F 3130, and G 3115 all have connections to element A 3125. Expansiveness may be defined by the number of connections from an element. Element A 3160 has outward connections to elements B 3145, C 3155, D 3170, E 3175, F 3165, and G 3150.

Figure 32:
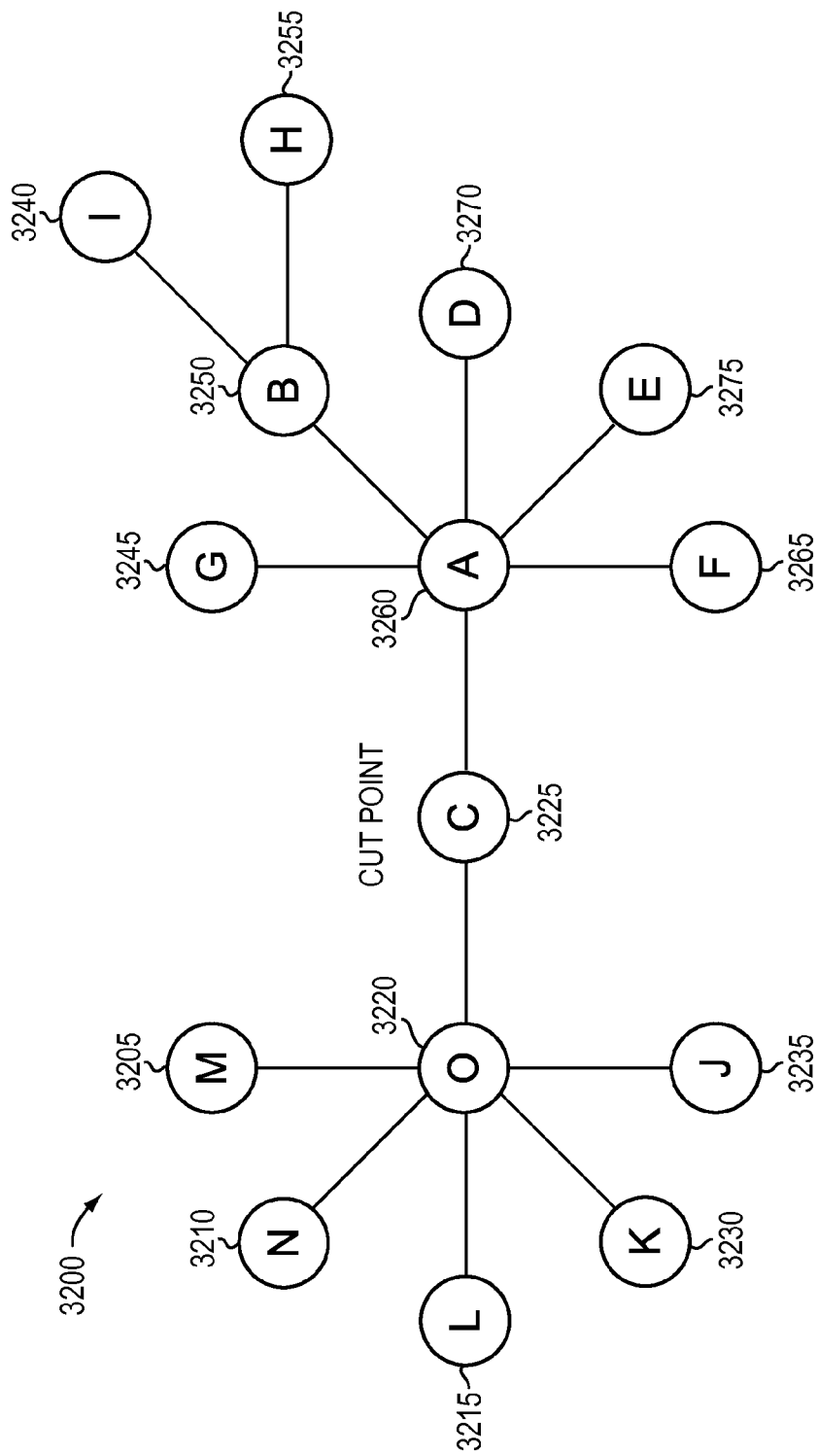
FIG. 32 is a simplified illustration of a cut point, in accordance with an embodiment of the present disclosure.

Refer now to the example embodiment of FIG. 32, which illustrates a cut point. Element C 3225 is the cut point between the network of O 3220, M3205, N 3210, L 3215, K 3230, and J 3235 and the network of elements A 3260, G 3245, F 3265, E 3275, B 3250, D 3270, H 3255, and I 3240.

Figure 33:
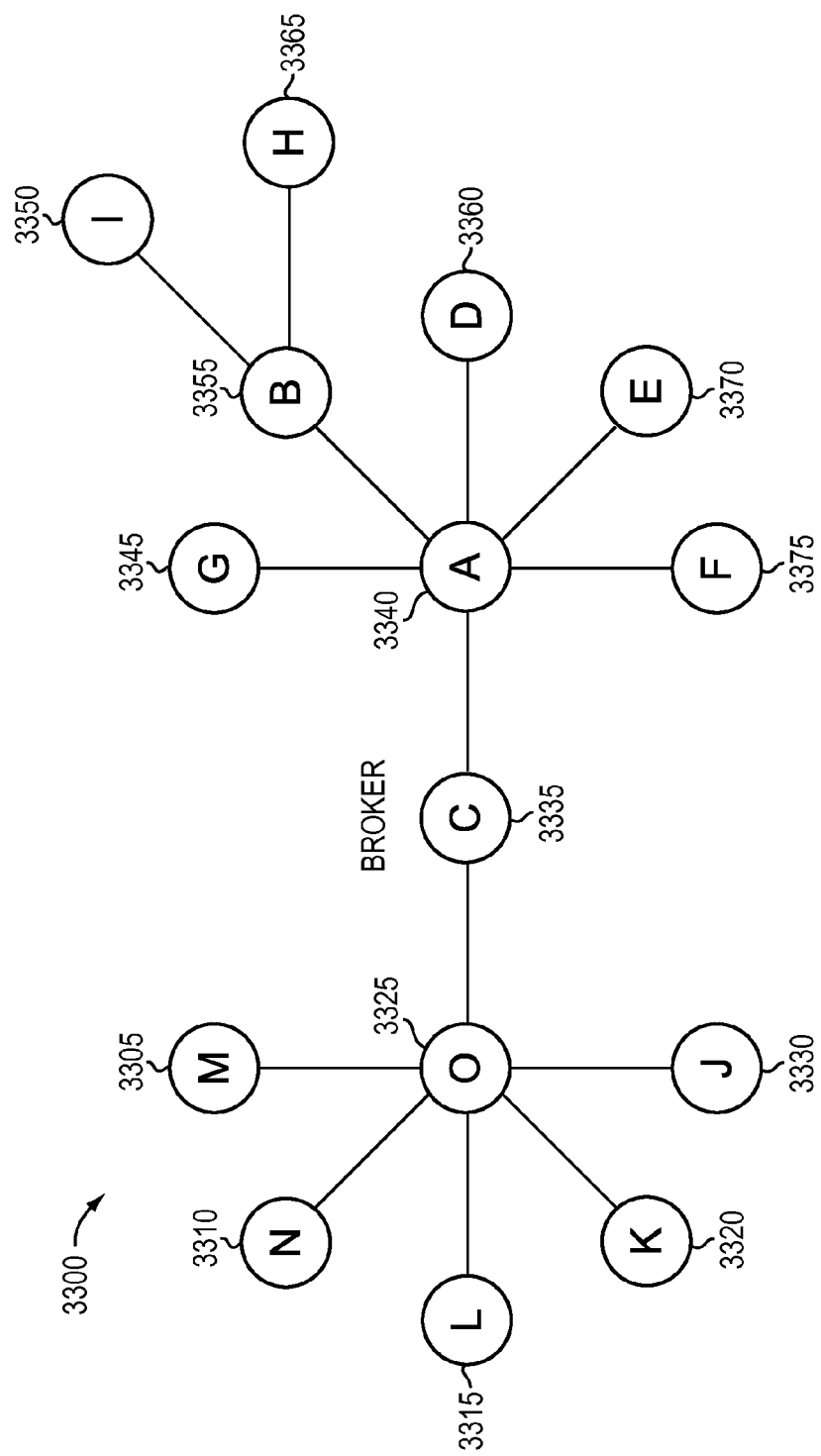
FIG. 33 is a simplified illustration of a broker, in accordance with an embodiment of the present disclosure.

Refer now to the example embodiment of FIG. 33, which illustrates a broker. Element C 3325 is the broker between the network of O 3320, M3305, N 3310, L 3315, K 3330, and J 3335 and the network of elements A 3360, G 3345, F 3365, E 3375, B 3350, D 3370, H 3355, and I 3340.

Figure 34:
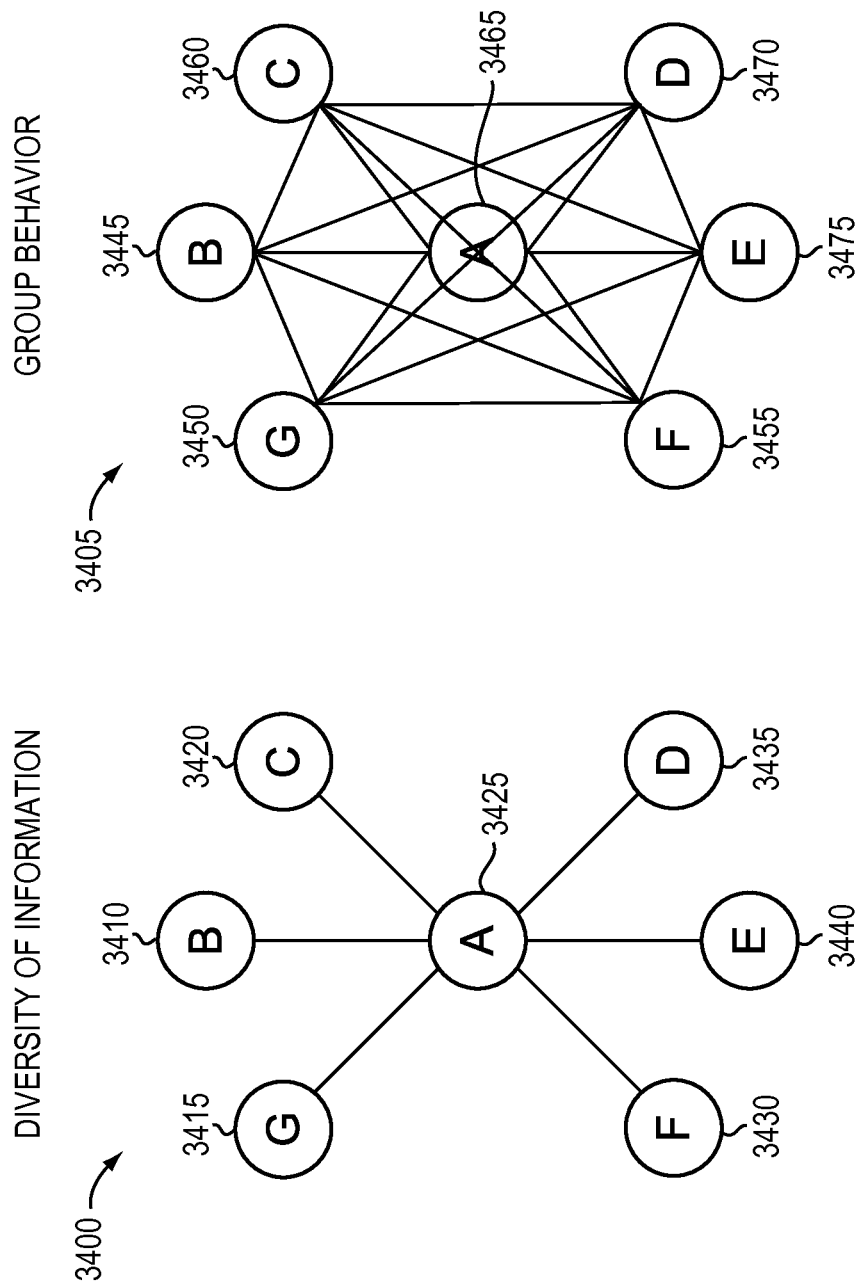
FIG. 34 is a simplified illustration of diversity of information and group behavior, in accordance with an embodiment of the present disclosure.

Refer now to the example embodiment of FIG. 34, which illustrates diversity of information 3400 and group behavior 3405. In the example embodiment of FIG. 34, diversity of information 3400 is illustrated by element A 3425 being connected to elements B 3410, C 3420, D 3435, E 3440, F 3430, and G 3415. Group Behavior 3405 is illustrated by each element A 3465, B 3445, C 3460, D 3470, E 3465, F 3455, and G 3450 being connected to each other element.

Refer now to the example embodiment of FIG. 35, which illustrates Forbidden triangle 3500. In the example embodiment of FIG. 35, element F is connected to element E 3510 but is not connected to element D 3515. Element D 3515 is connected to element E 3510 but is not connected to element 3505. In this example embodiment, if E 3510 is lost or one of the connections to E 3510 is lost then the connectivity may be lost.

Refer now to the example embodiment of FIG. 36, which illustrates a weak component, and isolated component, and a strong component. Weak component 3600 is shown by element F, connected to element H 3630 and element E 3625, and element G 3630, which is connected to element H 3620 and element 3625. Isolated component 3605 is illustrated by components F 3635, E 3640, and D 3640 which are not connected to other components. Strong Component 3610 is illustrated by elements F 3650, E 3655, and D 3660 which all have bidirectional links with each other.

Refer now to the example embodiment of FIG. 37, which illustrates two cliques. In the example embodiment of FIG. 37, Clique 3705, which consists of elements E 3720, H 3725, and G 3730 and clique 3710, which consists of element C 3710, element B 3740, and element A 3745. Element F 3715 is not in a clique.

Refer now to the example embodiment of FIG. 38, which illustrates 2-cliques. In the example embodiment of FIG. 38, Elements F 3820, E 3825, H 3830, G 3835 and D 3840 form 2-Clique 3810. Elements E 3825, D 3840 and B 3850 form 2-clique 3815. Elements D 3840, B element 3850, C 3845, and A 3855 form 2-clique 3805.

Refer now to the example embodiment of FIG. 39, which illustrates a sample density for two cliques. In the example embodiment of FIG. 39, Clique 3905, which consists of elements E 3920, H 3925, and G 3930, has density of 0.38 which is the same density of clique 3910, which consists of element C 3910, element B 3940, and element A 3945. Element F 3915 is not in a clique.

Refer now to the example embodiment of FIG. 40 which illustrates two networks of the same density. Graph A 4010 has elements A 4015, F 4040, C 4025, D 4030, B 4020, and E 4035. Graph B 4005 has element 6 4000, element 2 4050, element 1 4045, element 5 4065, element 3 4055, and element 4 4050. Graph A 4010 and Graph B 4005 have the same density of 0.40.

Refer now to the example embodiment of FIG. 41, which represents co-locating data and processing power with network elements. FIG. 41 illustrates data processing and storage elements 4105, 4110, and 4115 over a network topology such as that of FIG. 30. In the example embodiment of FIG. 41, the data processing and storage elements may be located where they are best able to store information for and transfer information to the members of the network.

Refer now to the example embodiment of FIG. 42, which illustrates a sample method for creating a health care model. In the example embodiment of FIG. 1, the healthbook healthcare model is loaded (step 4205). The healthcare silos are discovered (step 4210). A Healthcare network system topology based on the model is created (Step 4215). The topology is traversed to check class and object naming for consistency for each silo (step 4220). The data is optimized based on duplicate objects or isolated nodes or low value relationships (step 4225). The topology is finalized (step 4230).

Refer now to the example embodiment of FIG. 43. In the example embodiment of FIG. 43, a model is loaded into a computer system (step 4310). Entities from each healthcare silos are discovered (step 4315). The model is populated (step 4320). Data consistency is checked (name, relationships, and data objects) (step 4325). The topology is finalized by traversing the network from all stakeholder perspectives to compete the discovery process (step 4330). The discovery process is started for other healthcare networks (step 4335).

Refer now to the example embodiment of FIG. 44. In the example embodiment of FIG. 44, supplier 4400, payer 4405, insurer 4410, patient 4415, and provider 4420 are mapped to model 4425. Model 4425 is composed of a number of models corresponding to the objections and properties that need to be modeled for each of supplier 4400, payer 4405, insurer 4410, patient 4415, and provider 4420

Data Analysis

Refer now to the example embodiment of FIG. 45. Health care network 4500 has nodes P1 4505, which represents a patient, P2 4510, which represents patent's 4510 doctor, P3 4515, which represents patent's 4510 insurer, and P4 4520, which represents patent's 4510 Nurse 4520.

Refer now to the example embodiment of FIGS. 46a and 46b. In these examples, additional information is layered over the example embodiment of FIG. 45. A determination for the data set is made for health care system network 4600 (step 4650). In determining the data set it is determined that Patient P1 4605 has symptom 4607. Based on symptom 4607, Doctor 4610 performs diagnostic and services 4612, nurse 4620 performs diagnostic and services 4622. Insurer 4614 makes a determination of the analysis of diagnostics and services based on symptoms 4617 (step 4655). In this way, insurer 4615 may determine whether the diagnostics and services were correctly performed based on symptom 4607.

Refer now to the example embodiment of FIG. 47. Friends/Family network 4700 has nodes P1 4705, which represents a patient or person, P5 4710, which represents patent's 4710 father, P6 4715, which represents patent's 4710 daughter, and P7 4720, which represents patent's 4710 Sister.

Refer now to the example embodiment of FIGS. 48a and 48b. In these example embodiments, conditions and symptoms are overlaid on the friends/family network 4800. A data set is determined (step 4850). For example, patient P1 4805 has condition C1 with symptoms s1, s2, s3, and s4 4807. P5, P1's father 4810, has conditions C1, C3, and C5 4812. P6, P1's daughter 4815, has conditions C2 and C4 4817. P7, P1's sister 4820, has condition C1 4822. A deduction is made based on the data set (step 4855). In an embodiment, a deduction may be made that condition C1 is heredity. In an alternative embodiment, a determination may be made that condition C1 is contagious. In further embodiments, different determinations may be made based on the conditions and symptoms in the network.

Refer now to the example embodiment of FIG. 49. Research network 4900 has nodes P1 4905, which represents a patient or person, P8 4910, which represents patent's 4910 researcher, P9 4915, which represents patent's 4910 worker in the research network, and P10 4920, which represents patent's 4910 scientist.

Refer now to the example embodiments of FIGS. 50a and 50b. In these embodiments, characteristics are overlaid on research network 5000. In these embodiments, a determination of a data set is made to determine of what nodes research network 5000 should consist (step 5050). In these embodiments, researcher 5010, worker 5015, and scientist 5020 are interested in studying characteristic c1 5007 of patient P1 5005. An analysis is made that patients have characteristic c1 5007 (step 5055).

Refer now to the example embodiment of FIG. 51. Marketplace network 5100 has nodes P1 5105, which represents a patient or person, P11 5110, which a manufacturer 5110 researcher, P12 5115, which represents a manufacture, and P13 5120, which a manufacturer.

Refer now to the example embodiments of FIGS. 52a and 52b. In these embodiments, conditions and products on marketplace network 5200. A determination is made what dataset is related to marketplace 5200 (step 5250). In these embodiments, manufactures 5210, 5215, and 5220, with products P1 5212, P2 5217, and P3 5222, respectively, are interested with a patient with condition C1 5207. In these embodiments, a connection between patient P1 5205 may be made with manufacture 5210, 5215, and 5220.

Data Placement

Refer now to the example embodiment of FIG. 53, which illustrates a plurality of health care networks with local storage and a central repository. In the example embodiment of FIG. 53 there are health care networks 5305, 5315, 5325, 5335, 5345, and 4955 which each have local storage 5310, 5320, 5330, 5340, 5350, and 5360. Also present is central storage 5300. Data for each of the entities in the health care network may be stored in local storage or central storage.

In many embodiments, where there is geographically disperse storage, it may be beneficial to shift data closer to where it is being accessed. In some embodiments, data accessed often may be referred to as hot or warmer data. In most embodiments, data that is accessed less often may be cold or colder data. In further embodiments with a central or non-local storage, it may be beneficial to store the colder data on non-local storage. In certain embodiments, moving cold data away from a local repository may enable the local repository to store more hot data. In many embodiments, storing hot or more accessed data geographically close to the place where the data is being accessed may enable the data to be accessed faster and lower latency for accessing this data. In certain embodiment, it may be beneficial to move the colder data to a non-local repository and the hotter data closer to where the data is being accessed.

Refer now to the example embodiment of FIG. 54, which illustrates a plurality of health care networks with local storage and a central repository. In the example embodiment of FIG. 54 there are health care networks 5405, 5415, 5425, 5435, 5445, and 5455 which each have local storage 5410, 5420, 5430, 5440, 5450, and 5460, respectively. Also present is central storage 5400. Refer now as well to FIG. 56 in addition to FIG. 54. At local storage 5410, 5420, 5430, 5440, 5450, and 5460 a determination may be made about the heat of the data (Step 5505). In this embodiment, a determination is made if the data is cold. The cold data is shifted from local storage 5410, 5420, 5430, 5440, 5450, and 5460 to central storage 5400 (step 5610). In other embodiments, the shift of data may occur at different times at each local storage based on calculations at that local storage.

Refer now to the example embodiment of FIG. 55, which illustrates a plurality of health care networks with local storage and a central repository. In the example embodiment of FIG. 55 there are health care networks 5505, 5515, 5525, 5535, 5545, and 5555 which each have local storage 5510, 5520, 5530, 5540, 5550, and 5560. Also present is central storage 5500. Refer now as well to FIG. 56 in addition to FIG. 55. At central storage 5500 a determination may be made about the heat of the data (Step S605). In this embodiment, a determination is made if the data is hot. The hot data is shifted from central storage 5500 to local storage 5510, 5520, 5530, 5540, 5550, and 5560 (step 5610). In other embodiments, the shift of data may occur at different times the central storage based on predetermined factors.

Refer now to the example embodiments of FIGS. 57a and 57b, which illustrate a location hierarchy and a method for creating a location hierarchy. In these example embodiments a network, such as the network of FIG. 43, is divided into a series of regions such as region 1 5704, region 2 5710, and region 3 5715 (step 5750). The regions are divided into zones such as zone 1 5706 and zone 5707 in region 5705 (step 5755). As well, region 5710 is divided into zones 5711 and zone 5712 (step 5755). Region 5715 is divided into zones 5716 and zone 5717 (step 5755).

Refer now to the example embodiment of FIG. 58, which illustrates a distributed storage architecture with location specifications. Region 1 5805 is divided into geographic location zone 1 5810 and geographic location zone 2 5815. Geographic location zone 1 has access 5810 has access to server 1 5820 and server 2 5825. Geographic location zone 2 has access to server 2 5825 and server N 5830. In this embodiment hot data, based on recent access request or recently stored data is stored on server 1 5820. Server 2 5825 may have local server flash. Disk arrays 5835 stores cold storage data, which may be valid for a number of years. Tape drives 5840 may hold data that has aged beyond a specified period of years. Refer now as well to the example embodiment of FIG. 59. A user trys to access healthcare data (step 5909). A determination is made if the data is hot (step 5910). If the data is hot (5915), then local access such as on a local server occurs (step 5920). If the data is not hot, a determination is made if the data is cold (step 5925). If the data is determined to be cold, then the data is access in the central storage region, such as disk arrays 5835 (step 5930). Otherwise (step 5935) the data may be accessed in a further data location such as the tape drives 5840 step (step 5940).

Refer now to the example embodiment of FIG. 60, which illustrates a distributed storage architecture. Server 1 6005 has hot data, where hot data may be recently accessed or created data. Server 2 6010 may also store hot data and may have local server flash for quick access to the server data. Server N 6015 may also store hot data. Disk arrays 6020 may be used to store cold data for a given period of time. In this embodiment, the cold data is kept on the disk arrays so that it may be accessed, but at a higher latency than hot data. After a given period of time, the cold data is archived on tape drives 6025 for long term storage.

In some embodiments, the current disclosure may enable modeling of healthcare silos of healthcare system connection between healthcare silos. In certain embodiments, the model may provide connectedness to all players in different healthcare silo to enable data analysis. In further embodiments, the model may have a view of other edges and networks. In still further embodiments, the model may enable patients and healthy people to make better healthcare choice based on multiple data and may enable reduced care and treatment costs. In certain embodiments, the model may enable propagation of costs and care cost analysis over relationships to patients, labs, insurance/payers, employers and care providers. In some embodiments, the model may enable referrals via the created social network topology.

In alternative embodiments, the model may propagate healthy behavior data within the healthcare social network and may change the behavior of others. In some embodiments, the model may enable data analysis to provide care providers target treatments based on various behavior, geo data and network connectedness. In at least some embodiments, data analysis may provide the pharmaceutical and equipment manufactures a direct relationship with people, which may not be possible in the current siloed healthcare system. In other embodiments, big data analysis may create markets for new products including insurance policies offered over on-line, tailored insurance policies for certain age, ethnicity, geo and behaviors, differentiated care provided by nearby hospitals, care and doctor ratings, cost analysis of care, procedures and treatments, enables DNA and hereditary research and analysis, lab data, detection of errors, false positives, false negatives. In still further embodiments, as the healthcare silos may be modeled in one system over many geo locations, the storage specifically the cloud federation and data placement decisions may be made based on the data access (hot vs cold) and location or data access latency numbers.

In certain embodiments, propagation of node properties and aggregation of connected node properties onto a focal node may facilitate readying the data set for analysis. In some embodiments, the focal node may be the node on which the analysis is performed. In alternative embodiments, an example of a focal node may be the node P1 described in the example embodiment. In other embodiments, properties that may be prepared for analysis may be behavior types, conditions, treatments, symptoms, geography data, cost of treatments and node/graph connectedness and relations. In at least some embodiments, analysis over the focal node may be enabled for detection of errors, false positives and false negatives. In further embodiments, the scope of analysis may be determined by the social network graph distance. In other embodiments, an analysis may start with a small radius and may grow depending upon the underlying architecture that can support time and space complexity In certain embodiments, a data placement architecture may enable to gathering of metadata from various regions for correlating other region's data sets. In other embodiments, a data placement architecture may enables multiple healthbook like application run on various regions/zones and sync data at the application level. In further embodiments, a data placement architecture may enable direct data transfers to other data warehouse architectures such as Hadoop and no-sql databases and filesystems. In at least some embodiments, a data placement architecture may run Hadoop's map-reduce algorithm when Hadoop workload is brought for analysis in parallel. In alternative embodiments, a data placement architecture may present data seamlessly as one pool of data to the application The methods and apparatus of this invention may take the form, at least partially, of program code (i.e., instructions) embodied in tangible media, such as floppy diskettes, CD-ROMs, hard drives, random access or read only-memory, or any other machine-readable storage medium. When the program code is loaded into and executed by a machine, such as the computer of FIG. 61, the machine becomes an apparatus for practicing the invention. When implemented on one or more general-purpose processors, the program code combines with such a processor 6103 to provide a unique apparatus that operates analogously to specific logic circuits. As such a general purpose digital machine can be transformed into a special purpose digital machine. FIG. 62 shows Program Logic 6234 embodied on a computer-readable medium 6230 as shown, and wherein the Logic is encoded in computer-executable code configured for carrying out the reservation service process of this invention and thereby forming a Computer Program Product 6200. The logic 4634 may be the same logic 6140 on memory 6104 loaded on processor 6103. The program logic may also be embodied in software modules, as modules, or as hardware modules. The processors or machines may be embodied as one or more virtual processors or machines, respectively.

The logic for carrying out the method may be embodied as part of the system described below, which is useful for carrying out a method described with reference to embodiments shown in, for example, FIG. 42 and FIG. 43. For purposes of illustrating the present invention, the invention is described as embodied in a specific configuration and using special logical arrangements, but one skilled in the art will appreciate that the device is not limited to the specific configuration but rather only by the claims included with this specification.

What is claimed is:

1. A computer implemented method comprising:
capturing development and behavior of different social healthcare networks in nodes and relationships of a social dataset in a computer based model enabling integration of different health care systems into a single social healthcare network; wherein each node of the nodes is enabled to be connected to each other node of the nodes by one or more relationship of the relationships; wherein the relationships between the nodes includes familial relationships between nodes representing family members to form a family network; wherein each node of the nodes is enabled to have a set of symptoms, a set of characteristics, and a set of conditions;
determining using the computer based model a sub-set of the social dataset for analysis; wherein the determination of the sub-set includes:
performing an actor level analysis of each node of the nodes; wherein the actor level analysis includes an indegree analysis and an outdegree analysis; wherein the indegree analysis include an analysis of the number of ties received by a node; wherein the outdegree analysis includes an analysis of the number of ties to that node by each other connected node; wherein the actor analysis further include a determination of betweeness for the node; wherein betweeness measures how often the node rests between two other nodes linking the two other nodes;
performing positional analysis of the nodes of the healthcare network; and
deriving a role analysis from the positional analysis;
layering over the set of conditions, set of characteristics, and the set of symptoms over the family network; and
performing an analysis, using the computer based model on the sub-set; wherein the analysis includes determining which conditions of a set of conditions for a node of the nodes are hereditary; wherein the analysis further includes determining which conditions of the set of conditions for the node of the nodes is contagious.

2. The method of claim 1 further comprising propagating node and aggregation of connected node properties onto a focal node for data set analysis.

3. The method of claim 1 further comprising preparing properties for analysis based on behavior types, conditions, treatments, symptoms, geography data, cost of treatments, and node connectiveness.

4. The method of claim 1 further comprising analyzing detection of errors, false positive and false negatives.

5. The method of claim 1 further comprising determining the scope of the analysis by the distance of the social network graph distance.

6. A system for representing a health care network, the system comprising:
one or more computer having a memory and one or more processor cores;
computer-executable program code operating in memory, wherein the computer-executable program code is configured for execution of:
capturing development and behavior of different social healthcare networks in nodes and relationships of a social dataset in a computer based model enabling integration of different health care systems into a single social healthcare network; wherein each node of the nodes is enabled to be connected to each other node of the nodes by one or more relationship of the relationships; wherein the relationships between the nodes includes familial relationships between nodes representing family members to form a family network; wherein each node of the nodes is enabled to have a set of symptoms, a set of characteristics, and a set of conditions;

determining using the computer based model a sub-set of the social dataset for analysis; wherein the determination of the sub-set includes:

performing an actor level analysis of each node of the nodes; wherein the actor level analysis includes an indegree analysis and an outdegree analysis; wherein the indegree analysis include an analysis of the number of ties received by a node; wherein the outdegree analysis includes an analysis of the number of ties to that node by each other connected node; wherein the actor analysis further include a determination of betweeness for the node; wherein betweeness measures how often the node rests between two other nodes linking the two other nodes;

performing positional analysis of the nodes of the healthcare network; and deriving a role analysis from the positional analysis; and layering over the set of conditions, set of characteristics, and the set of symptoms over the family network; and performing an analysis, using the computer based model on the sub-set; wherein the analysis includes determining which conditions of a set of conditions for a node of the nodes are hereditary; wherein the analysis further includes determining which conditions of the set of conditions for the node of the nodes is contagious.

7. The system of claim 6 wherein the code is further enabled for propagating node and aggregation of connected node properties onto a focal node for data set analysis.

8. The system of claim 6 wherein the code is further enabled for preparing properties for analysis based on behavior types, conditions, treatments, symptoms, geography data, cost of treatments, and node connectiveness.

9. The system of claim 6 wherein the code is further enabled for analyzing detection of errors, false positive and false negatives.

10. The system of claim 6 wherein the code is further enabled for determining the scope of the analysis by the distance of the social network graph distance.

11. A computer program product for representing a health care network, the computer program product comprising:

a non-transitory computer-readable storage medium encoded with computer-executable program code enabling:

capturing development and behavior of different social healthcare networks in nodes and relationships of a social dataset in a computer based model enabling integration of different health care systems into a single social healthcare network; wherein each node of the nodes is enabled to be connected to each other node of the nodes by one or more relationship of the relationships; wherein the relationships between the nodes includes familial relationships between nodes representing family members to form a family network; wherein each node of the nodes is enabled to have a set of symptoms, a set of characteristics, and a set of conditions;

determining using the computer based model a sub-set of the social dataset for analysis; wherein the determination of the sub-set includes:

performing an actor level analysis of each node of the nodes; wherein the actor level analysis includes an indegree analysis and an outdegree analysis; wherein the indegree analysis include an analysis of the number of ties received by a node; wherein the outdegree analysis includes an analysis of the number of ties to that node by each other connected node; wherein the actor analysis further include a determination of betweeness for the node; wherein betweeness measures how often the node rests between two other nodes linking the two other nodes;

performing positional analysis of the nodes of the healthcare network; and deriving a role analysis from the positional analysis; and layering over the set of conditions, set of characteristics, and the set of symptoms over the family network; and performing an analysis, using the computer based model on the sub-set; wherein the analysis includes determining which conditions of a set of conditions for a node of the nodes are hereditary; wherein the analysis further includes determining which conditions of the set of conditions for the node of the nodes is contagious.

12. The computer program product of claim 11 wherein the code is further enabled for propagating node and aggregation of connected node properties onto a focal node for data set analysis.

13. The computer program product of claim 11 wherein the code is further enabled for preparing properties for analysis based on behavior types, conditions, treatments, symptoms, geography data, cost of treatments, and node connectiveness.

14. The computer program product of claim 11 wherein the code is further enabled for analyzing detection of errors, false positive and false negatives.

15. The computer program product of claim 11 wherein the code is further enabled for determining the scope of the analysis by the distance of the social network graph distance.

16. The computer program product of claim 11 wherein the analysis includes creating a sub-set of nodes for a research project; wherein the sub-set of nodes is created by including nodes with a specific condition in a research project network of nodes.

17. The computer program product of claim 11 wherein the nodes make up a plurality of data networks; wherein the computer model connects the data networks through creating relationships between the nodes; wherein the computer model enables gathering of metadata from the plurality of data networks to enable correlations between the plurality of data networks.

18. The computer program product of claim 11 wherein the computer model enables the plurality of data networks to appear as a single pool of data for analysis.

19. The computer program product of claim 18 where the code is further enabled to propagate node properties and connections of node properties to a focal node.

20. The computer program product of claim 19 wherein analysis over the focal node is enabled to detect errors, false positives and false negatives.

* * * * *